(12) United States Patent
Su et al.

(10) Patent No.: US 10,611,777 B2
(45) Date of Patent: *Apr. 7, 2020

(54) IMIDAZOPYRIDAZINE COMPOUNDS AND THEIR USE

(71) Applicant: HUTCHISON MEDIPHARMA LIMITED, Shanghai (CN)

(72) Inventors: Wei-Guo Su, Shanghai (CN); Guangxiu Dai, Shanghai (CN); Weihan Zhang, Shanghai (CN); Wei Deng, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/227,801

(22) Filed: Dec. 20, 2018

(65) Prior Publication Data

US 2019/0127391 A1 May 2, 2019

Related U.S. Application Data

(63) Continuation of application No. 15/513,811, filed as application No. PCT/CN2015/090367 on Sep. 23, 2015, now Pat. No. 10,208,066.

(30) Foreign Application Priority Data

Sep. 24, 2014 (CN) .......................... 2014 1 0494483

(51) Int. Cl.
| | | |
|---|---|---|
| *C07D 487/04* | (2006.01) | |
| *A61P 19/02* | (2006.01) | |
| *A61P 35/00* | (2006.01) | |
| *C07D 519/00* | (2006.01) | |
| *A61P 11/00* | (2006.01) | |
| *A61P 29/00* | (2006.01) | |
| *A61P 37/00* | (2006.01) | |

(52) U.S. Cl.
CPC ............ *C07D 519/00* (2013.01); *A61P 11/00* (2018.01); *A61P 19/02* (2018.01); *A61P 29/00* (2018.01); *A61P 35/00* (2018.01); *A61P 37/00* (2018.01); *C07D 487/04* (2013.01)

(58) Field of Classification Search
CPC ......... C07D 487/04; A61P 19/02; A61P 35/00
See application file for complete search history.

(56) References Cited

U.S. PATENT DOCUMENTS

| | | | |
|---|---|---|---|
| 6,248,740 B1 | 6/2001 | Kawano et al. | |
| 10,208,066 B2* | 2/2019 | Su .................... | C07D 487/04 |
| 2009/0312319 A1 | 12/2009 | Ren et al. | |
| 2010/0202963 A1 | 8/2010 | Gallatin et al. | |
| 2013/0344061 A1 | 12/2013 | Palombella et al. | |
| 2014/0120060 A1 | 5/2014 | Palombella et al. | |
| 2014/0120083 A1 | 5/2014 | Stern et al. | |
| 2014/0134133 A1 | 5/2014 | Xi | |
| 2014/0179718 A1 | 6/2014 | Evarts et al. | |

FOREIGN PATENT DOCUMENTS

| | | |
|---|---|---|
| JP | 2001-507854 A | 3/2011 |
| WO | WO 98/49167 | 11/1998 |
| WO | WO 2005/113554 A2 | 12/2005 |
| WO | WO 2005/113556 A1 | 12/2005 |
| WO | WO 2007/113226 A1 | 10/2007 |
| WO | WO 2008/052733 A1 | 5/2008 |
| WO | WO 2008/052734 A1 | 5/2008 |
| WO | WO 2008/138834 A1 | 11/2008 |
| WO | WO 2009/060197 A1 | 5/2009 |
| WO | WO 2009/085230 A1 | 7/2009 |
| WO | WO 2010/007099 A1 | 1/2010 |
| WO | WO 2012/116237 A2 | 8/2012 |
| WO | WO 2013/052699 A2 | 4/2013 |
| WO | WO 2013/082540 A1 | 6/2013 |
| WO | WO 2013/090725 A1 | 6/2013 |

OTHER PUBLICATIONS

Majchrzak et al. Molecules 2014, 19, 14304-14315 (Year: 2014).*
International Search Report of PCT/CN2015/090367 dated Dec. 28, 2015, WIPO, China.
Supplementary European Search Report of EP 15 84 3649 dated Feb. 12, 2018, EPO, Germany.
English translation of Ukrainian Office Action in Appl. No. a201703837 dated Feb. 19, 2018, UKRPATENT, Ukraine.
Ghigo, A. et al. "Isoform Selective Phosphoinositide 3-Kinase γ and δ Inhibitors and Their Therapeutic Potential," Recent Patents on Inflamation & Allergy Discovery, 2(1):1-10, Bentham Science Publishers Ltd. (2008).
Pillinger, G. et al. "Target PI3Kδ and PI3Kγ Signalling Disrupts Human AML Survival and Bone Marrow Stromal Cell Mediated Protection," Oncotarget, 7(26):39784-39795 (2016).

(Continued)

*Primary Examiner* — Emily A Bernhardt
(74) *Attorney, Agent, or Firm* — Potomac Law Group, PLLC

(57) ABSTRACT

This disclosure provides novel imidazopyridazine compounds of formula (I) and pharmaceutical acceptable salt thereof, pharmaceutical compositions containing them, a process for preparing them, and their practical effect in inhibiting PI$_3$K and potential use in treating a disease responsive to inhibition of PI$_3$K, for example, an inflammatory disease, autoimmune disease or cancer.

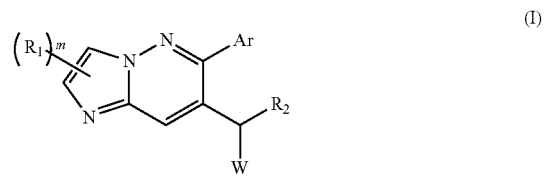

19 Claims, 1 Drawing Sheet

(56) References Cited

OTHER PUBLICATIONS

Landgren, O. et al. "MYD88 and Beyond: Novel Opportunities for Diagnosis, Prognosis and Treatment in Waldenström's Macroglobulinemia," Leukemia, 28:1799-1803, Macmillan Publishers Ltd. (2014).
Hawkins, P.T. et al. "PI3K Signalling in Inflammation," Biochimica et Biophysica Acta 1851, pp. 882-887, Elsevier B.V. (2015).
Subramaniain, P.S. et al. "Targeting Nonclassical Oncogenes for Therapy in T-ALL" Cancer Cell 21:459-472, Elsevier Inc. (2012).
Ghigo, A. et al. "PI3K Inhibition in Inflammation: Toward Tailored Therapies for Specific Diseases," Bioessays 32:185-196, Wiley Periodicals, Inc. (2010).
Sujobert, P. et al. "Essential Role for the p110δ Isoform in Phosphoinositide 3-Kinase Activation and Cell Proliferation in Acute Myeloid Leukemia," Blood 106(3):1063-1066 (2005).
Cui, Y. et al. "A Novel Phosphatidylinositol-3-Kinase δ Inhibitory Idelalisib," Drugs & Clinic, pp. 552-556, China Academic Journal Electronic Publishing House (2014).
Maharaj, K.K., et al, "Modulation of T cell Compartment in a Preclinical CLL Murine Model by a Selective PI3K Delta Inhibitor, TGR-1202," 58$^{th}$ ASH Annual Meeting and Exposition, Abstract No. 3236, Dec. 3-6, The American Society of Hematology (2016).
Srikantharajah, S. et al. "Targeting Phosphoinositide 3-Kinase δ for the Treatment of Respiratory Diseases," Ann. N.Y. Acad. Sci., pp. 35-39 (2013).
Cushing, T. et al. "PI3Kδ and PI3Kγ as Targets for Autoimmune and Inflammatory Diseases," J. of Med. Chem. 55:8559-8581 (2012).
Rowan, W.C. et al. "Targeting Phosphoinositide 3-Kinase δ for Allergic Asthma," Biochem. Soc. Trans. 40(1):240-245 (2012).
Suárez-Fueyo, A. et al. "Enhanced Phosphoinositide 3-Kinase δ Activity Is a Frequent Event in Systemic Lupus Erythematosus That Confers Resistance to Activation-Induced T Cell Death," J. of Immunology, 187:2376-2385 (2011).
Wang, Y. et al, "Inhibition of PI3K δ Improves Systemic Lupus in Mice," Inflammation, pp. 1-6, Springer-Science Business Media, New York, Published online Jan. 21, 2014.
Suárez-Fueyo, A. et al. "Inhibition of PI3Kδ Reduces Kidney Infiltration by Macrophages and Ameliorates Systemic Lupus in the Mouse," J. of Immunology, 193: 543-554 (2014).
Roller, A. et al. "Blockade of Phosphatidylinositol 3-Kinase (PI3K)δ or PI3Kγ Reduces IL-17 and Ameliorates Imiquimod-Induced Psoriasis-like Dermatitis," J. of Immunology, 189:4612-4620 (2012).
Haylock-Jacobs, S. "PI3Kδ drives the Pathogenesis of Experimental Autoimmune Encephalomyelitis by Inhibiting Effector T Cell Apoptosis and Promoting TH17 Differentiation," J. of Autoimmunity, 36:278-287, Elsevier Ltd. (2011).
Ali, K. et al. "Inactivation of PI(3)K p110δ Breaks Regulatory T-Cell-Mediated Immune Tolerance to Cancer," Nature, pp. 1-9, Macmillan Publishers Ltd. (2014). Published online Jun. 11, 2014.
Vakkalanka, S. et al. "TGR-1202 Suppresses Acute Myeloid Leukemia (AML) and Acute Lymphoblastic Leukemia (ALL) Cells Via Selective Inhibition of PI3Kδ Kinase," 54$^{th}$ ASH Ann. Meeting and Exposition, Abstract #2610, Dec. 8-11, The American Society of Hematology (2012).

Xing, Y. et al "Selective Small Molecule Inhibitors of p110α and δ Isoforms of Phosphoinosity I-3-Kinase are Cytotoxic to Human Acute Myeloid Leukemia Progenitors," Exp. Hematology 40:922-933, Elsevier Inc. (2012).
Billottet, C. et al. "A Selective Inhibitor of the p110δ Isoform of PI3-Kinase Inhibits AML Cell Proliferation and Survival and Increases the Cytotoxic Effects of VP16," Oncogene, 25:6648-6659, Nature Publishing Group (2006).
Markham, A. "Idelalisib: First Global Approval," Drugs, 74:1701-1707, Springer Int'l Publishing (2014).
Brown, J.R. et al. "Idelalisib, An Inhibitor of Phosphatidylinositol 3-Kinase p110δ, for Relapsed/Refractory Chronic Lymphocytic Leukemia," Blood, 123(22):3390-3397, The American Society of Hematology (2014).
Ikeda, H. et al. "PI3K/p110δ is a Novel Therapeutic Target in Multiple Myeloma," Blood, 116(9):1460-1468, The American Society of Hematology (2010).
Gheorghe, D., Ph.D. et al. "Non-Hodgkin's Lymphoma", Onkos Study, Decision Resources, LLC (2013).
Kahl, B.R. et al. "A Phase 1 Study of the PI3Kδ Inhibitor Idelalisib in Patients with Relapsed/Refractory Mantle Cell Lymphoma (MCL)," Blood, 123(22):3398-3406, The American Society of Hematology (2014).
Gopal, A.K., M.D. et al. "PI3Kδ Inhibition by Idelalisib in Patients with Relapsed Indolent Lymphoma," N. Engl. J. Med 370(11):1008-1018, Massachusetts Medical Society (2014).
Lunning, M. et al. "Combination of Ublituximab, TGR-1202, and Bendamustine Demonstrates Significant Activity in Patients with Advanced DLBCL and Follicular Lymphoma," 58$^{th}$ ASH Ann. Meeting and Exposition, Abstract #4197, Dec. 3-6, The American Society of Hematology (2016).
Deng, C. et al. "The PI3K Delta Inhibitor TGR-1202 and Proteasome Inhibitor Carfilzomib Are Highly Synergistic in Killing Human B- and T-Cell Lymphoma Cells," 55$^{th}$ ASH Ann. Meeting and Exposition, Abstract #4421, Dec. 7-10, The American Society of Hematology (2013).
Meadows, S. A. et al. "PI3Kδ Inhibitor, GS-1101 (CAL-101), Attenuates Pathway Signaling, Induces Apoptosis, and Overcomes Signals from the Microenvironment in Cellular Models of Hodgkin Lymphoma," Blood, 119(8):1897-1900, The American Society of Hematology (2012).
Ramchandren, R., M.D. et al. "A Phase I Trial of TGR-1202, a Next Generation Once-Daily PI3Kδ Inhibitor, in Combination with Brentuximab Vedotin, in Patients with Relapsed/Refractory Hodgkin's Lymphoma," 58$^{th}$ ASH Ann. Meeting and Exposition, Abstract #4146, Dec. 3-6, The American Society of Hematology (2016).
Chen, Y. et al. "Idelalisib Induces G1 Arrest and Apoptosis in Chronic Myeloid Leukemia K562 Cells," Oncology Reports 36:3643-3650 (2016).
Stark, A.K. et al. "PI3K Inhibitors in Inflammation Autoimmunity and Cancer", Curr. Opin. Pharmacol. 23:82-91 (2015).
Rommel, C. et al., "PI3K delta and PI3K gamma: Partners in Crime in Inflammation in Rheumatoid Arthritis and Beyond?", Nature Reviews, Immunology 7:191-201 (2007).
Jean, S. et al., "Classes of Phosphoinositide 3-Kinases at a Glance", J. Cell Sci 127:923-928 (2014).

* cited by examiner

IMIDAZOPYRIDAZINE COMPOUNDS AND THEIR USE

Disclosed are novel imidazopyridazine compounds, pharmaceutical compositions thereof, methods for preparing thereof, and uses thereof.

Abnormality in PI$_3$K (phosphatidylinositol-3-kinase)-mediated signaling pathway is believed to play critical roles in the occurrence and development of a variety of malignant tumors.

PI$_3$Ks are a family of lipid kinases that phosphorylate the 3'-hydroxy group of PtdIns (phosphatidylinositol) and phosphoinositides (phosphorylated derivatives of PtdIns). These enzymes are grouped into 3 categories: class I, class II and class III, on the basis of their substrate preference and structure. Among these 3 categories, class I has been extensively studied. Class I PI$_3$Ks includes two sub-classes called class IA and class IB. There are three genes encoding class IA catalytic isoforms. Each encodes a protein product of approx. 110 kDa, denoted p110α, p110β and p110δ. These protein products form stable heterodimers, i.e. PI$_3$Kα, PI$_3$Kβ and PI$_3$Kδ, with class IA regulatory subunits having at least five isoforms (p85α, p55α, p50α, p85β and p55γ). There is a single class IB enzyme, p110γ, which associates with a unique regulatory subunit termed p101. Together this dimer is sometimes called PI$_3$Kγ.

All four class I catalytic PI$_3$K isoforms show a characteristic expression pattern in vivo. P110α and p110β are expressed widely, while p110γ and p110δ are found predominantly in leukocytes (Sundstrom T J, et al. Org. Biomol. Chem., 2009, 7, 840-850).

P110δ catalytic subunit of class IA PI$_3$K may play essential roles in the development and activation of murine B cells. P110δ-deficient mice showed a partial block in early B cell development at the pro-B to pre-B transition, a marked reduction in the number of mature splenic B cells, and a nearly complete absence of the B1 subset of mature B cells. The few B cells that can be isolated from spleens of p110δ-deficient mice fail to proliferate following clustering of the BCR (B cell receptor) with anti-IgM. Proliferation may also be impaired in response to the polyclonal B cell mitogens lipopolysaccharide and anti-CD40. Mice lacking p110δ also fail to mount effective antibody responses to TI-2 (T-independent type II) antigens (Okkenhaug K, Science. 2002, 297:1031-4).

Dysregulation and overactivation of the PI$_3$K/AKT pathway has been found in cancer cells. The specificity role of the p110δ in B-cell development can make it a promising drug target for B-cell lymphoproliferative disorders, such as CLL (chronic lymphocytic leukemia) and NHL (non-Hodgkin's lymphoma).

PI$_3$Kδ is internally involved in mammalian immune system functions such as signal transduction of T-cell, B-cell, mast cell, dendritic cell, neutrophil, NK cell, and mononuclear phagocyte. A large number of experiments of using PI$_3$Kδ inhibitor or PI$_3$Kδ deficiency animals proved that PI$_3$Kδ may play an important roles in autoimmune diseases such as respiratory diseases and rheumatoid arthritis, for example allergic airway inflammation [Nashed B F, et al. Eur J Immunol. 2007; 37(2):416-24] and acute lung injury [Purl K D, et al. Blood. 2004; 103(9):3448-56]. Due to its integral role in immune system functions, PI$_3$Kδ may also be involved in a number of diseases related to undesirable immune response such as allergic reaction, inflammatory diseases, inflammation mediated angiogenesis, rheumatoid arthritis, auto-immune diseases such as lupus, asthma, emphysema, and other respiratory diseases.

Previous studies have shown that Idelalisib (CAL-101), a potent and selective PI$_3$Kδ inhibitor, has broad antitumor activity against cancer cells of hematologic origin (Vanhaesebroeck B, Cancer Cell, 2014, 25:269-71). Patent applications, such as WO2005113556, US20130071212, and US20140179718, also disclose compounds useful as selective PI3Kδ inhibitors for treating autoimmune disease and cancer, especially for treating hematological malignancy.

Provided are compounds modulating PI$_3$K, including modulating PI$_3$Kδ selectively, for treating disorders relating to autoimmune disease and cancer, especially hematological malignancy.

Specifically, provided is a compound of formula (I):

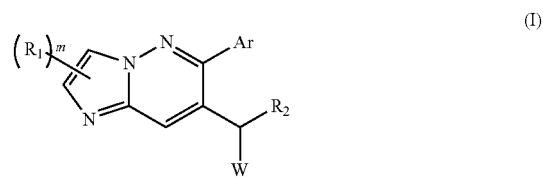

and/or its solvates, racemic mixtures, enantiomers, diastereomers, tautomers, and/or a pharmaceutically acceptable salt thereof, wherein Ar, W, R$_1$, R$_2$, and m are as defined herein.

Also provided is a pharmaceutical composition, comprising a compound of formula (I) (e.g., any of the compounds described herein) and/or a pharmaceutically acceptable salt thereof, and a pharmaceutically acceptable excipient (e.g., a pharmaceutically acceptable carrier).

Also provided is a method of in vivo or in vitro inhibiting the activity of PI$_3$K comprising contacting PI$_3$K with an effective amount of a compound of formula (I) (e.g., any of the compounds described herein) and/or a pharmaceutically acceptable salt thereof.

Also provided is a method of treating a disease responsive to inhibition of PI$_3$K in a subject comprising administering to the subject in need thereof a therapeutically effective amount of a compound of formula (I) (e.g., any of the compounds described herein) and/or a pharmaceutically acceptable salt thereof.

The diseases responsive to inhibition of PI$_3$K are chosen from inflammatory diseases, autoimmune diseases, and cancers.

Also provided is a compound of formula (I) (e.g., any of the compounds described herein) and/or a pharmaceutically acceptable salt thereof described herein for treating a disease responsive to inhibition of PI$_3$K.

Also provided is a use of a compound of formula (I) (e.g., any of the compounds described herein) and/or a pharmaceutically acceptable salt thereof described herein in the manufacture of a medicament for treating a disease responsive to inhibition of PI$_3$K.

The subject described herein can be human or animal. In some embodiments, the subject described herein is a human.

Also provided is a compound of formula (II), which can be used in the preparation of the compound of formula (I):

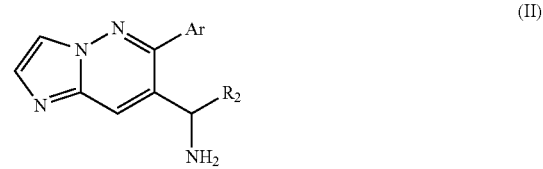

and/or a salt thereof, and/or a racemic mixture or enantiomer thereof, wherein Ar and $R_2$ are defined as in the formula (I) and both are defined below.

DEFINITIONS

Figure 1:
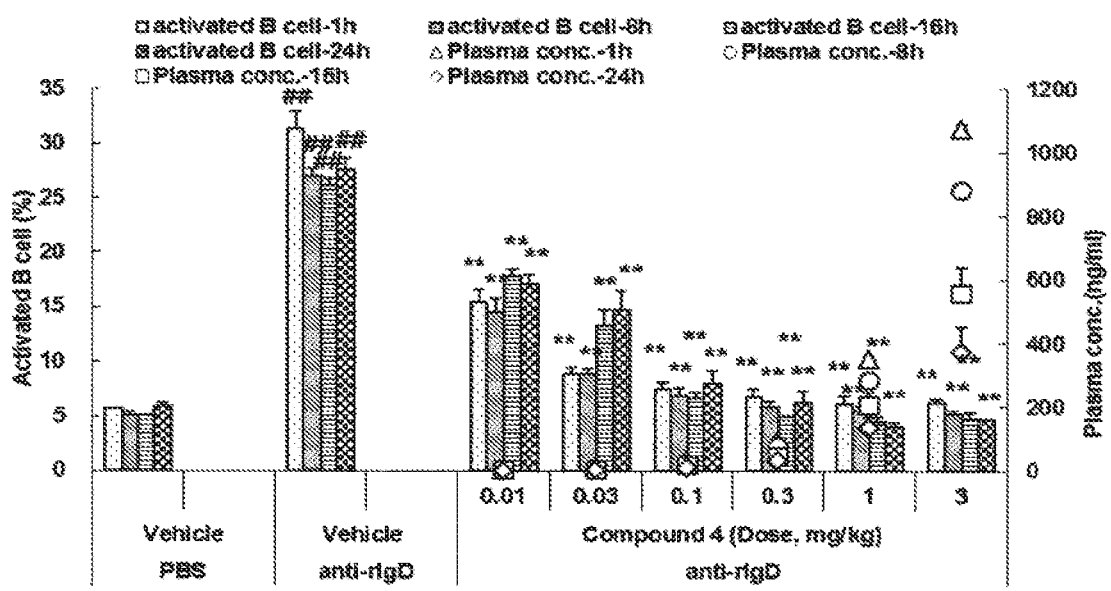
FIG. 1 shows the effect of compound 4 prepared in example 1 on anti-IgD induced B cell activation in a dose and time-dependent manner in female Wistar rats. Data of activated B cell are presented as mean±SEM (n=3). Data of plasma concentration are presented as mean±SD (n=3). Data are analyzed via ANOVA, followed by Dunnett's test vs (Vehicle+anti-IgD) group. ## shows p<0.01 vs (Vehicle+ PBS) group; ** shows p<0.01 vs (Vehicle+anti-IgD) group.

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —O($C_{1-4}$ alkyl) is attached through the oxygen. However, when the point of attachment of a group is apparent to those skilled in the art, e.g., a halo substituent, the "-" sign may be omitted.

Unless clearly indicated otherwise, use of the terms "a", "an" and the like refer to one or more.

The term "alkyl" as used herein refers to a straight or branched saturated hydrocarbon radical, and is chosen from one containing 1-18 carbon atoms, such as 1-12 carbon atoms, even further such as 1-6 carbon atoms, and yet even further such as 1-4 carbon atoms. For example, "$C_{1-6}$ alkyl" falls within the scope of "alkyl" and refers to an alkyl containing 1-6 carbon atoms. Examples of alkyl groups include, but are not limited to, methyl ("Me"), ethyl ("Et"), n-propyl ("n-Pr"), i-propyl ("i-Pr"), n-butyl ("n-Bu"), i-butyl ("i-Bu"), s-butyl ("s-Bu") and t-butyl ("t-Bu").

The term "alkenyl" as used herein refers to a straight or branched hydrocarbon radical chosen from one containing one or more, for example 1, 2, or 3, C=C double bonds, and also chosen from one containing 2-10, such as 2-6 carbon atoms, and further such as 2-4 carbon atoms. For example, "$C_{2-6}$ alkenyl" falls within the scope of alkenyl and refers to an alkenyl containing 2-6 carbon atoms. Examples of alkenyl groups include, but are not limited to, vinyl, 2-propenyl, and 2-butenyl.

The term "alkynyl" as used herein refers to a straight or branched hydrocarbon radical, chosen from one containing one or more, for example 1, 2, or 3, C≡C triple bonds and also chosen from one containing 2-10 carbon atoms, such as 2-6 carbon atoms, further such as 2-4 carbon atoms. For example, "$C_{2-6}$ alkynyl" refers to alkynyl containing 1C≡C triple bond and also containing 2-6 carbon atoms. Examples of alkynyl groups include, but are not limited to, ethynyl, 2-propynyl, and 2-butynyl.

The term "halo" as used herein includes fluoro, chloro, bromo, and iodo, and the term "halogen" as used herein includes fluorine, chlorine, bromine, and iodine.

The term "haloalkyl" as used herein refers to an alkyl radical, as defined herein, in which one or more, for example 1, 2, 3, 4, or 5, hydrogen atoms are replaced with halogen atom, the halogen atoms being all the same or different from one another. In certain embodiments, the term "haloalkyl" as used herein refers to an alkyl radical, as defined herein, in which two or more, such as 2, 3, 4, or 5 hydrogen atoms are replaced with halogen atoms, the halogen atoms being all the same. In other embodiments, the term "haloalkyl" as used herein refers to an alkyl radical, as defined herein, in which two or more hydrogen atoms, such as 2, 3, 4, or 5 hydrogen atoms are replaced with halogen atoms, the halogen atoms being not all the same as one another. Examples of haloalkyl groups include, but are not limited to, —$CF_3$, —$CHF_2$, —$CH_2CF_3$, and the like.

The term "alkoxy" as used herein refers to the group —O-alkyl, wherein the alkyl is as defined above. Examples of alkoxy groups include, but are not limited to, methoxy, ethoxy, n-propyloxy, i-propyloxy, n-butyloxy, i-butyloxy, t-butyloxy, pentyloxy, and hexyloxy, including their isomers.

The term "cycloalkyl" as used herein refers to saturated or partially unsaturated cyclic hydrocarbon radical which may have one or more, such as 1 or 2 rings, and which also may have 3 to 12, such as 3 to 8, and further such as 3 to 6 carbon atoms. For example, "$C_{3-8}$ cycloalkyl" refers to a cycloalkyl containing 3-8 carbon atoms in the ring. Examples of cycloalkyl groups include, but are not limited to, cyclopropyl, cyclobutyl, cyclopentyl, cyclohexyl, cycloheptyl, and cyclooctyl.

The term "aryl" as used herein refers to a carbocyclic hydrocarbon radical of a monocyclic ring or fused rings containing 6-14 ring carbon atoms, such as 6-12 ring carbon atoms, wherein at least one ring is aromatic and none of the other rings is heteroaryl as defined below, and the point of attachment can be on the aromatic ring or on the other rings. Examples of aryl groups include, but are not limited to, phenyl, naphthalenyl, 1,2,3,4-tetrahydronaphthalenyl, indenyl, indanyl, azulenyl, such as phenyl and naphthalenyl.

As used herein, "aryl" or "aromatic" follows Hückel's rule wherein the number of π-electrons equals 4n+2 where n is zero or any positive integer up to 6.

The term "heterocyclyl" or "heterocyclic" herein refers to a ring chosen from 4- to 12-membered monocyclic, bicyclic and tricyclic, saturated and partially unsaturated rings comprising at least one carbon atom in addition to at least one heteroatom, such as from 1-4 heteroatoms, further such as from 1-3, or further such as 1 or 2, heteroatoms, chosen, for example, from O, S, and N. The point of attachment of heterocyclyl can be on the heteroatom or carbon. "Heterocyclyl" or "heterocyclic" also refers to a monocyclic ring containing at least one heteroatom chosen from O, S, and N, or fused rings wherein, in the case of fused rings, at least one ring contain at least one heteroatom chosen from O, S, and N and none of the other rings is heteroaryl or aryl, and the point of attachment can be on the heterocyclic ring or on the other rings.

The term "heteroaryl" as used herein refers to monocyclic aromatic hydrocarbon radical having 5, 6 or 7 ring atoms, preferably having 6 ring atoms, and containing one or more, for example 1, 2 or 3, such as 1 or 2 heteroatoms independently chosen from N, O, and S (such as N) in the ring, with the remaining ring atoms being carbon; and bicyclic aromatic hydrocarbon radical having 8-12 ring atoms, such as having 9 or 10 ring atoms, and containing one or more, for example, 1, 2, 3 or 4, such as 1 or 2 heteroatoms independently chosen from N, O, and S (such as N) in the rings, with the remaining ring atoms being carbon, wherein at least one of the rings is aromatic. For example, the bicyclic heteroaryl includes a 5- to 6-membered heterocyclic aromatic ring fused to a 5- to 6-membered cycloalkyl ring, heterocyclic ring, or aryl ring wherein the point of attachment can be on the heteroaromatic ring or on the cycloalkyl ring/heterocyclic ring/aryl ring.

When the total number of S and O atoms in the heteroaryl group exceeds 1, those heteroatoms are not adjacent to one another.

The heteroaryl group also includes those wherein the N heteroatom occurs as N-oxide, such as pyrimidinyl N-oxides.

In some embodiments, the "heteroaryl" in which the heteroatom(s) in the ring is N atom(s) is defined herein as nitrogen-containing heteroaryl. The nitrogen-containing heteroaryl group also includes those wherein the N heteroatom occurs as N-oxide, such as pyridyl N-oxides Examples of the heteroaryl group include, but are not limited to, pyridyl, pyridyl N-oxide; pyrazinyl; pyrimidinyl; pyrazolyl; amidazolyl; oxazolyl; isoxazolyl; thiazolyl; isothiazolyl; thiadiazolyl; tetrazolyl; triazolyl; thienyl; furyl; pyranyl; pyrrolyl; pyridazinyl; benzo[d]thiazolyl, bezodioxolyl, such as benzo[d][1,3]dioxolyl; benzoxazolyl, such as benzo[d]oxazolyl; imidazopyridyl, such as imidazo[1,2-a]pyridyl; triazolopyridyl, such as [1,2,4]triazolo[4,3-a]pyridyl and [1,2,4]triazolo[1,5-a]pyridyl; indazolyl, 2H-indazolyl; pyrrolopyrimidinyl, such as pyrrolo[3,4-d]pyrimidinyl, 7H-pyrrolo[2,3-d]pyrimidinyl; pyrazolopyrimidinyl, such as pyrazolo[1,5-a]pyrimidinyl; tetrazolopyridyl, such as tetrazolo[1,5-a]pyridyl; benzothienyl; benzofuryl; benzoimidazolinyl; indolyl; indolinyl; purinyl, such as 9H-purinyl and 7H-purinyl; quinolinyl, isoqoinolinyl, 1,2,3,4-tetrahydroquinolinyl and 5,6,7,8-tetrahydroisoquinolinyl.

Examples of the nitrogen-containing heteroaryl group include, but are not limited to, pyrrolyl; pyrazolyl; imidazolyl; pyridyl; pyrazinyl; pyrimidinyl, pyrimidinyl N-oxide; pyridazinyl; pyrrolopyrimidinyl, such as pyrrolo[3,4-d]pyrimidinyl, 7H-pyrrolo[2,3-d]pyrimidinyl; purinyl, such as 9H-purinyl and 7H-purinyl; quinolinyl; indolyl; and indazolyl.

"Hydroxyl" as used herein refers to the —OH radical.

"Mercapto" as used herein refers to the —SH radical.

"Oxo" as used herein refers to the =O radical.

"Carboxyl" as used herein refers to the —C(O)—OH radical.

"Cyano" as used herein refers to the —CN radical.

When the structures contain an asterisk "*" as described herein, the compounds represented by the structures are chiral compounds, i.e. the compounds are either R-configuration or S-configuration. The configuration of the compounds can be determined using a variety of analytical techniques, for example single crystal X-ray crystallography and/or optical polarimetry according to routine protocols by those of ordinary skill in the art.

The term "optional" or "optionally" as used herein means that the subsequently described substitution pattern, event, or circumstance may or may not occur, and that the description includes instances where the substitution pattern occurs and instances in which it does not. For example, "optionally substituted alkyl" encompasses both "unsubstituted alkyl" and "substituted alkyl" as defined herein. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term "substituted" or "substituted with . . . ", as used herein, means that one or more hydrogens on the designated atom or group are replaced with one or more selections from the indicated group of substituents, provided that the designated atom's normal valence is not exceeded. When a substituent is oxo (i.e., =O), then 2 hydrogens on a single atom are replaced by the oxo. Combinations of substituents and/or variables are permissible only if such combinations result in a chemically correct and stable compound. A chemically correct and stable compound is meant to imply a compound that is sufficiently robust to survive sufficient isolation from a reaction mixture to be able to identity the chemical structure of the compound, and also sufficiently robust to allow subsequent formulation as an agent having at least one practical utility.

Unless otherwise specified, substituents are named into the core structure. For example, it is to be understood that when (cycloalkyl)alkyl is listed as a possible substituent, the point of attachment of this substituent to the core structure is in the alkyl portion.

The term "substituted with one or more substituents" as used herein means that one or more hydrogens on the designated atom or group are independently replaced with one or more selections from the indicated group of substituents. In some embodiments, "substituted with one or more substituents" means that the designated atom or group is substituted with 1, 2, 3, or 4 substituents independently chosen from the indicated group of substituents.

It will be appreciated by the person of ordinary skill in the art ("POSITA") that some of the compounds of formula (I) may contain one or more chiral centers and therefore exist in two or more stereoisomers forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the POSITA that the present invention includes all the individual stereoisomers (e.g. enantiomers), racemic mixtures or partially resolved mixtures of the compounds of formula (I) and, where appropriate, the individual tautomeric forms thereof.

In other words, in some embodiments, the present invention provides compounds of various stereoisomeric purities, i.e., diastereomeric or enantiomeric purity, with various "ee" or "de." In some embodiments, the compound of formula (I) (e.g., as described herein) has an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9% ee, or any ranges between those enumerated values). In some embodiments, the compound of formula (I) (e.g., as described herein) has an enantiomeric purity of greater than 99.9% ee, extending up to 100% ee. In some embodiments, the compound of formula (I) (e.g., as described herein) has a diastereomeric purity of at least 60% de (e.g., 60%, 65%, 70%, 75%, 80%, 85%, 90%, 91%, 92%, 93%, 94%, 95%, 96%, 97%, 98%, 99%, 99.5%, 99.9% de, or any ranges between those enumerated values). In some embodiments, the compound of formula (I) (e.g., as described herein) has a diastereomeric purity of greater than 99.9% de.

The term "enantiomeric excess" or "ee" designates how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as ([a]obs/[a]max)*100, where [a]obs is the optical rotation of the mixture of enantiomers and [a]max is the optical rotation of the pure enantiomer.

The term "diastereomeric excess" or "de" designates how much of one diastereomer is present compared to the other and is defined by analogy to enantiomeric excess. Thus, for a mixture of diastereomers, D1 and D2, the percent diastereomeric excess is defined as |D1−D2|*100, where D1 and D2 are the respective mole or weight fractions of diastereomers in a mixture such that D1+D2=1.

The determination of diastereomeric and/or enantiomeric excess is possible using a variety of analytical techniques, including NMR spectroscopy, chiral column chromatography and/or optical polarimetry according to routine protocols familiar to the POSITA.

The racemates can be used as such or can be resolved into their individual isomers. The resolution can afford stereochemical pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent, individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of, for example, at least 91%, 92%, 93%, 94%, 95%, 96%, 97%, 98%, 99% or 99.5% by weight of the desired stereoisomer. Alternatively the racemates can be covalently linked to a chiral compound (auxiliary) to produce diastereomers which can be separated by chromatography or by fractional crystallization after which time the chiral auxiliary is chemically removed to afford the pure enantiomers, as is known to the POSITA.

Also provided is a pharmaceutically acceptable salt of the compound of Formula (I), such as those described below and such as a pharmaceutically acceptable salt of the specific compounds exemplified herein, and methods using such salts.

A "pharmaceutically acceptable salt" is intended to mean a salt of a free acid or base of a compound of Formula (I) that is non-toxic, biologically tolerable, or otherwise biologically suitable for administration to the subject. For examples, see, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002.

"Pharmaceutically acceptable salt" includes, but is not limited to, acid addition salts formed by the compound of formula (I) with an inorganic acid, such as hydrochloride, hydrobromide, carbonate, bicarbonate, phosphate, sulfate, sulfite, nitrate and the like; as well as with an organic acid, such as formate, acetate, malate, maleate, fumarate, tartrate, succinate, citrate, lactate, methanesulfonate, p-toluenesulfonate, 2-hydroxyethylsulfonate, benzoate, salicylate, stearate, and salts with alkane-dicarboxylic acid of formula HOOC—$(CH_2)_n$—COOH where n is 0-4, and the like. Also, "pharmaceutically acceptable salt" includes base addition salts formed by the compound of formula (I) carrying an acidic moiety with pharmaceutically acceptable cations, for example, sodium, potassium, calcium, aluminum, lithium, and ammonium. The molar ratio of the compound of formula (I) to the acid or the cation in the obtained pharmaceutically acceptable salt includes, but is not limited to, 1:1, 1:2, 1:3, and 1:4.

In addition, if a compound described herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts.

The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrates, for example, hemihydrates, monohydrate, and dihydrate, as well as variable hydrates.

As used herein, the terms "group", "radical" and "moiety" are synonymous and are intended to indicate functional groups or fragments of molecules attachable to other fragments of molecules.

The term "active ingredient" is used to indicate a chemical substance which has biological activity. In some embodiments, an "active ingredient" is a chemical substance having pharmaceutical utility. Practical pharmaceutical activity in the United States can be established by appropriate pre-clinical assays, whether in vitro or in vivo. Pharmaceutical activity sufficient to be accepted by a regulatory agency, such as FDA in the U.S., is a higher standard than the pre-clinical assay. Such a higher standard of pharmaceutical activity, the success of which cannot generally be reasonably expected from the pre-clinical results, can be established by appropriate and successful randomized, double blind, controlled clinical trials in humans.

The terms "treating", "treat," or "treatment" of a disease or disorder, in the context of achieving therapeutic benefit, refer to administering one or more pharmaceutical substances, especially a compound of formula (I) and/or a pharmaceutically acceptable salt thereof described herein to a subject, such as a human subject, that has the disease or disorder, or has a symptom of a disease or disorder, or has a predisposition toward a disease or disorder, with the purpose to cure, heal, alleviate, relieve, alter, remedy, ameliorate, improve, or affect the disease or disorder, the symptoms of the disease or disorder, or the predisposition toward the disease or disorder. In some embodiments, the disease or disorder is cancer.

The terms "treating", "contacting" and "reacting," in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount or dose of a PI$_3$K-inhibiting agent sufficient to generally bring about a therapeutic benefit in patients in need of treatment for a disease or disorder mediated by PI$_3$K activity. Effective amounts or doses of the active ingredient of the present disclosure may be ascertained by methods such as modeling, dose escalation studies or clinical trials, and by taking into consideration factors, e.g., the mode or route of administration or drug delivery, the pharmacokinetics of the agent, the severity and course of the disease or disorder, the subject's previous or ongoing therapy, the subject's health status and response to drugs, and the judgment of the treating physician. That said, ascertaining an effective dose is not generally predictable in the United States from pre-clinical experimentation. In fact, dosages can be sufficiently unpredictable that new, unpredictable dosage regimes are developed after dosages originally used in randomized, double blind, controlled, clinical trials.

An exemplary dose is in the range of from about 0.0001 to about 200 mg of active agent per kg of subject's body weight per day, such as from about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease or disorder has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

The term "inhibition" or "inhibiting" indicates a decrease in the baseline activity of a biological activity or process. The term "inhibition of PI$_3$K activity" is a practical pharmaceutical activity for purposes of this disclosure and refers to a decrease in the activity of PI$_3$K as a direct or indirect response to the presence of the compound of formula (I) and/or the pharmaceutically acceptable salt thereof described herein, relative to the activity of PI$_3$K in the absence of the compound of formula (I) and/or the pharmaceutically acceptable salt thereof. The decrease in activity may be due to the direct interaction of the compound of formula (I) and/or the pharmaceutically acceptable salt thereof described herein with PI$_3$K, or due to the interaction of the compound of formula (I) and/or the pharmaceutically acceptable salt thereof described herein, with one or more other factors that in turn affect the PI$_3$K activity. For example, the presence of the compound of formula (I) and/or the pharmaceutically acceptable salt thereof described herein, may decrease the PI$_3$K activity by directly binding to the PI$_3$K, by causing (directly or indirectly) another factor to decrease the PI$_3$K activity, or by (directly or indirectly) decreasing the amount of PI$_3$K present in the cell or organism.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

In general, the term "about" is used herein to modify a numerical value above and below the stated value by a variance of 20%.

Technical and scientific terms used herein and not specifically defined have the meaning commonly understood by the POSITA to which the present disclosure pertains.

One embodiment of the disclosure provides a compound of formula (I):

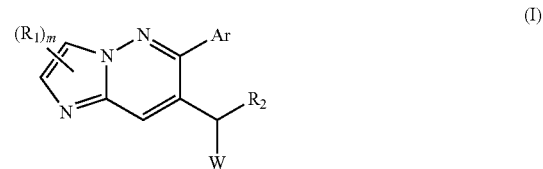

and/or a pharmaceutically acceptable salt thereof, and/or solvates, racemic mixtures, enantiomers, diasteromers, and tautomers thereof, wherein Ar is aryl or heteroaryl, each of which is optionally substituted with one or more groups chosen from deuterium, halo, —CN, —OH, —SH, $C_{1-6}$ alkyl, alkenyl, $C_{2-6}$ alkynyl, $C_{1-6}$ haloalkyl, —O($C_{1-6}$ alkyl), —($C_{1-6}$ alkyl)OH, —NH$_2$, —NH($C_{1-6}$ alkyl), —N($C_{1-6}$ alkyl)($C_{1-6}$ alkyl), and —S(O)$_2$($C_{1-6}$ alkyl);

W is chosen from heteroaryl and —N(R$_3$)heteroaryl, wherein said heteroaryl is optionally substituted with one or more groups chosen from halo, —CN, —OH, —SH, $C_{1-6}$ alkyl, $C_{2-6}$ alkenyl, $C_{2-6}$ alkynyl, $C_{1-6}$ haloalkyl, —O($C_{1-6}$ alkyl), —($C_{1-6}$ alkyl)OH, —NH$_2$, —NH($C_{1-6}$ alkyl), —N($C_{1-6}$ alkyl)($C_{1-6}$ alkyl), —COOH, —C(O)NH$_2$, —C(O)NH($C_{1-6}$ alkyl), —C(O)N($C_{1-6}$ alkyl)($C_{1-6}$ alkyl), —SO$_2$($C_{1-6}$ alkyl), phenyl, and 5- or 6-membered heteroaryl; in which each of said phenyl or 5- or 6-membered heteroaryl as the substituent of W is optionally substituted with one or more groups chosen from halo, —CN, —OH, —SH, $C_{1-6}$ alkyl, $C_{1-6}$ haloalkyl, —O($C_{1-6}$ alkyl), —($C_{1-6}$ alkyl)OH, —NH$_2$, —NH($C_{1-6}$ alkyl), and —N($C_{1-6}$ alkyl)($C_{1-6}$ alkyl);

R$_1$ is independently chosen from H, halo, —CN, $C_{1-6}$ alkyl, $C_{1-6}$ haloalkyl, —($C_{1-6}$ alkyl)OH, —($C_{1-6}$ alkyl)O($C_{1-6}$ alkyl), and $C_{2-6}$ alkynyl;

R$_2$ is chosen from H, $C_{1-6}$ alkyl, and $C_{3-8}$ cycloalkyl, each of which except for H, is optionally substituted with one or more groups chosen from halo, —CN, $C_{1-6}$ alkyl, $C_{1-6}$ haloalkyl, and —OH;

R$_3$ is H or $C_{1-6}$ alkyl;

m is 1 or 2.

In some embodiments of the compound of formula (I), wherein W is chosen from nitrogen-containing heteroaryl or —N(R$_3$) nitrogen-containing heteroaryl, wherein said nitrogen-containing heteroaryl is optionally substituted with one or more groups chosen from halo, —CN, —OH, —SH, C$_{1-6}$ alkyl, C$_{1-6}$ haloalkyl, —O(C$_{1-6}$ alkyl), —(C$_{1-6}$ alkyl)OH, —NH$_2$, —NH(C$_{1-6}$ alkyl), —N(C$_{1-6}$ alkyl)(C$_{1-6}$ alkyl), —COOH, —C(O)NH$_2$, —C(O)NH(C$_{1-6}$ alkyl), —C(O)N(C$_{1-6}$ alkyl)(C$_{1-6}$ alkyl), —SO$_2$(C$_{1-6}$ alkyl), phenyl, and 5- or 6-membered heteroaryl; in which each of said phenyl or 5- or 6-membered heteroaryl as the substituent of W is optionally substituted with one or more groups chosen from halo, —CN, —OH, —SH, C$_{1-6}$ alkyl, C$_{1-6}$ haloalkyl, —O(C$_{1-6}$ alkyl), —(C$_{1-6}$ alkyl)OH, —NH$_2$, —NH(C$_{1-6}$ alkyl), and —N(C$_{1-6}$ alkyl)C$_{1-6}$ alkyl).

In some embodiments of the compound of formula (I), wherein, W is chosen from nitrogen-containing heteroaryl or —N(R$_3$) nitrogen-containing heteroaryl, wherein said nitrogen-containing heteroaryl is optionally substituted with one or more groups chosen from fluoro, chloro, bromo, —CN, —OH, —SH, C$_{1-6}$ alkyl, C$_{1-6}$ haloalkyl, —NH$_2$, —NH(C$_{1-6}$ alkyl), —N(C$_{1-6}$ alkyl)(C$_{1-6}$ alkyl), —COOH, —C(O)NH$_2$, phenyl, and 5- or 6-membered heteroaryl; in which each of said phenyl or 5- or 6-membered heteroaryl as the substituent of W is optionally substituted with one or more groups chosen from halo, —OH, C$_{1-6}$ alkyl, and —O(C$_{1-6}$ alkyl).

In some embodiments of the compound of formula (I), said nitrogen-containing heteroaryl is pyrimidinyl, pyrrolopyrimidinyl, and purinyl.

In some embodiments of the compound of formula (I), W is chosen from

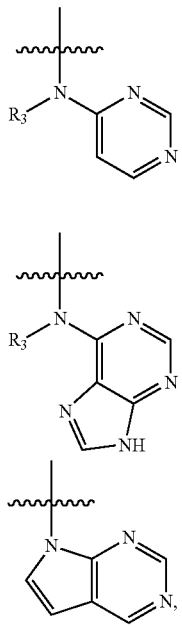

each of which is optionally substituted with one or more groups chosen from fluoro, chloro, bromo, —CN, —OH, —SH, C$_{1-6}$ alkyl, C$_{1-6}$ haloalkyl, —NH$_2$, —NH(C$_{1-6}$ alkyl), —N(C$_{1-6}$ alkyl)(C$_{1-6}$ alkyl), —COOH, —C(O)NH$_2$, —C(O)NH(C$_{1-6}$ alkyl), phenyl, and 5- or 6-membered heteroaryl; in which each of said phenyl or 5- or 6-membered heteroaryl as the substituent of W is optionally substituted with one or more groups chosen from halo, —CN, —OH, —SH, C$_{1-6}$ alkyl, C$_{1-6}$ haloalkyl, —O(C$_{1-6}$ alkyl), —(C$_{1-6}$ alkyl)OH, —NH$_2$, —NH(C$_{1-6}$ alkyl), and —N(C$_{1-6}$ alkyl)(C$_{1-6}$ alkyl).

In some embodiments of the compound of formula (I), W is

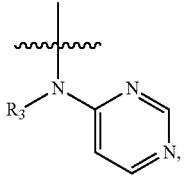

which is optionally substituted with one or more groups chosen from fluoro, chloro, bromo, —CN, —OH, —SH, C$_{1-6}$ alkyl, C$_{1-6}$ haloalkyl, —NH$_2$, —NH(C$_{1-6}$ alkyl), —N(C$_{1-6}$ alkyl)(C$_{1-6}$ alkyl), —COOH, —C(O)NH$_2$, phenyl, and 5- or 6-membered heteroaryl; in which each of said phenyl or 5- or 6-membered heteroaryl as the substituent of W is optionally substituted with one or more groups chosen from halo, —OH, C$_{1-6}$ alkyl, and —O(C$_{1-6}$ alkyl).

In some embodiments of the compound of formula (I), W is chosen from

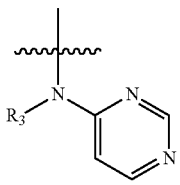 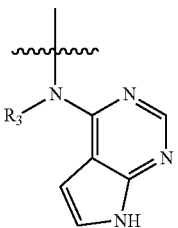

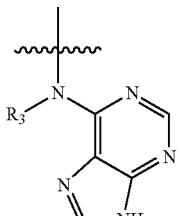 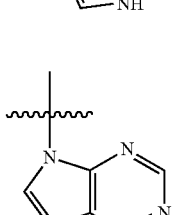

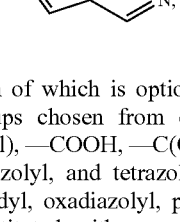

each of which is optionally substituted with one or more groups chosen from chloro, —CN, —NH$_2$, —NH(C$_{1-6}$ alkyl), —COOH, —C(O)NH$_2$, phenyl, pyridyl, oxadiazolyl, pyrazolyl, and tetrazolyl; in which each of said phenyl, pyridyl, oxadiazolyl, pyrazolyl, or tetrazolyl is optionally substituted with one or more groups chosen from halo, —OH, C$_{1-6}$ alkyl, and —O(C$_{1-6}$ alkyl).

In some embodiments of the compound of formula (I), W is

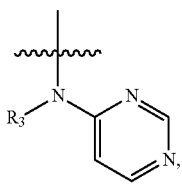

which is optionally substituted with one or more groups chosen from chloro, —CN, —NH$_2$, NH(C$_{1-6}$ alkyl), —COOH, —C(O)NH$_2$, phenyl, pyridyl, oxadiazolyl, pyrazolyl and tetrazolyl; in which each of said phenyl, pyridyl, oxadiazolyl, pyrazolyl, or tetrazolyl is optionally substituted with one or more groups chosen from halo, —OH, C$_{1-6}$ alkyl, and —O(C$_{1-6}$ alkyl).

In some embodiments of the compound of formula (I), Ar is chosen from phenyl, naphthyl, pyridyl, pyrazolyl, quinolyl, thienyl, benzothiazolyl, indolyl, and 2,3-dihydro-1,4-benzodioxinyl, each of which is optionally substituted with one or more groups chosen from deuterium, halo, —CN, C$_{1-6}$ alkyl, —(C$_{1-6}$ alkyl)OH, C$_{1-6}$ haloalkyl, or —S(O)$_2$(C$_{1-6}$ alkyl).

In some embodiments of the compound of formula (I), Ar is phenyl or pyridyl, each of which is optionally substituted with one or more groups chosen from halo, —CN, and C$_{1-6}$ haloalkyl.

In some embodiments of the compound of formula (I), Ar is phenyl or pyridyl, each of which is optionally substituted with one or more halo, such as is optionally substituted with one or more fluoro.

In some embodiments of the compound of formula (I), R$_1$ is independently chosen from H, halo, —CN, and C$_{1-6}$ alkyl.

In some embodiments of the compound of formula (I), R$_2$ is C$_{1-6}$ alkyl, such as C$_{1-4}$ alkyl, further such as methyl and ethyl.

In some embodiments of the compound of formula (I), R$_3$ is H.

In some embodiments of the compound of formula (I), m is 1.

In some embodiments of the compound of formula (I), formula (I) is formula (I-1), (I-1)

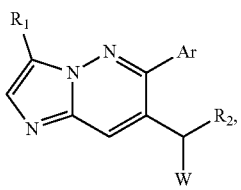

In some embodiments of the compound of formula (I-1), W is chosen from nitrogen-containing heteroaryl or —N(R$_3$) nitrogen-containing heteroaryl, wherein said nitrogen-containing heteroaryl is optionally substituted with one or more groups chosen from fluoro, chloro, bromo, —CN, —OH, —SH, C$_{1-6}$ alkyl, C$_{1-6}$ haloalkyl, —NH$_2$, —NH(C$_{1-6}$ alkyl), —N(C$_{1-6}$ alkyl)(C$_{1-6}$ alkyl), phenyl, and 5- or 6-membered heteroaryl.

In some embodiments of the compound of formula (I-1), said nitrogen-containing heteroaryl is chosen from pyrimidinyl, pyrrolopyrimidinyl, and purinyl.

In some embodiments of the compound of formula (I-1), W is chosen from

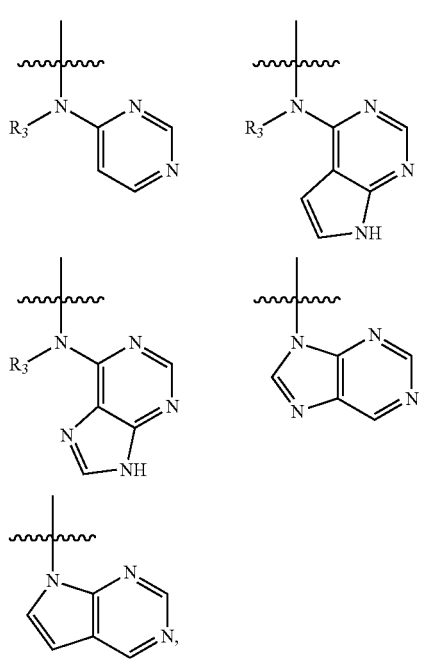

each of which is optionally substituted with one or more groups chosen from fluoro, chloro, bromo, —CN, —OH, —SH, C$_{1-6}$ alkyl, C$_{1-6}$ haloalkyl, —NH$_2$, —NH(C$_{1-6}$ alkyl), —N(C$_{1-6}$ alkyl)(C$_{1-6}$ alkyl), phenyl, and 5- or 6-membered heteroaryl.

In some embodiments of the compound of formula (I-1), W is chosen from

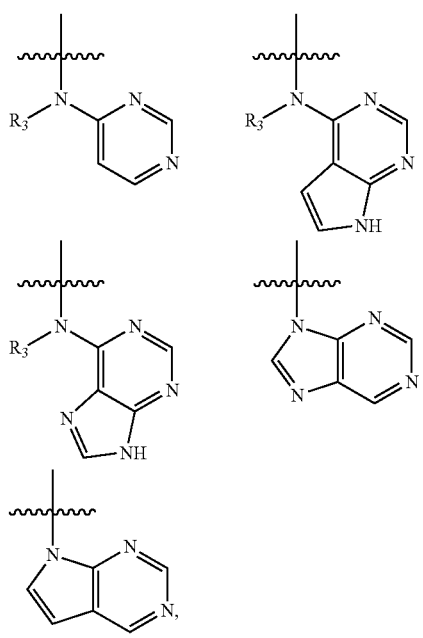

each of which is optionally substituted with one or more groups chosen from —CN, —NH$_2$, and tetrazolyl.

In some embodiments of the compound of formula (I-1), W is

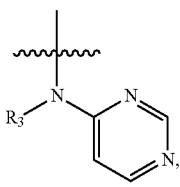

which is optionally substituted with one or more groups chosen from fluoro, chloro, bromo, —CN, —OH, —SH, $C_{1-6}$ alkyl, $C_{1-6}$ haloalkyl, —$NH_2$, —$NH(C_{1-6}$ alkyl), —$N(C_{1-6}$ alkyl)($C_{1-6}$ alkyl), phenyl, and 5- or 6-membered heteroaryl.

In some embodiments of the compound of formula (I-1), W is

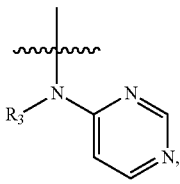

which is optionally substituted with one or more groups chosen from —CN, —$NH_2$, and tetrazolyl.

In some embodiments of the compound of formula (I-1), Ar is chosen from phenyl, naphthyl, pyridyl, pyrazolyl, quinolyl, thienyl, benzothiazolyl, each of which is optionally substituted with one or more groups chosen from halo, —CN, $C_{1-6}$ alkyl, —($C_{1-6}$ alkyl)OH, and $C_{1-8}$ haloalkyl.

Also provided is a compound chosen from Compounds 1-9 and 11-82, as numbered in the experimental section, and/or a pharmaceutically acceptable salt thereof.

In another aspect, provided is a pharmaceutical composition, comprising a compound of formula (I) (e.g., any of the compounds described herein) and/or a pharmaceutically acceptable salt thereof and at least one pharmaceutically acceptable excipient (e.g., a pharmaceutically acceptable carrier).

In another aspect, provided is a method of in vivo or in vitro inhibiting the activity of $PI_3K$, comprising contacting the $PI_3K$ with an effective amount of a compound of formula (I) (e.g., any of the compounds described herein) and/or a pharmaceutically acceptable salt thereof.

In another aspect, provided is a method of to vivo or in vitro inhibiting the activity of $PI_3K$, comprising contacting the $PI_3K$ with an amount of a pharmaceutical composition comprising a compound of formula (I) (e.g., any of the compounds described herein) and/or a pharmaceutically acceptable salt thereof and at least one pharmaceutically acceptable excipient (e.g., a pharmaceutically acceptable carrier) effective to inhibit the activity of $PI_3K$.

In another aspect, provided is a method of treating a disease responsive to inhibition of $PI_3K$ in a subject, comprising administering to the subject in need thereof an amount of a compound of formula (I) (e.g., any of the compounds described herein) and/or a pharmaceutically acceptable salt thereof effective to inhibit $PI_3K$ in said subject.

In another aspect, provided is a method of treating a disease responsive to inhibition of $PI_3K$ in a subject, comprising administering to the subject in need thereof an amount of a pharmaceutical composition comprising a compound of formula (I) (e.g., any of the compounds described herein) and/or a pharmaceutically acceptable salt thereof and at least one pharmaceutically acceptable excipient (e.g., a pharmaceutically acceptable carrier) effective to inhibit $PI_3K$ in said subject.

In another aspect, provided is a use of a compound of formula (I) (e.g., any of the compounds described herein) and/or a pharmaceutically acceptable salt thereof described herein for treating a disease responsive to inhibition of $PI_3K$ by inhibiting said $PI_3K$ in said subject.

In another aspect, provided is a use of a compound of formula (I) (e.g., any of the compounds described herein) and/or a pharmaceutically acceptable salt thereof described herein in the manufacture of a medicament for treating a disease responsive to inhibition of $PI_3K$.

In some embodiments, said disease responsive to inhibition of $PI_3K$ is an inflammatory disease, an autoimmune disease, or a cancer.

In some embodiments, said inflammatory disease or autoimmune disease is chosen from rheumatoid arthritis, chronic obstructive pulmonary disease (COPD), allergic rhinitis, asthma, lupus, systemic lupus erythematosus, psoriasis, and multiple sclerosis.

In some embodiments, said cancer is a solid tumor or hematological malignancy chosen from leukemia, multiple myeloma (MM), and lymphoma.

In some embodiments, said leukemia is chosen from acute lymphocytic leukemia (ALL), acute myeloid leukemia (AML), chronic lymphocytic leukemia (CLL), and chronic myelogenous leukemia (CML).

In some embodiments, said lymphoma is chosen from Hodgkin's lymphoma, non-Hodgkin's lymphoma (NHL), mantle cell lymphoma (MCL), follicular lymphoma, B-cell lymphoma, T-cell lymphoma, and diffuse large B-cell lymphoma (DLBCL).

In another aspect, provided is a compound of formula (II) and/or a salt thereof, and/or a racemic mixture or enantiomer thereof, which can be used in the manufacture of compounds of formula (I) (e.g., any of the compounds described herein),

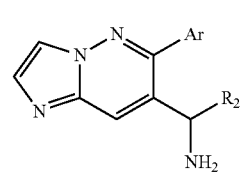

(II)

wherein, Ar and $R_2$ are defined as in the compound of formula (I).

In some embodiments, the compound of formula (II) and/or a salt thereof is chosen from:

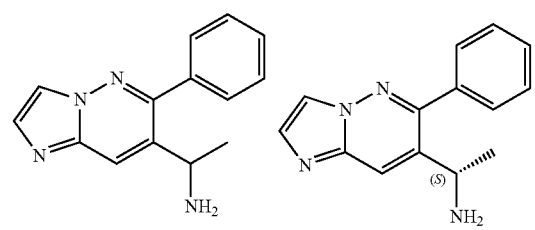

-continued
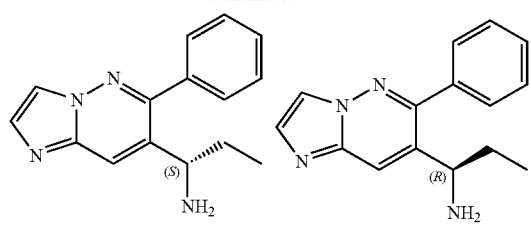
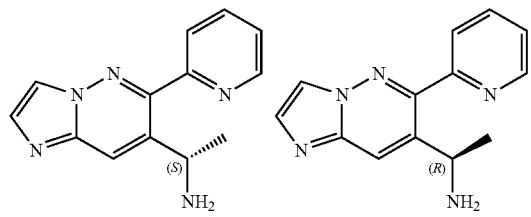
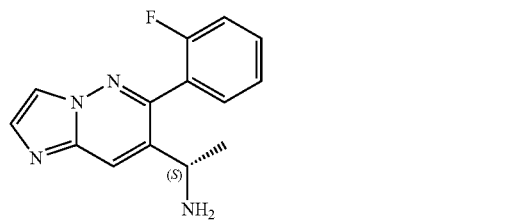
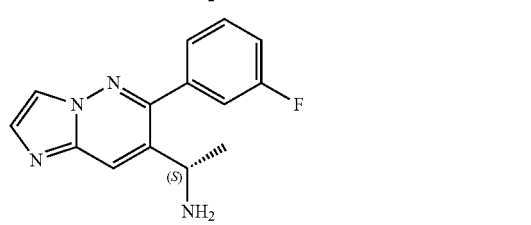
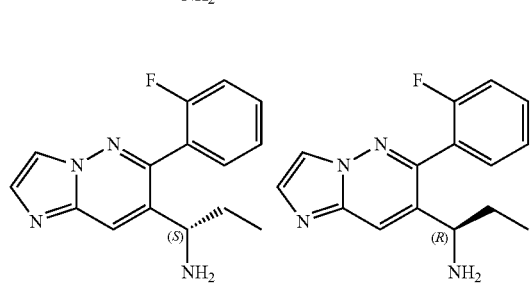
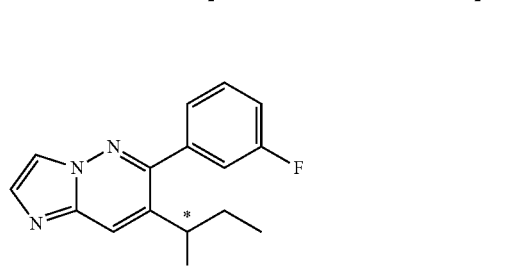
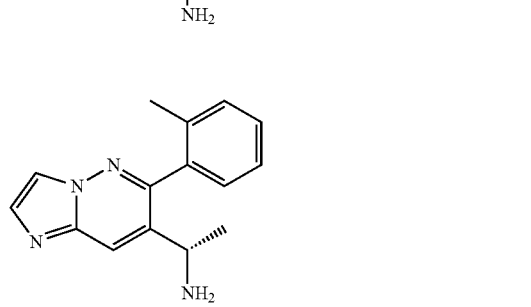
-continued
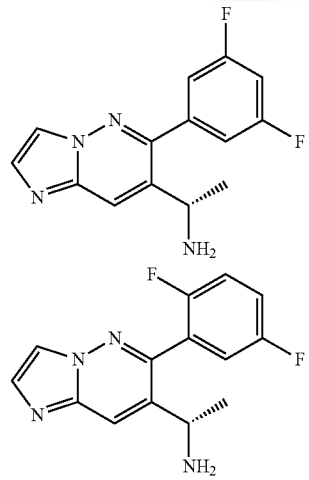
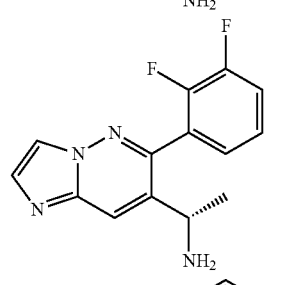
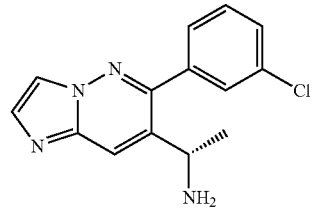
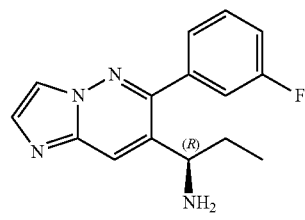
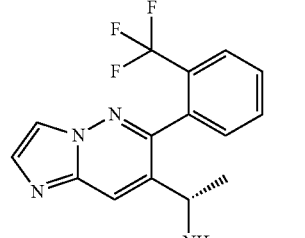
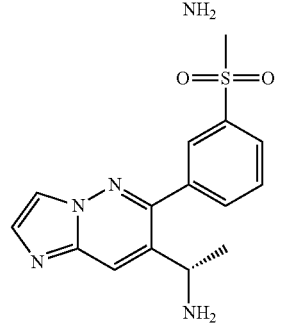

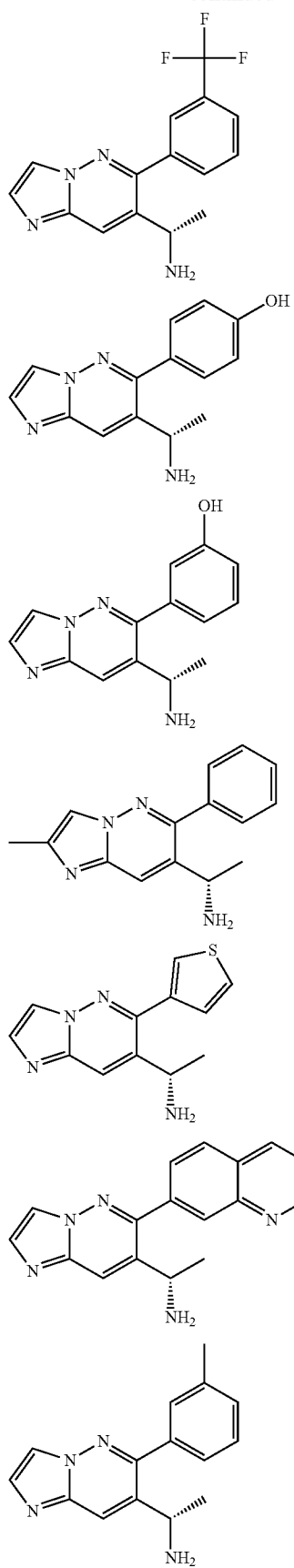
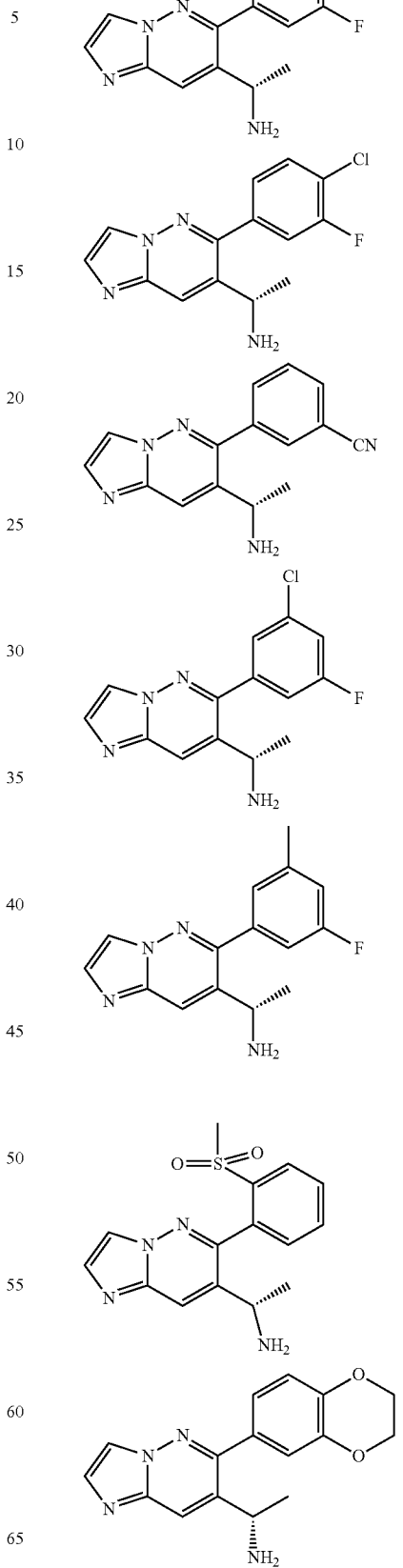

-continued

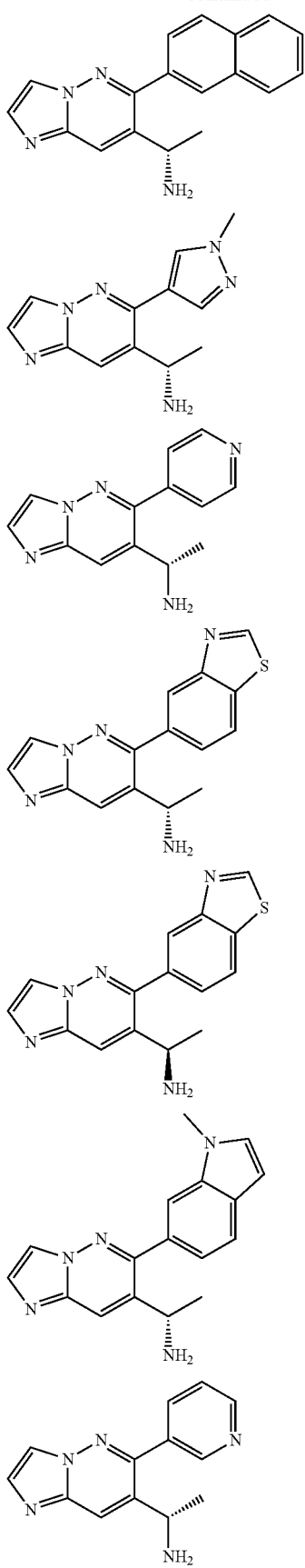

-continued

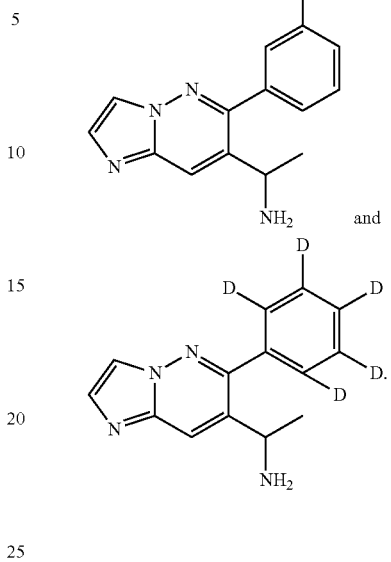 and

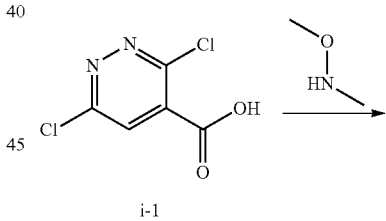

General Synthetic Methods for Disclosed Embodiments

The compound of formula (I) described herein and/or a pharmaceutically acceptable salt thereof described herein can be synthesized from commercially available starting material by methods well known in the art, taken together with the disclosure in this patent application. The following schemes illustrate general methods for preparation of some of the compounds disclosed herein.

Scheme I

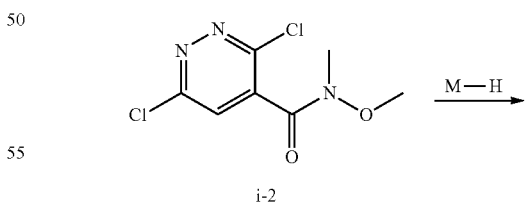

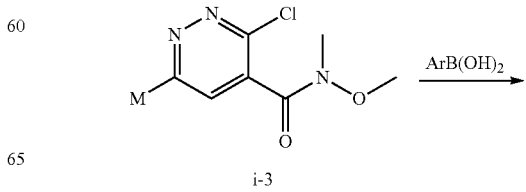

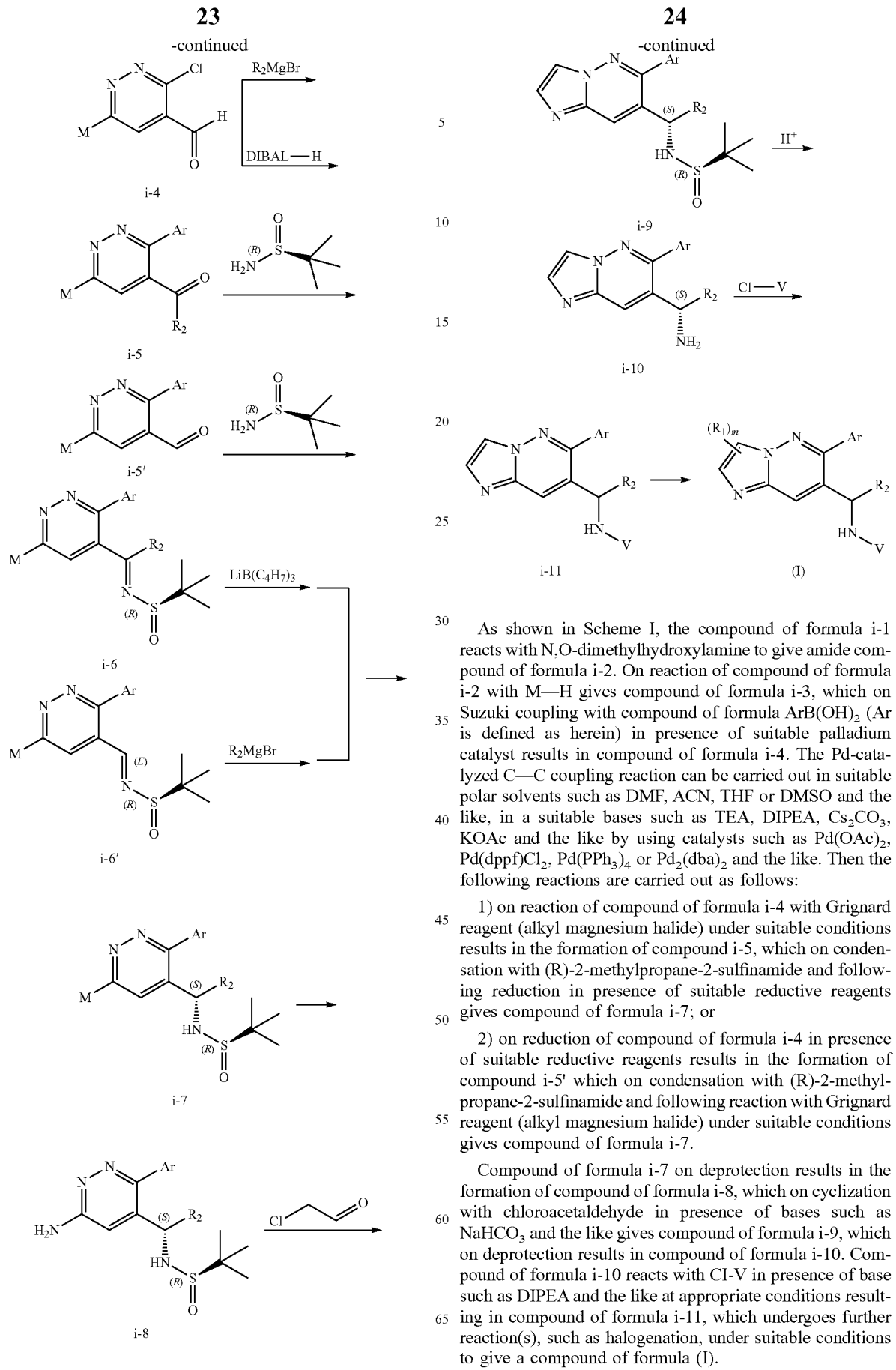

As shown in Scheme I, the compound of formula i-1 reacts with N,O-dimethylhydroxylamine to give amide compound of formula i-2. On reaction of compound of formula i-2 with M—H gives compound of formula i-3, which on Suzuki coupling with compound of formula $ArB(OH)_2$ (Ar is defined as herein) in presence of suitable palladium catalyst results in compound of formula i-4. The Pd-catalyzed C—C coupling reaction can be carried out in suitable polar solvents such as DMF, ACN, THF or DMSO and the like, in a suitable bases such as TEA, DIPEA, $Cs_2CO_3$, KOAc and the like by using catalysts such as $Pd(OAc)_2$, $Pd(dppf)Cl_2$, $Pd(PPh_3)_4$ or $Pd_2(dba)_2$ and the like. Then the following reactions are carried out as follows:

1) on reaction of compound of formula i-4 with Grignard reagent (alkyl magnesium halide) under suitable conditions results in the formation of compound i-5, which on condensation with (R)-2-methylpropane-2-sulfinamide and following reduction in presence of suitable reductive reagents gives compound of formula i-7; or 2) on reduction of compound of formula i-4 in presence of suitable reductive reagents results in the formation of compound i-5' which on condensation with (R)-2-methylpropane-2-sulfinamide and following reaction with Grignard reagent (alkyl magnesium halide) under suitable conditions gives compound of formula i-7.

Compound of formula i-7 on deprotection results in the formation of compound of formula i-8, which on cyclization with chloroacetaldehyde in presence of bases such as $NaHCO_3$ and the like gives compound of formula i-9, which on deprotection results in compound of formula i-10. Compound of formula i-10 reacts with Cl-V in presence of base such as DIPEA and the like at appropriate conditions resulting in compound of formula i-11, which undergoes further reaction(s), such as halogenation, under suitable conditions to give a compound of formula (I).

Scheme II

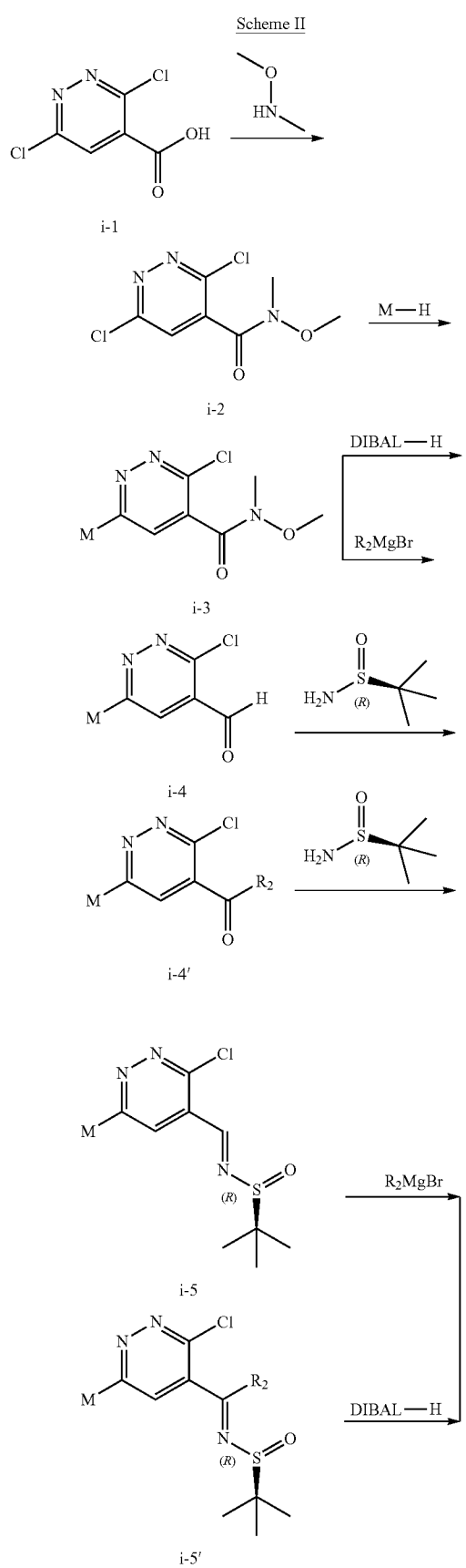

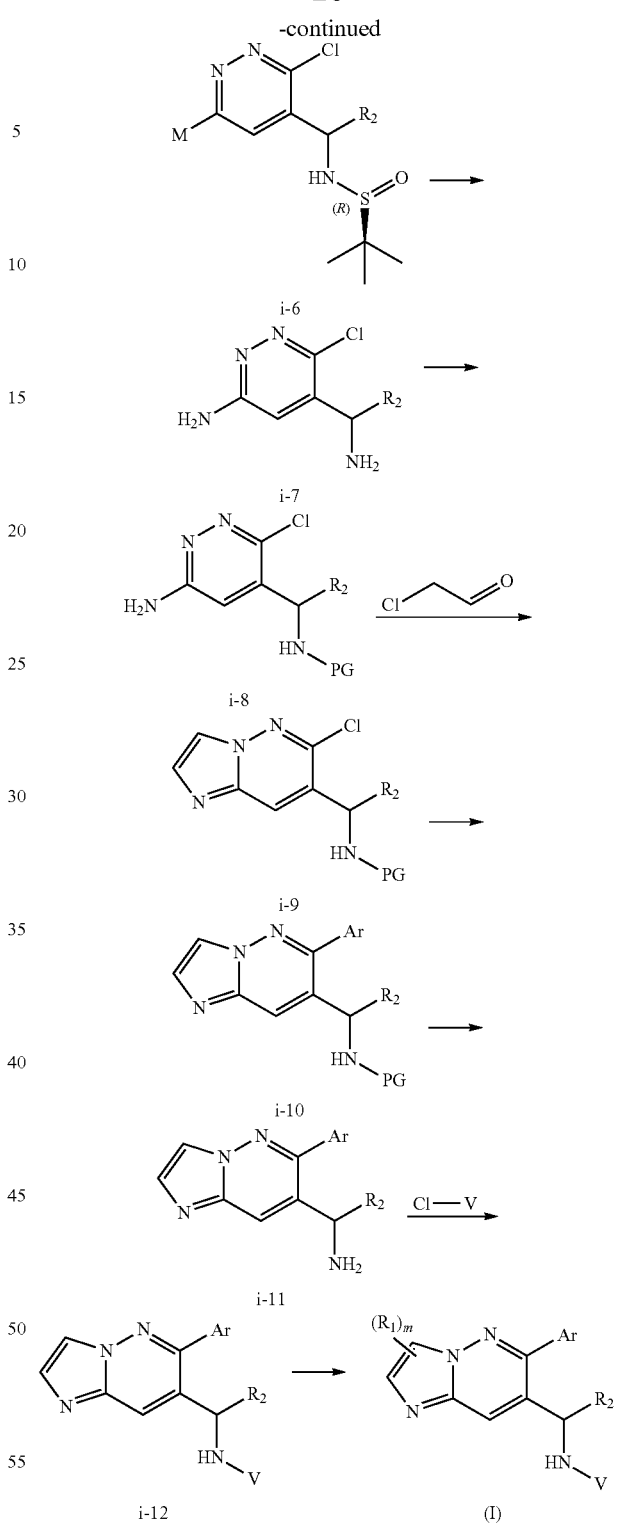

As shown in Scheme II, the compound of formula i-1 reacts with N,O-dimethylhydroxylamine to give amide compound of formula i-2. On reaction of compound of formula i-2 with M—H gives compound of formula i-3. Then the following reactions are carried out as follows:

1) on reduction of compound of formula i-3 in presence of suitable reductive reagents results in the formation of compound i-4, which on condensation with (R)-2-methylpropane-2-sulfinamide and following reaction with Grignard reagent (alkyl magnesium halide) under suitable conditions gives compound of formula i-6; or 2) on reaction of compound of formula i-3 with Grignard reagent (alkyl magnesium halide) under suitable conditions results in the formation of compound i-4', which on condensation with (R)-2-methylpropane-2-sulfinamide and following reduction in presence of suitable reductive reagents gives compound of formula i-6.

Compound of formula i-6 on deprotection and protection gives compound of formula i-8, which on cyclization with chloroacetaldehyde in presence of bases such as $NaHCO_3$ and the like gives compound of formula i-9. Compound of formula i-9 on Stille coupling or Suzuki coupling with stannanes or $ArB(OH)_2$ (Ar is defined as herein) in presence of suitable palladium catalyst such as $Pd_2(dba)_3$ and the like, suitable ligands such X-phos and the like, under standard Stille coupling or Suzuki coupling condition gives compound of formula i-10, which on deprotection gives i-11. Compound of formula i-11 reacts with CI-V in presence of base such as DIPEA and the like at appropriate conditions resulting in compound of formula i-12, which undergoes further reaction(s), such as halogenation under suitable conditions, to give compound of formula (I).

The compounds thus obtained can be further modified at their peripheral positions to provide the desired compounds. Synthetic chemistry transformations are described, for example, in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*. John Wiley and Sons (1995) and subsequent editions thereof.

Before use, the compound of formula (I) and/or a pharmaceutically acceptable salt thereof described herein can be purified by column chromatography, high performance liquid chromatography, crystallization or other suitable methods.

Pharmaceutical Compositions and Practical Utility

The compound of formula (I) (e.g., any of those described herein) and/or a pharmaceutically acceptable salt thereof described herein is used, alone or in combination with one or more additional active ingredients, to formulate pharmaceutical compositions. A pharmaceutical composition comprises: (a) an effective amount of a compound of formula (I) and/or a pharmaceutically acceptable salt thereof described herein; and (b) a pharmaceutically acceptable excipient (e.g., a pharmaceutically acceptable carrier).

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compound of formula (I) and/or a pharmaceutically acceptable salt thereof described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in Remington's Pharmaceutical Sciences, A. Osol, a standard reference text in the art.

A pharmaceutical composition comprising a compound of formula (I) (e.g., any of those described herein) and/or a pharmaceutically acceptable salt thereof described herein can be administered in various known manners, such as orally, topically, racially, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A pharmaceutical composition described herein can be prepared in the form of tablet, capsule, sachet, dragee, powder, granule, lozenge, powder for reconstitution, liquid preparation, or suppository. In some embodiments, a pharmaceutical composition comprising a compound of formula (I) and/or a pharmaceutically acceptable salt thereof is formulated for intravenous infusion, topical administration, or oral administration.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In some embodiments, the compound of formula (I) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a tablet. In some embodiments, the compound of formula (I) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

A sterile injectable composition (e.g., aqueous or oleaginous suspension) can be formulated according to techniques known in the art using suitable dispersing or wetting agents (such as, for example, Tween 80) and suspending agents. The sterile injectable intermediate can also be a sterile injectable solution or suspension in a non-toxic parenteral acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the Intermediate of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, it desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

Suitable in vitro assays can be used to evaluate the practical utility of the compound of formula (I) and/or a pharmaceutically acceptable salt thereof described herein, in inhibiting the activity of $PI_3K$. The compound of formula (I) and/or a pharmaceutically acceptable salt thereof described herein can further be examined for additional practical utility in treating cancer or autoimmune disease by in vivo assays. For example, the compound of formula (I) and/or a pharmaceutically acceptable salt thereof described herein can be administered to an animal (e.g., a mouse model) having cancer or autoimmune disease and its therapeutic effects can be accessed. Assuming the pre-clinical results are successful, a dosage range and administration route for animals, such as humans, can be projected.

The compound of formula (I) (e.g., any of those described herein) and/or a pharmaceutically acceptable salt thereof described herein can be shown to have sufficient pre-clinical practical utility to merit clinical trials hoped to demonstrate a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's lymphoma; non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), refractory anemia with excess blasts (RAEB), and RAEB in transformation (RAEB-T); and myeloproliferative syndromes.

In some embodiment, exemplary hematologic malignancies include leukemia, such as acute lymphocytic leukemia (ALL), acute myeloid leukemia (AML), chronic lymphocytic leukemia (CLL), and chronic myelogenous leukemia (CML); multiple myeloma (MM); and lymphoma, such as Hodgkin's lymphoma, non-Hodgkin's lymphoma (NHL), mantle cell lymphoma (MCL), follicular lymphoma, B-cell lymphoma, T-cell lymphoma, and diffuse large B-cell lymphoma (DLBCL).

The term "inflammatory disease" refers to pathological states resulting in inflammation, typically caused by neutrophil chemotaxis. Examples of such diseases include inflammatory skin diseases including psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc. The preferred indications include, without limitation, chronic inflammation, autoimmune diabetes, rheumatoid arthritis (RA), rheumatoid spondylitis, gouty arthritis and other arthritic conditions, multiple sclerosis (MS), asthma, systemic lupus erythematosus, adult respiratory distress syndrome, Behcet's disease, psoriasis, chronic pulmonary inflammatory disease, graft versus host reaction, Crohn's Disease, ulcerative colitis, inflammatory bowel disease (IBD), Alzheimer's disease, and pyresis.

The compound of formula (I) and/or a pharmaceutically acceptable salt described herein can be used to achieve a beneficial therapeutic or prophylactic effect, for example, in subjects with an autoimmune disease.

The term "autoimmune disease" refers to a disease or disorder arising from and/or directed against an individual's own tissues or organs, or a co-segregate or manifestation thereof, or resulting condition therefrom. Examples of autoimmune diseases include, but are not limited to, COPD (chronic obstructive pulmonary disease), allergic rhinitis, lupus, myasthenia gravis, multiple sclerosis (MS), rheumatoid arthritis (RA), psoriasis, inflammatory bowel disease (IBD), asthma and idiopathic thrombocytopenic purpura, and myeloid proliferative disorder, such as myelofibrosis, PV/ET (Post-Polycythemia/Essential Thrombocythemia Myelofibrosis).

In some embodiments, the inflammatory disease and autoimmune disease include rheumatoid arthritis, chronic obstructive pulmonary disease (COPD), allergic rhinitis, asthma, lupus, systemic lupus erythematosus, psoriasis, and multiple sclerosis.

In addition, the compound of formula (I) (e.g., any of those described herein) and/or a pharmaceutically acceptable salt thereof described herein may be used in combination with additional active ingredients in the treatment of cancer, inflammatory or autoimmune disease. The additional active ingredients may be coadministered separately with the compound of formula (I) and/or a pharmaceutically acceptable salt thereof described herein or included with such an ingredient in a pharmaceutical composition according to the disclosure, such as a fixed-dose combination drug product. In an exemplary embodiment, additional active ingredients are those that are known or discovered to be effective in the treatment of diseases mediated by PI$_3$K activity, such as another PI$_3$K modulator or a compound active against another target associated with the particular disease. The combination may serve to increase efficacy (e.g., by including in the combination a compound potentiating the potency or effectiveness of the compound of formula (I) and/or a pharmaceutically acceptable salt thereof described herein), decrease one or more side effects, or decrease the required dose of the compound of formula (I) and/or a pharmaceutically acceptable salt thereof described herein.

EXAMPLES

The examples below are intended to be exemplary and should not be considered to be limiting in any way. Unless indicated otherwise, parts are parts by weight, temperature is in degrees of Centigrade, and pressure is at or near atmospheric. All MS data were obtained by Agilent 6120 and/or Agilent 1100. All reagents, except intermediates, used in this disclosure are commercially available. All compound names except the reagents were generated by Chemdraw 12.0.

In the following examples, the abbreviations below are used:
ACN Acetonitrile
Boc tert-butoxycarbonyl
Boc$_2$O di-t-butyl-dicarbonate
DAST Diethylaminosulfur trifluoride
DCM dichloromethane
DEA diethylamine
DMF N,N-dimethylformamide
DMA Dimethylacetamide
DIBAL-H Diisobutylaluminium hydride
DIPEA N,N-Diisopropylethylamine
EDCl 1-(3-dimethylaminopropyl)-3-ethylcarbodiimide hydrochloride
EtOAc/EA ethyl acetate
Et$_3$N triethylamine
HATU O-(7-azabenzotriazol-1-yl)-N,N,N',N'-tetra-methyl-uronium hexafluorophosphate
HBTU O-Benzotriazole-N,N,N',N'-tetramethyl-uronium-hexafluoro-phosphate
HOAc acetic acid
HOBT 1-hydroxybenzotriazole
ee enantiomeric excess
mL milliliter(s)
g gram(s)
mg milligram(s)
ng nanogram(s)
mol mole(s)
mmol millimole(s)
min minute(s)
h hour(s)
mCPBA 3-Chloroperoxybenzoic acid
MeOH methanol
NaH Sodium hydride
NCS N-chlorosuccinimide
NMP N-methyl-2-pyrrolidone
PE petroleum ether
Pd(dppf)Cl$_2$ [1,1'-Bis(diphenylphosphino)ferrocene]palladium(II)dichloride
Pd$_2$(dba)$_3$ tris(dibenzylideneacetone)dipalladium(0)
Pd(PPh$_3$)$_4$ tetrakis(triphenylphosphine)palladium(0)
PMB p-Methoxybenzyl
PPh$_3$ triphenylphosphine
THF tetrahydrofuran
TFA Trifluoroacetic acid
TFE trifluoroethanol
TsOH 4-methylbenzensulfonic acid
Xphos 2-dicyclohexylphosphino-2',4',6'-triisopropylbiphenyl Example 1

Synthesis of Compounds 1-9 and 11-82

Compound 1

4-amino-6-((1-(6-phenylimidazo[1,2-b]pyridazin-7-yl)ethyl)amino)pyrimidine-5-carbonitrile

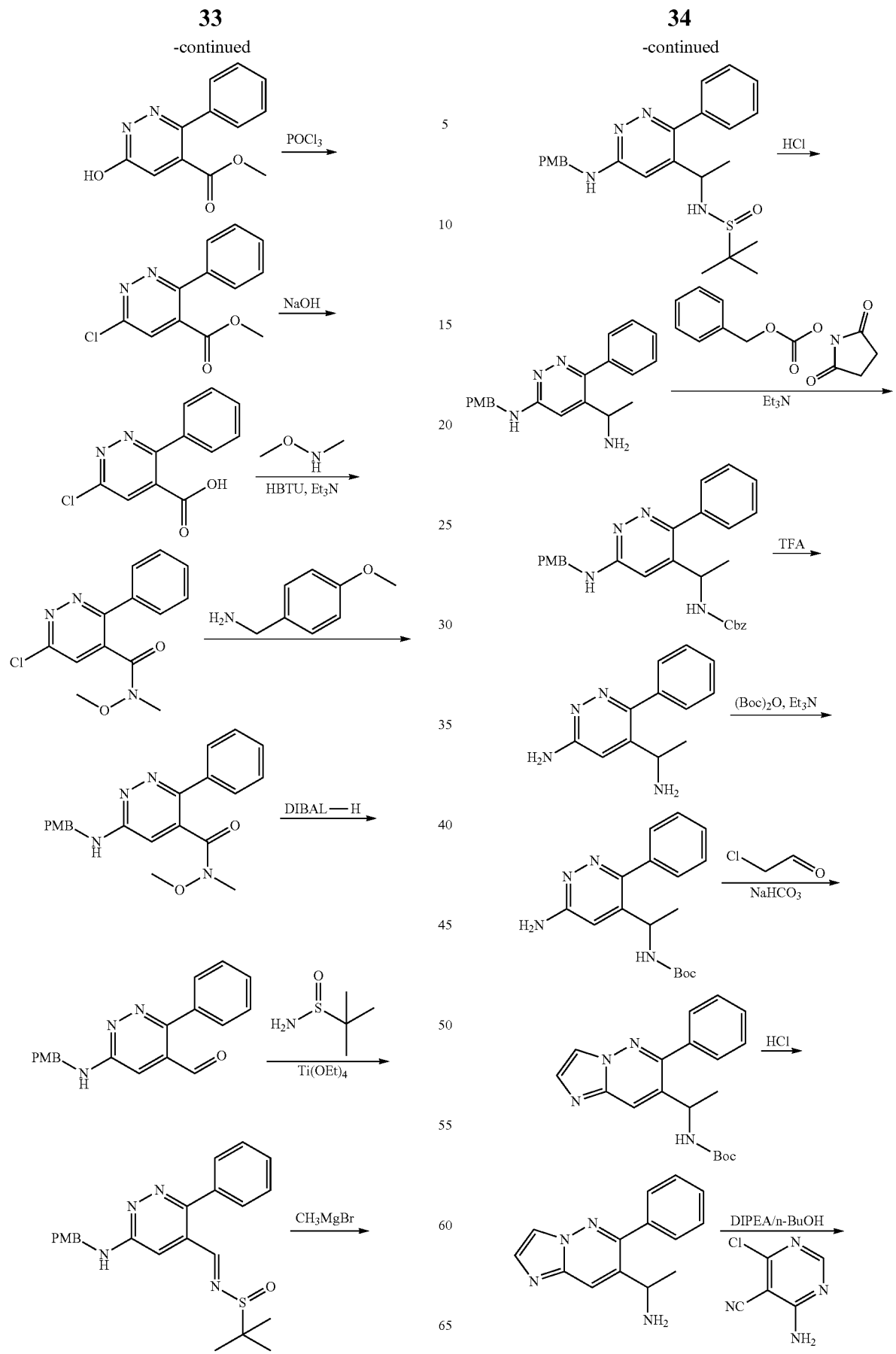

-continued

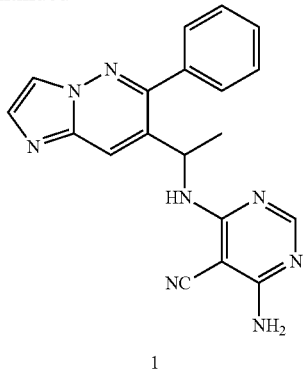

1

(A) 3-chloro-6-hydroxypyridazine-4-carboxylic acid

The solution of 3,6-dichloropyridazine-4-carboxylic acid (10 g, 51.8 mmol) in aq. NaOH (2N, 200 mL) was refluxed overnight. After cooling to room temperature, the reaction solution was acidified with hydrochloride acid solution until pH≈1-2. The solution was concentrated and the residue was purified by flash column chromatography ($H_2O$/MeOH) to give product (5.2 g, yield 57%) as yellow solid. MS (m/z): 175 $[M+H]^+$

(B) methyl 3-chloro-6-hydroxypyridazine-4-carboxylate

To a solution of 3-chloro-6-hydroxypyridazine-4-carboxylic acid (5 g, 28.7 mmol) in MeOH (30 mL) was added concentrated $H_2SO_4$ (1 mL). The solution was stirred at 100° C. overnight. After cooling to room temperature, the reaction solution was concentrated and the residue was purified by flash column chromatography ($H_2O$:MeOH=100:0 to 0:100) to give product (5 g, yield 93%) as white solid. MS (m/z): 189 $[M+H]^+$

(C) methyl 6-hydroxy-3-phenylpyridazine-4-carboxylate

To the mixture of methyl 3-chloro-6-hydroxypyridazine-4-carboxylate (5 g, 26.6 mmol), phenylboronic acid (6.49 g, 53.2 mmol) and KOAc (5.21 g, 53.2 mmol) in dioxane (60 mL) and $H_2O$ (6 mL) under $N_2$ atmosphere in a flask was added Pd(dppf)$Cl_2$ (1.08 g, 13.3 mmol). The mixture was stirred at 120° C. under $N_2$ atmosphere overnight. After cooling to room temperature the reaction solution was concentrated and the residue was purified by silica gel column chromatography (PE/EA=1/1) to give crude product, which was purified again by flash column chromatography ($H_2O$/MeOH=100:0 to 0:100) to obtain product (2.3 g, yield 37.6%) as white solid. MS (m/z): 231 $[M+H]^+$

(D) methyl 6-chloro-3-phenylpyridazine-4-carboxylate

The mixture of methyl 6-hydroxy-3-phenylpyridazine-4-carboxylate (2.3 g, 10 mmol) in $POCl_3$ (10 mL) was stirred at 110° C. for 6 hours. The extra $POCl_3$ was removed in vacuum and aq. $NaHCO_3$ was added. The mixture was concentrated to give crude product, which was then purified by silica gel column chromatography (PE/EA=3/1) to give product (2 g, yield 80.6%) as red solid. MS (m/z): 249 $[M+H]^+$

(E) 6-chloro-3-phenylpyridazine-4-carboxylic acid

NaOH (0.64 g, 16.12 mmol) was added to the solution of methyl 6-chloro-3-phenylpyridazine-4-carboxylate (2 g, 8.06 mmol) in MeOH (10 mL) and $H_2O$ (1 mL). The mixture was stirred at room temperature for 2 hours. The reaction solution was adjusted by hydrochloride acid solution until pH~3. The mixture was concentrated to give red solid of crude product which was used for next step reaction without further purification. MS (m/z): 235 $[M+H]^+$

(F) 6-chloro-N-methoxy-N-methyl-3-phenylpyridazine-4-carboxamide

The mixture of 6-chloro-3-phenylpyridazine-4-carboxylic acid (1.89 g, 8.06 mmol), N,O-dimethylhydroxylamine hydrochloride (1.56 g, 16.12 mmol), HBTU (6.11 g, 16.12 mmol) and $Et_3N$ (2.44 g, 24.18 mmol) in DCM (15 mL) was stirred at room temperature overnight. The reaction solution was concentrated and the residue was purified by flash column chromatography (PE/EA=3/1) to give product (1.75 g, yield 78.4%) as yellow solid. MS (m/z): 278 $[M+H]^+$

(G) N-methoxy-6-((4-methoxybenzyl)amino)-N-methyl-3-phenylpyridazine-4-carboxamide The mixture of (4-methoxyphenyl)methanamine (1.74 g, 12.68 mmol) and 6-chloro-N-methoxy-N-methyl-3-phenylpyridazine-4-carboxamide (1.75 g, 6.32 mmol) in NMP (30 mL) was stirred at 130° C. overnight. After cooling to room temperature the solution was extracted with EA. The organic phase was concentrated and purified by flash column chromatography ($H_2O$/MeOH=100:0 to 0:100) to give product (1.8 g, yield 75%) as yellow solid. MS (m/z): 379 $[M+H]^+$

(H) 6-((4-methoxybenzyl)amino)-3-phenylpyridazine-4-carbaldehyde

To the solution of N-methoxy-6-((4-methoxybenzyl)amino)-N-methyl-3-phenylpyridazine-4-carboxamide (1.8 g, 4.76 mmol) in dry THF (30 mL) at −20° C. under $N_2$ atmosphere was added DIBAL-H (14.3 g, 14.28 mmol) dropwise. And then the mixture was warmed to room temperature and stirred for another 4 hours. After that the mixture was quenched with aq. $NH_4Cl$ and extracted with EA. The organic phase was concentrated and purified by flash column chromatography (PE:EA=100:0 to 1:1) to give product (0.7 g, yield 46%) as yellow oil. MS (m/z): 320 $[M+H]^+$

(I) (E)-N-((6-((4-methoxybenzyl)amino)-3-phenylpyridazin-4-yl)methylene)-2-methylpropane-2-sulfinamide Ti(OEt)$_4$ (3 mL) was added to the solution of 6-((4-methoxybenzyl)amino)-3-phenylpyridazine-4-carbaldehyde (700 mg, 2.2 mmol) and 2-methylpropane-2-sulfinamide (399 mg, 3.3 mmol) in dry THF (30 mL) under by $N_2$ atmosphere. The mixture was stirred at 100° C. overnight. After cooling to room temperature, the mixture was treated with 2 mL $H_2O$ and filtered, the filtrate was extracted with EA and the organic layer was concentrated and the residue was purified by flash column chromatography (H₂O:MeOH=100:0 to 0:100) to give product (450 mg, yield 48%) as yellow solid. MS (m/z): 423 [M+H]⁺

(J) N-(1-(6-((4-methoxybenzyl)amino)-3-phenylpyridazin-4-yl)ethyl)-2-methylpropane-2-sulfinamide MeMgBr (1.07 mL, 3.21 mmol) was added dropwise to the solution of (E)-N-((6-((4-methoxybenzyl)amino)-3-phenylpyridazin-4-yl)methylene)-2-methylpropane-2-sulfinamide (450 mg, 1.07 mmol) in dry THF (30 mL) under atmosphere at 0° C. Then the mixture was stirred at 0° C. for additional 2 hours. After that the aq. NH₄Cl was added to quench the reaction, the reaction mixture was extracted with EA. The organic phase was washed with saturated brine, dried on anhydrous Na₂SO₄, and concentrated. The residue was used for next step reaction without further purification. MS (m/z): 439 [M+H]⁺

(K) benzyl (1-(6-((4-methoxybenzyl)amino)-3-phenylpyridazin-4-yl)ethyl)carbamate Concentrated hydrochloride acid solution (1 mL) was added to the solution of N-(1-(6-((4-methoxybenzyl)amino)-3-phenylpyridazin-4-yl)ethyl)-2-methylpropane-2-sulfinamide (469 mg, 1.07 mmol) in MeOH (15 mL). The mixture was stirred at room temperature for 1 hour, and then concentrated to remove extra solvent, dried to give 5-(1-aminoethyl)-N-(4-methoxybenzyl)-6-phenylpyridazin-3-amine as crude product, which was then mixed with benzyl (2,5-dioxopyrrolidin-1-yl) carbonate (533 mg, 2.14 mmol) and Et₃N (3 mL) in DCM (20 mL). The mixture was stirred at room temperature overnight. After that the reaction mixture was treated with H₂O, extracted with DCM. The organic phase was dried on anhydrous Na₂SO₄, concentrated to give crude product which was used for next step reaction without further purification. MS (m/z): 469 [M+H]⁺

(L) 5-(1-aminoethyl)-6-phenylpyridazin-3-amine

The solution of benzyl (1-(6-((4-methoxybenzyl)amino)-3-phenylpyridazin-4-yl)ethyl)carbamate (501 mg, 1.07 mmol) in CF₃COOH (3 mL) was stirred at room temperature for 12 hours. After that the solution was adjusted by aq. Na₂CO₃ until pH~7, concentrated and the residue was purified by flash column chromatography (H₂O:MeOH=100:0 to 0:100) to give product (214 mg, yield 93%). MS (m/z): 215 [M+H]⁺

(M) tert-butyl (1-(6-amino-3-phenylpyridazin-4-yl)ethyl)carbamate

The solution of 5-(1-aminoethyl)-6-phenylpyridazin-3-amine (214 mg, 1 mmol) and Et₃N (0.5 mL) in EtOH (10 mL) was added di-tert-butyl dicarbonate (218 mg, 1 mmol). The mixture was stirred at room temperature for 2 hours, after which the mixture was concentrated to give crude product which was used for next step reaction without further purification. MS (m/z): 315 [M+H]⁺

(N) tert-butyl (1-(6-phenylimidazo[1,2-b]pyridazin-7-yl)ethyl)carbamate

To a solution of tert-butyl (1-(6-amino-3-phenylpyridazin-4-yl)ethyl)carbamate (314 mg, 1 mmol) in EtOH (10 mL) was added and NaHCO₃ (252 mg, 3 mmol) 2-chloroacetaldehyde (3 mL, 40%). The mixture was stirred at 80° C. for 2 hours. After cooling to room temperature the solution was added aq. NaHCO₃ until pH~8. The mixture was concentrated and the residue was purified by flash column chromatography (H₂O:MeOH=100:0 to 0:100) to give product (90 mg, yield 27%) as yellow solid. MS (m/z): 339 [M+H]⁺

(O) 1-(6-phenylimidazo[1,2-b]pyridazin-7-yl)ethanamine

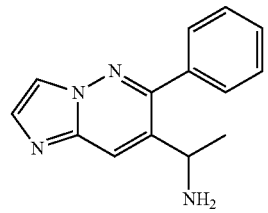 [SMILES: CC(N)c1cc2nccn2nc1-c1ccccc1]

To a solution of tert-butyl (1-(6-phenylimidazo[1,2-b]pyridazin-7-yl)ethyl)carbamate (45 mg, 0.13 mmol) in MeOH (3 mL) was added conc. HCl solution (0.2 mL). The mixture was stirred at room temperature for 1 hour, then concentrated to give crude product which was used for next step reaction without further purification. MS (m/z): 239 [M+H]⁺

(P) 4-amino-6-((1-(6-phenylimidazo[1,2-b]pyridazin-7-yl)ethyl)amino)pyrimidine-5-carbonitrile The mixture of 1-(6-phenylimidazo[1,2-b]pyridazin-7-yl)ethanamine (31 mg, 0.13 mmol) and 4-amino-6-chloropyrimidine-5-carboxynitrile (20 mg, 0.13 mmol), DIPEA (50 mg, 0.39 mmol) in n-BuOH (5 mL) was stirred at 130° C. overnight. After cooling to room temperature the solution was concentrated and the residue was purified by flash column chromatography (H₂O:MeOH=100:0 to 0:100) to give product (45 mg, yield 100%) as white solid. MS (m/z): 357 [M+]⁺

¹H NMR (400 MHz, CD₃OD) δ: 8.055 (s, 1H), 8.012 (s, 1H), 7.881 (s, 1H), 7.711 (d, J=1.2 Hz, 1H), 7.642-7.618 (m, 2H), 7.494-7.441 (m, 3H). 5.440-5.389 (m, 1H), 1.401 (d, J=6.8 Hz, 3H).

Compound 2

4-amino-6-((1-(3-chloro-6-phenylimidazo[1,2-b]pyridazin-7-yl)ethyl)amino)pyrimidine-5-carbonitrile

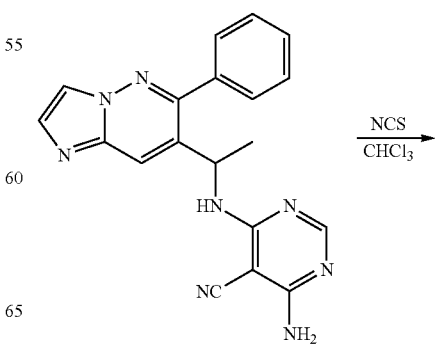

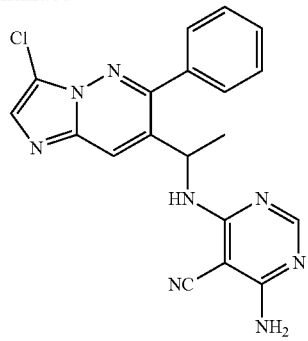

2

The mixture of 4-amino-6-((1-(6-phenylimidazo[1,2-b]pyridazin-7-yl)ethyl)amino)pyrimidine-5-carbonitrile (35 mg, 0.1 mmol) and NCS (26 mg, 0.2 mmol) in CHCl₃ (10 mL) was stirred at 80° C. for 6 hours. The mixture was cooled to room temperature, concentrated in vacuo, and the residue was purified by silica gel column chromatography (DCM/MeOH) to give 15 mg of target product. MS (m/z)=391 [M+H]⁺.

¹H NMR (400 MHz, CD₃OD) δ: 8.032 (s, 1H), 7.882 (s, 1H), 7.715 (s, 1H), 7.667-7.643 (m, 2H), 7.491-7.474 (m, 3H), 5.445-5.391 (m, 1H), 1.408 (d, J=7.2 Hz, 3H).

Compound 3 and 4

(R)-4-amino-6-((1-(3-chloro-6-phenylimidazo[1,2-b]pyridazin-7-yl)ethyl)amino)pyrimidine-5-carbonitrile and (S)-4-amino-6-((1-(3-chloro-6-phenylimidazo[1,2-b]pyridazin-7-yl)ethyl)amino)pyrimidine-5-carbonitrile

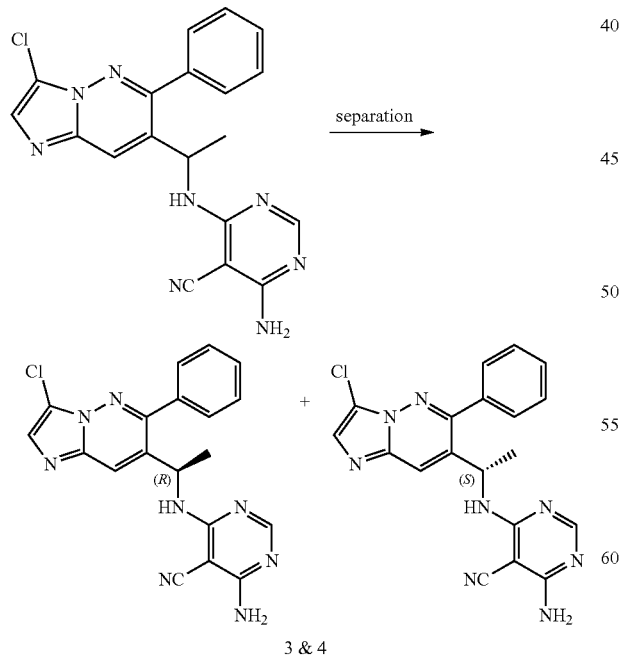

3 & 4

The racemic compound 2 was resolved by chiral HPLC to provide the optically pure enantiomers compound 3 and 4 (HPLC conditions: column: daicel IA 4.6×250 mm; mobile phase: EtOH/DEA=100/0.10; flow rate=1.0 mL/min; detector: UV 254 nm). The first eluent (compound 4, the S isomer, Rt=6.833 min) was 100% ee, MS (m/z): 391 [M+H]⁺. The second eluent (compound 3, the R isomer, Rt=12.51 min) was 98.07% ee, MS (m/z): 391 [M+H]⁺.

Compound 3: ¹H NMR (400 MHz, CD₃OD) δ: 8.03 (s, 1H), 7.88 (s, 1H), 7.71 (s, 1H), 7.68-7.61 (m, 2H), 7.51-7.44 (m, 3H), 5.44-5.39 (m, 1H), 1.40 (d, J=6.9 Hz, 3H).

Compound 4: ¹H NMR (400 MHz, CD₃OD) δ: 8.04 (d, J=2.0 Hz, 1H), 7.89 (d, J=1.7 Hz, 1H), 7.72 (s, 1H), 7.69-7.64 (m, 2H), 7.53-7.44 (m, 3H), 5.48-5.37 (m, 1H), 1.40 (d, J=6.9 Hz, 3H).

Compound 4

(S)-4-amino-6-((1-(3-chloro-6-phenylimidazo[1,2-b]pyridazin-7-yl)ethyl)amino)pyrimidine-5-carbonitrile

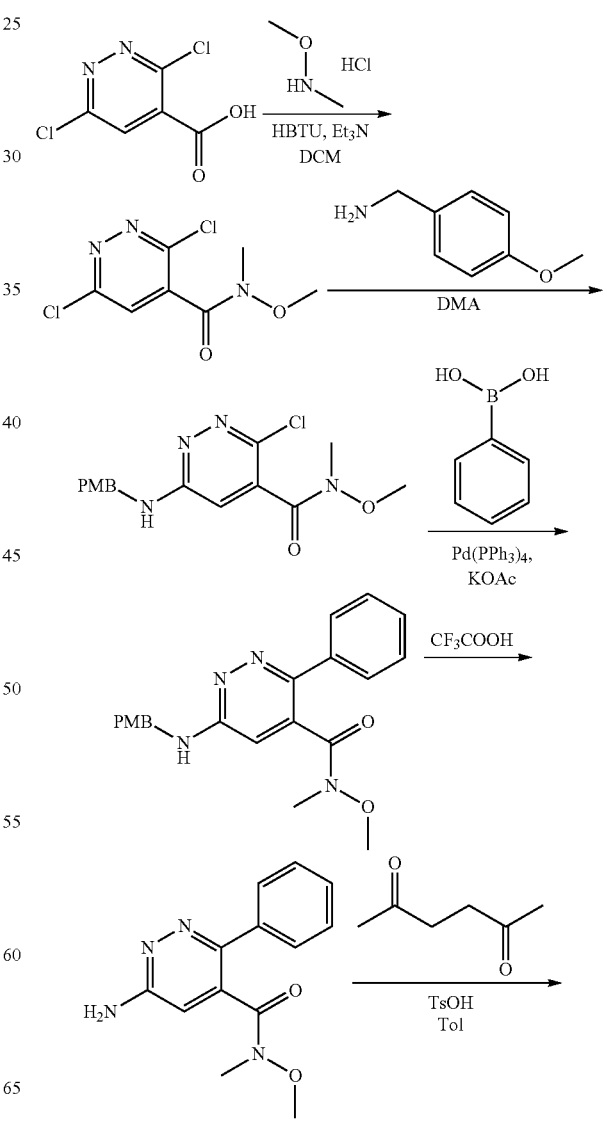

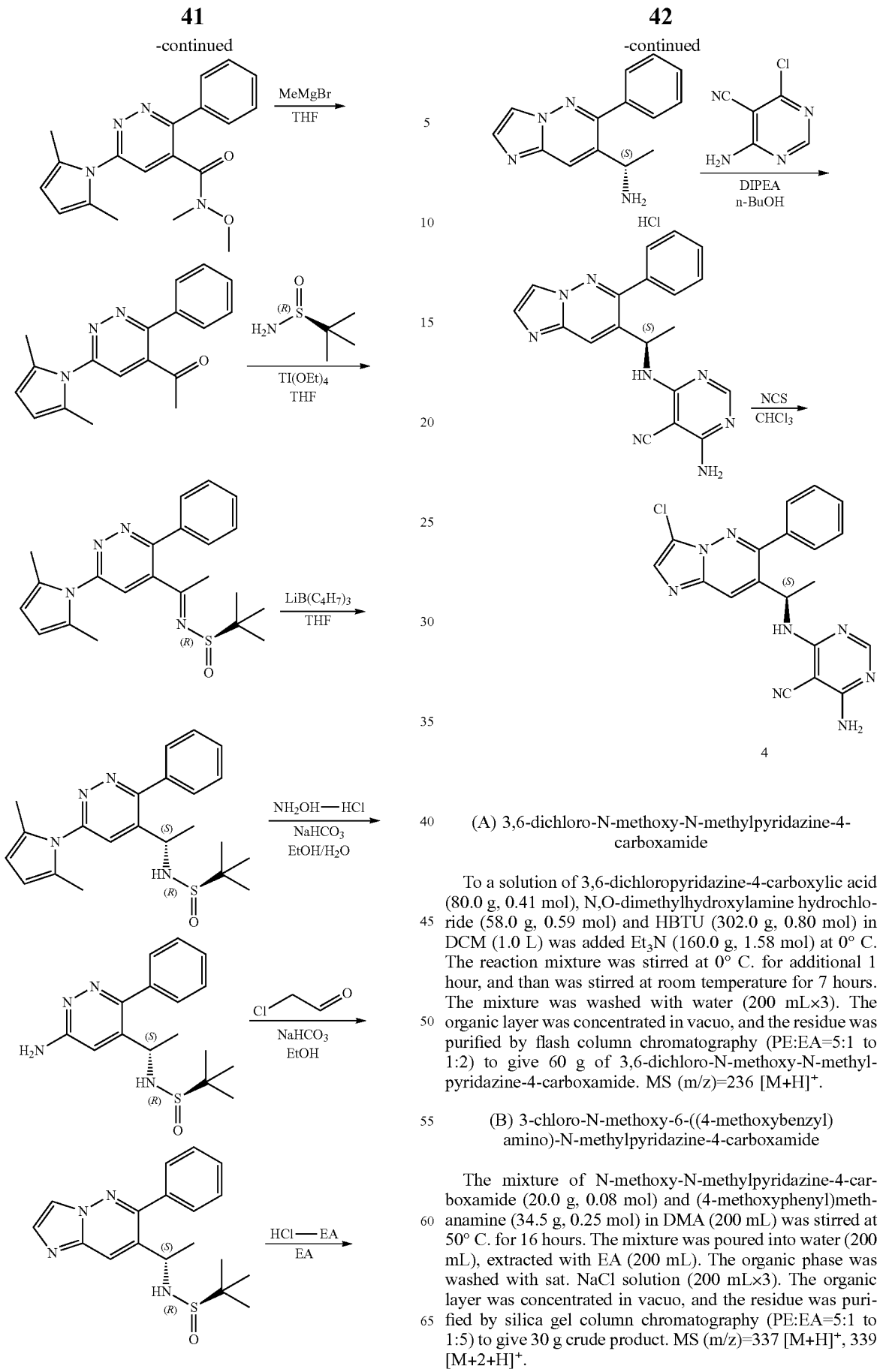

(A) 3,6-dichloro-N-methoxy-N-methylpyridazine-4-carboxamide

To a solution of 3,6-dichloropyridazine-4-carboxylic acid (80.0 g, 0.41 mol), N,O-dimethylhydroxylamine hydrochloride (58.0 g, 0.59 mol) and HBTU (302.0 g, 0.80 mol) in DCM (1.0 L) was added Et₃N (160.0 g, 1.58 mol) at 0° C. The reaction mixture was stirred at 0° C. for additional 1 hour, and than was stirred at room temperature for 7 hours. The mixture was washed with water (200 mL×3). The organic layer was concentrated in vacuo, and the residue was purified by flash column chromatography (PE:EA=5:1 to 1:2) to give 60 g of 3,6-dichloro-N-methoxy-N-methylpyridazine-4-carboxamide. MS (m/z)=236 [M+H]⁺.

(B) 3-chloro-N-methoxy-6-((4-methoxybenzyl)amino)-N-methylpyridazine-4-carboxamide The mixture of N-methoxy-N-methylpyridazine-4-carboxamide (20.0 g, 0.08 mol) and (4-methoxyphenyl)methanamine (34.5 g, 0.25 mol) in DMA (200 mL) was stirred at 50° C. for 16 hours. The mixture was poured into water (200 mL), extracted with EA (200 mL). The organic phase was washed with sat. NaCl solution (200 mL×3). The organic layer was concentrated in vacuo, and the residue was purified by silica gel column chromatography (PE:EA=5:1 to 1:5) to give 30 g crude product. MS (m/z)=337 [M+H]⁺, 339 [M+2+H]⁺.

¹H NMR (400 MHz, CDCl₃) δ: 7.30-7.16 (m, 2H), 6.89-6.76 (m, 2H), 6.59 (s, 1H), 5.46 (s, 1H), 4.50 (d, J=5.6 Hz, 2H), 3.76 (s, 3H), 3.43 (s, 3H), 3.30 (s, 3H).

(C) N-methoxy-6-((4-methoxybenzyl)amino)-N-methyl-3-phenylpyridazine-4-carboxamide To a solution of 3-chloro-N-methoxy-6-((4-methoxybenzyl)amino)-N-methylpyridazine-4-carboxamide (30.0 g, 0.09 mol) and phenylboronic acid (16.0 g, 0.13 mol) in dioxane (300 mL) and water (30 mL) was added Pd(PPh₃)₄ (5.1 g, 4.45 mmol) and KOAc (26.0 g, 0.26 mol) under nitrogen atmosphere. The reaction mixture was stirred at 110° C. overnight, and then cooled to room temperature. The mixture was poured into water (300 mL), extracted with EA (500 mL×3). The organic layer was concentrated in vacuo, and the residue was purified by flash column chromatography to give 40 g of target product. MS (m/z)=379 [M+H]⁺.

(D) 6-amino-N-methoxy-N-methyl-3-phenylpyridazine-4-carboxamide

The mixture of N-methoxy-6-((4-methoxybenzyl)amino)-N-methyl-3-phenylpyridazine-4-carboxamide (40.0 g, 0.10 mol) in CF₃COOH (150 mL) was stirred at 80° C. for 3 hours. The mixture was cooled to room temperature, concentrated in vacuo, and the residue was dissolved in DCM (200 mL), washed with sat. NaHCO₃ solution. The aqueous layer was extracted with (DCM+30% MeOH). The combined organic layer was dried over anhydrous Na₂SO₄, concentrated in vacuo to give 30 g of crude product. MS (m/z)=259 [M+H]⁺.

(E) 6-(2,5-dimethyl-1H-pyrrol-1-yl)-N-methoxy-N-methyl-3-phenylpyridazine-4-carboxamide To a solution of 6-amino-N-methoxy-N-methyl-3-phenylpyridazine-4-carboxamide (30.0 g, 0.11 mol) and hexane-2,5-dione (66.0 g, 0.58 mol) in toluene (300 mL) was added TsOH (2.0 g, 0.01 mol). The mixture was stirred at 120° C. overnight with Dean-stark trap, and then cooled to room temperature. The mixture was concentrated in vacuo, and the residue was purified by silica gel column chromatography (PE:EA=5:1 to 2:1) to give 14 g product. MS (m/z)=337 [M+H]⁺.

(F) 1-(6-(2,5-dimethyl-1H-pyrrol-1-yl)-3-phenylpyridazin-4-yl)ethanone

To a solution of 6-(2,5-dimethyl-1H-pyrrol-1-yl)-N-methoxy-N-methyl-3-phenylpyridazine-4-carboxamide (14.0 g, 0.04 mol) in dry THF (150 mL) was added MeMgBr (27.7 mL, 0.082 mol) at −5+C.~0° C. under nitrogen atmosphere. The mixture was stirred at 0~10° C. for additional 2 hours. The mixture was poured into sat. NH₄Cl solution, the aqueous layer was extracted with EA (100 mL×3). The organic layer was concentrated in vacuo to give 15 g crude product. MS (m/z)=292 [M+H]⁺.

(G) (R,E)-N-(1-(6-(2,5-dimethyl-1H-pyrrol-1-yl)-3-phenylpyridazin-4-yl)ethylidene)-2-methylpropane-2-sulfinamide To a solution of 1-(6-(2,5-dimethyl-1H-pyrrol-1-yl)-3-phenylpyridazin-4-yl)ethanone (15.0 g, 0.05 mol) and (R)-2-methylpropane-2-sulfinamide (9.3 g, 0.08 mol) in dry THF (150 mL) was added Ti(OEt)₄ (23.0 g, 0.10 mol) under nitrogen atmosphere. The mixture was stirred at 80° C. overnight, and then was cooled to room temperature. The mixture was poured into water (100 mL), the precipitate was filtered and the filtrate was extracted with EA. The organic layer was concentrated in vacuo, and the residue was purified by silica gel column chromatography (PE:EA=5:1 to 1:1) to obtain 12 g product. MS (m/z)=395 [M+H]⁺.

(H) (R)-N-((S)-1-(6-(2,5-dimethyl-1H-pyrrol-1-yl)-3-phenylpyridazin-4-yl)ethyl)-2-methylpropane-2-sulfinamide To a solution of (R,E)-N-(1-(6-(2,5-dimethyl-1H-pyrrol-1-yl)-3-phenylpyridazin-4-yl)ethylidene)-2-methylpropane-2-sulfinamide (12.0 g, 0.03 mol) in dry THF (150 mL) was added LiB(C₄H₇)₃ (6.08 mL, 0.06 mol) at −78° C. under nitrogen atmosphere. The mixture was stirred at −78° C. for additional 2 hours. The mixture was poured into sat. NH₄Cl solution, the aqueous layer was extracted with EA (100 mL×3), the organic layer was concentrated in vacuo, and the residue was purified by silica gel column chromatography (PE:EA=5:1 to 1:1) to give 10 g of title product. MS (m/z)=397 [M+H]⁺.

(I) (R)-N-((S)-1-(6-amino-3-phenylpyridazin-4-yl)ethyl)-2-methylpropane-2-sulfinamide To a solution of (R)-N-((S)-1-(6-(2,5-dimethyl-1H-pyrrol-1-yl)-3-phenylpyridazin-4-yl)ethyl)-2-methylpropane-2-sulfinamide (8.0 g. 0.02 mol) in EtOH (40 mL) and water (40 mL) was added NH₂OH.HCl (13.8 g, 0.20 mol), and NaHCO₃ (13.5 g, 0.16 mol). The mixture was stirred at 90° C. overnight, and then was cooled to room temperature. The mixture was treated with aq. NH₃.H₂O until pH=8~9. The mixture was concentrated in vacuo, and the residue was purified by flash column chromatography (MeOH/H₂O+ 0.5% NH₃.H₂O) to give 4.2 g title product. MS (m/z)=319 [M+H]⁺.

(J) (R)-2-methyl-N-((S)-1-(6-phenylimidazo[1,2-b]pyridazin-7-yl)ethyl)propane-2-sulfinamide To a solution of (R)-N-((S)-1-(6-amino-3-phenylpyridazin-4-yl)ethyl-2-methylpropane-2-sulfinamide (4.2 g, 0.013 mol) in EtOH (50 mL) was added 2-chloroacetaldehyde (5.15 g, 0.065 mol) and NaHCO₃ (2.1 g, 0.026 mol). The mixture was stirred at reflux overnight. The mixture was poured into water (50 mL), the aqueous layers was extracted with DCM (50 mL×3). The combined organic layer was concentrated in vacuo to give 6.5 g of crude product. MS (m/z)=343 [M+H]⁺.

(K) (S)-1-(6-phenylimidazo[1,2-b]pyridazine-7-yl)ethanamine

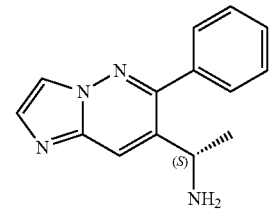

To a solution of (R)-2-methyl-N-((S)-1-(6-phenylimidazo[1,2-b]pyridazin-7-yl)ethyl)propane-2-sulfinamide (6.5 g, 0.019 mol) in EA (20 mL) was added HCl solution in EA (20 mL, 2.44 mmol) at 0° C. The mixture was stirred at room temperature for 1 hour, then the mixture was concentrated in vacuo and the residue was purified by flash column chromatography (MeOH/H$_2$O+0.5% NH$_3$.H$_2$O) to give 4.2 g of crude product. MS (m/z)=239 [M+H]$^+$.

(L) (S)-4-amino-6-((1-(6-phenylimidazo[1,2-b]pyridazin-7-yl)ethyl)amino)pyrimidine-5-carbonitrile To a solution of (S)-1-(6-phenylimidazo[1,2-b]pyridazin-7-yl)ethanamine (3.8 g, 0.016 mol) and 4-amino-6-chloropyrimidine-5-carbonitrile (3.7 g, 0.024 mol) in n-BuOH (40 ml) was added DIPEA (6.1 g, 0.048 mol). The mixture was stirred at reflux overnight, and then cooled to room temperature. The mixture was concentrated in vacuo, and the residue was purified by flash column chromatography (MeOH/H$_2$O+0.5% NH$_3$.H$_2$O) to give 2.6 g title product. MS (m/z)=357 [M+H]$^+$.

(M) (S)-4-amino-6-((1-(3-chloro-6-phenylimidazo[1,2-b]pyridazin-7-yl)ethyl)amino)pyrimidine-5-carbonitrile The mixture of (S)-4-amino-6-((1-(6-phenylimidazo[1,2-b]pyridazin-7-yl)ethyl)amino)pyrimidine-5-carbonitrile (4 g, 0.011 mol) and NCS (2.3 g, 0.017 mol) in CHCl$_3$ (40 ml) was stirred at reflux for 2 hours. The mixture was cooled to room temperature, concentrated in vacuo, and the residue was purified by flash column chromatography (DCM/MeOH) to give 1.8 g of target product. MS (m/z)=391 [M+H]$^+$.

$^1$H NMR (400 MHz, CDCl$_3$) δ: 8.06 (s, 1H), 7.95 (s, 1H), 7.74-7.63 (m, 3H), 7.56-7.47 (m, 3H), 5.46 (d, J=5.9 Hz, 1H), 5.43-5.37 (m, 1H), 5.36 (s, 2H), 1.38 (d, J=6.8 Hz, 3H).

The following compounds were prepared according to the procedures of Compound 4 using the corresponding intermediates and reagents under appropriate conditions that will be recognized by the POSITA.

| Compound | Structure | MS (M + H)$^+$ | NMR | Intermediate |
|---|---|---|---|---|
| 9 | 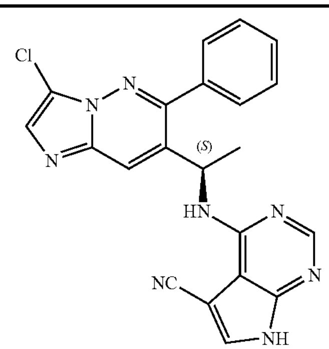 | 415 | $^1$H NMR (400 MHz, CDCl$_3$) δ: 8.29 (s, 1H), 8.01 (s, 1H), 7.78-7.76 (m, 2H), 7.66 (s, 1H), 7.62 (s, 1H), 7.51-7.49 (m, 3H), 5.85 (d, J = 5.8 Hz, 1H), 5.56-5.46 (m, 1H), 1.43 (d, J = 6.8 Hz, 3H). | |
| 11 | 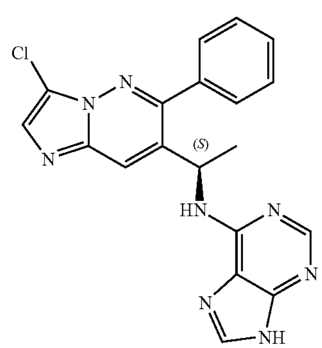 | 391 | $^1$H NMR (400 MHz, CD$_3$OD) δ: 8.16 (s, 1H), 8.09 (s, 2H), 7.78-7.77 (m, 2H), 7.71 (s, 1H), 7.55-7.41 (m, 3H), 5.59-5.45 (m, 1H), 1.46 (d, J = 6.8 Hz, 3H). | |
| 12 | 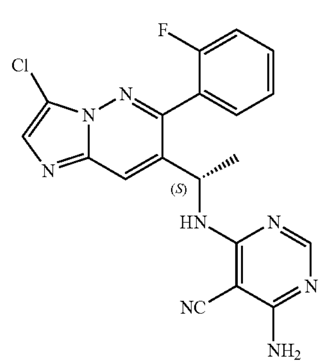 | 409 | $^1$H NMR (400 MHz, DMSO-d6) δ: 8.31 (s, 1H), 7.93 (s, 1H), 7.79-7.63 (m, 2H), 7.60-7.45 (m, 2H), 7.30 (t, J = 7.4 Hz, 2H), 7.13 (s, 2H), 5.09 (s, 1H), 1.45 (d, J = 6.8 Hz, 3H). | MS (M + H)$^+$: 257 |

-continued

| Compound | Structure | MS (M + H)+ | NMR | Intermediate |
|---|---|---|---|---|
| 13 | (structure) | 409 | ¹H NMR (400 MHz, CD₃OD) δ: 8.16 (s, 1H), 8.04 (s, 2H), 7.75 (s, 1H), 7.60 (s, 1H), 7.47-7.38 (m, 1H), 7.19 (s, 2H), 5.32 (br, 1H), 1.60 (d, J = 6.9 Hz, 3H). | (structure) MS (M + H)+: 257 |
| 15 | (structure) | 409 | ¹H NMR (400 MHz, DMSO-d6) δ: 8.30 (s, 1H), 7.92 (s, 1H), 7.86 (s, 1H), 7.71 (d, J = 7.4 Hz, 1H), 7.57-7.44 (m, 3H), 7.31 (dd, J = 8.7 Hz, 2.0 Hz, 1H), 7.22 (s, 2H), 5.18 (t, J = 7.0 Hz, 1H), 1.39 (d, J = 6.9 Hz, 3H). | (structure) MS (M + H)+: 257 |
| 16 | (structure) | 409 | ¹H NMR (400 MHz, DMSO-d₆) δ: 8.28 (s, 2H), 8.09 (d, J = 6.8 Hz, 2H), 7.88 (s, 1H), 7.76-7.48 (m, 4H), 7.36 (dd, J = 9.0 Hz, 6.6 Hz, 1H), 5.30 (s, 1H), 1.40 (d, J = 5.7 Hz, 3H). | (structure) MS (M + H)+: 257 |
| 17 | (structure) | 390 | ¹H NMR (400 MHz, DMSO-d₆) δ: 8.30 (s, 1H), 8.21 (s, 1H), 8.02 (s, 1H), 7.72-7.70 (m, 3H), 7.50-7.48 (m, 3H), 7.30 (s, 1H), 6.75 (d, J = 6.8 Hz, 1H), 5.35-5.21 (m, 1H), 1.43 (d, J = 6.8 Hz, 3H). | (structure) |

-continued

| Compound | Structure | MS (M + H)+ | NMR | Intermediate |
|---|---|---|---|---|
| 22 | 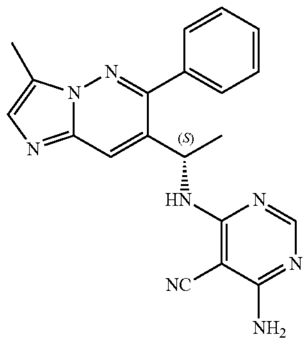 | 371 | ¹H NMR (400 MHz, CD₃OD) δ: 7.98 (s, 1H), 7.89 (s, 1H), 7.66-7.64 (m, 2H), 7.53-7.44 (m, 4H), 5.45-5.40 (m, 1H), 2.53 (s, 3H), 1.40 (d, J = 6.9 Hz, 3H). | |
| 23 | 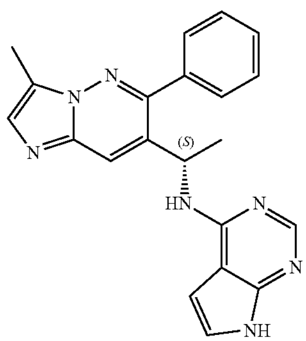 | 371 | ¹H NMR (400 MHz, CD₃OD) δ: 8.04 (s, 1H), 8.00 (s, 1H), 7.84 (s, 1H), 7.78-7.71 (m, 2H), 7.50-7.42 (m, 4H), 5.52-5.47 (m, 1H), 2.53 (s, 3H), 1.42 (d, J = 6.8 Hz, 3H). | |
| 58 | 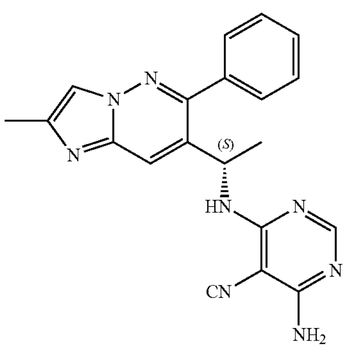 | 371 | ¹H NMR (400 MHz, CDCl₃) δ 8.02 (s, 1H), 7.89 (s, 1H), 7.71 (s, 1H), 7.61-7.60 (m, 2H), 7.52-7.47 (m, 3H), 5.57-5.56 (m, 1H), 5.53 (s, 2H), 5.45-5.32 (m, 1H), 2.48 (s, 3H), 1.38 (d, J = 6.4 Hz, 3H). | MS (M + H)+: 253 |
| 59 | 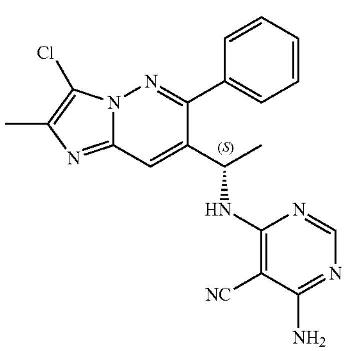 | 405 | ¹H NMR (400 MHz, CDCl₃) δ 8.03 (s, 1H), 7.83 (s, 1H), 7.66-7.64 (m, 2H), 7.51-7.48 (m, 3H), 5.43 (d, J = 6.1 Hz, 1H), 5.40-5.36 (m, 1H), 5.33 (s, 2H), 2.48 (s, 3H), 1.36 (d, J = 6.7 Hz, 3H). | |

Compound 5 and 6
(R)-4-amino-6-((1-(6-phenylimidazo[1,2-b]pyridazin-7-yl)propyl)amino)pyrimidine-5-carbonitrile and (S)-4-amino-6-((1-(6-phenylimidazo[1,2-b]pyridazin-7-yl)propyl)amino)pyrimidine-5-carbonitrile
5
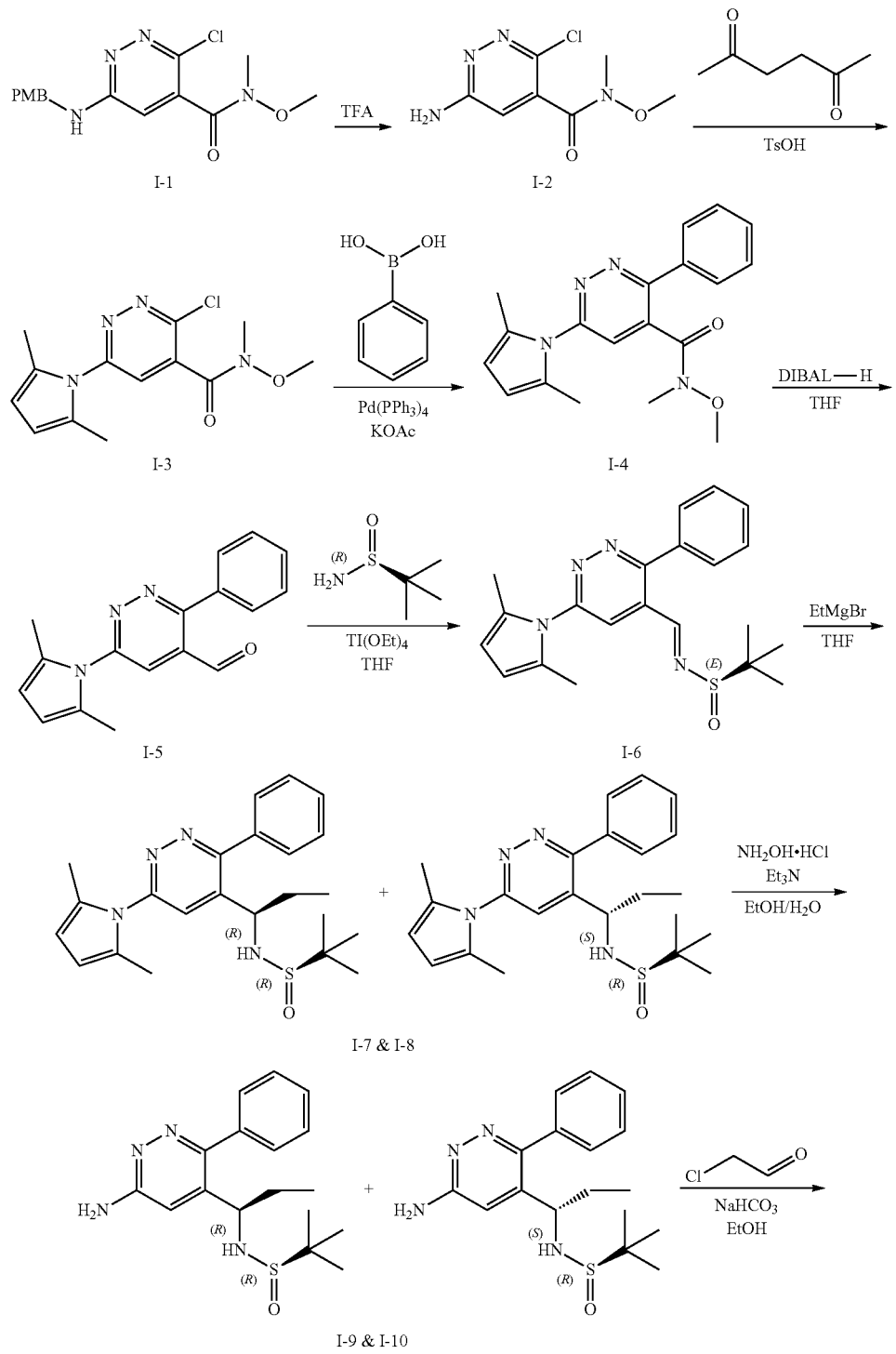

-continued

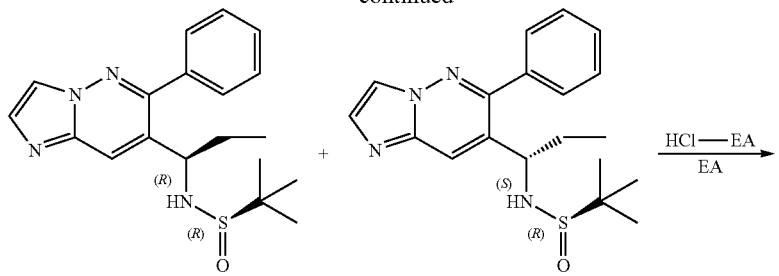

I-11 & I-12

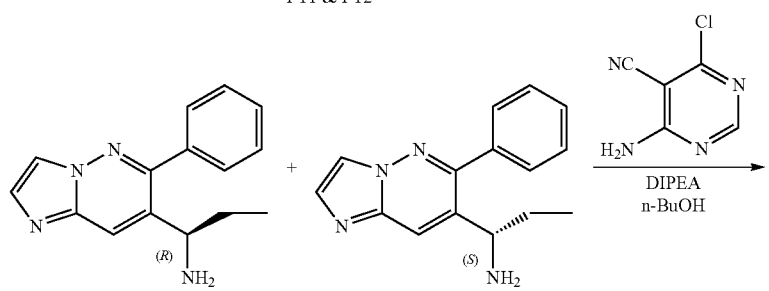

I-13 & I-14

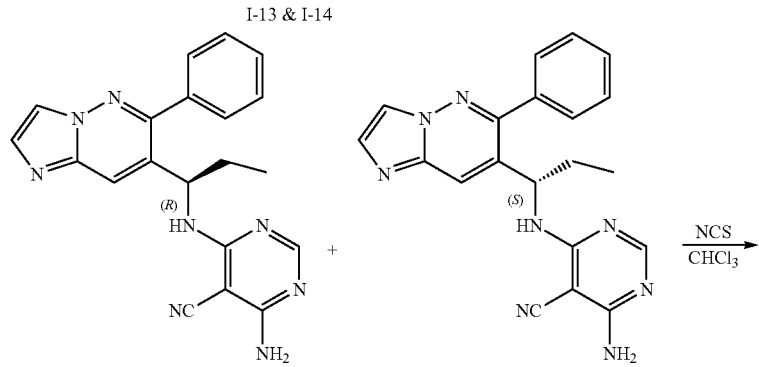

I-15 & I-16

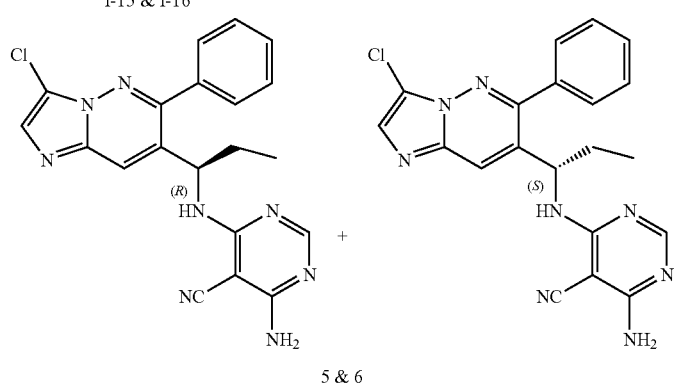

5 & 6

(A) 6-amino-3-chloro-N-methoxy-N-methyl-pyridazine-4-carboxamide

To a solution of 3-chloro-N-methoxy-6-((4-methoxybenzyl)amino)-N-methylpyridazine-4-carboxamide (Compound 4 (B), 7.4 g, 21.97 mmol) in TFA (20 mL) was stirred at reflux for 2 hours. The mixture was concentrated in vacuo, and the residue was poured into sat. NaHCO$_3$ solution. The mixture was stirred at room temperature for 30 minutes, extracted with EA, and the organic layer then concentrated in vacuo, and the residue was purified by flash column chromatography to give 3.84 g of 6-amino-3-chloro-N-methoxy-N-methylpyridazine-4-carboxamide. MS (m/z) =217 [M+H]$^+$, 219 [M+2+H]$^+$.

(B) 3-chloro-6-(2,5-dimethyl-1H-pyrrol-1-yl)-N-methoxy-N-methylpyridazine-4-carboxamide To a solution of 6-amino-3-chloro-N-methoxy-N-methylpyridazine-4-carboxamide (3.84 g, 17.73 mmol) and hexane-2,5-dione (8.45 g, 65.91 mmol) in toluene (100 mL) was added TsOH (2.0 g, 0.01 mol). The mixture was stirred at 120° C. overnight with Dean-stark trap, and then cooled to room temperature. The mixture was concentrated in vacuo, and the residue was purified by flash column chromatography to give 4.2 g of title product. MS (m/z)=295 [M+H]⁺, 297 [M+2+H]⁺.

(C) 6-(2,5-dimethyl-1H-pyrrol-1-yl)-N-methoxy-N-methyl-3-phenylpyridazine-4-carboxamide To a solution of 3-chloro-6-(2,5-dimethyl-1H-pyrrol-1-yl)-N-methoxy-N-methylpyridazine-4-carboxamide (4.2 g, 14.25 mmol) and phenylboronic acid (2.61 g, 21.37 mmol) in dioxane (80 mL) and water (8 mL) was added Pd(PPh$_3$)$_4$ and KOAc under nitrogen atmosphere. The reaction mixture was stirred at 110° C. overnight, and then cooled to room temperature. The mixture was poured into water (300 mL), extracted with EA (100 mL×3). The combined organic layer was concentrated in vacuo, and the residue was purified by flash column chromatography to give 4.3 g of product. MS (m/z)=337 [M+H]⁺

(D) 6-(2,5-dimethyl-1H-pyrrol-1-yl)-3-phenylpyridazine-4-carbaldehyde

To a solution of 6-(2,5-dimethyl-1H-pyrrol-1-yl)-N-methoxy-N-methyl-3-phenylpyridazine-4-carboxamide (4.3 g, 12.78 mmol) in dry THF (30 ml) was added DIBAL-H (19 mL, 19.17 mmol) under nitrogen atmosphere at −20° C. The reaction mixture was stirred at −20° C. for extra 1 hour, and then poured into water (300 mL), extracted with EA. The organic layer was concentrated in vacuo, and the residue was purified by flash column chromatography to give 0.95 g of title product. MS (m/z)=310 [M+MeOH+H]⁺

(E) (R,E)-N-((6-(2,5-dimethyl-1H-pyrrol-1-yl)-3-phenylpyridazin-4-yl)methylene)-2-methylpropane-2-sulfinamide To a solution of 6-(2,5-dimethyl-1H-pyrrol-1-yl)-3-phenylpyridazine-4-carbaldehyde (0.95 g, 3.43 mmol) and (R)-2-methylpropane-2-sulfinamide (0.62 g, 5.14 mmol) in dry THF (20 mL) was added Ti(OEt)$_4$ (1.56 g, 6.85 mmol) under nitrogen atmosphere. The reaction mixture was stirred at reflux overnight, then was cooled to room temperature. The mixture was poured into water (5 ml), the precipitate was filtered and the filtrate was extracted with EA. The organic layer was concentrated in vacuo, and the residue was purified by flash column chromatography to give 1.2 g of title product. MS (m/z)=381 [M+H]⁺

(F) (R)-N-((S)-1-(6-(2,5-dimethyl-1H-pyrrol-1-yl)-3-phenylpyridazin-4-yl)propyl)-2-methylpropane-2-sulfinamide and (R)-N-((R)-1-(6-(2,5-dimethyl-1H-pyrrol-1-yl)-3-phenylpyridazin-4-yl)propyl)-2-methylpropane-2-sulfinamide To a solution of (R,E)-N-((6-(2,5-dimethyl-1H-pyrrol-1-yl)-3-phenylpyridazin-4-yl)methylene)-2-methylpropane-2-sulfinamide (1.2 g, 3.15 mmol) in dry THF (20 mL) was added EtMgBr (1.58 mL, 4.73 mmol) at −78° C. under nitrogen atmosphere. The reaction mixture was stirred at −78° C. for 1 hour. The mixture was poured into water (5 mL), extracted with EA. The organic layer was concentrated in vacuo, and the residue was purified by flash silica gel column chromatography (PE:EA=1:0 to 0:1) to give two products (the first eluent is 0.47 g intermediate I-7, the second eluent is 0.18 g intermediate I-8), one being (R)-N-((S)-1-(6-(2,5-dimethyl-1H-pyrrol-1-yl)-3-phenylpyridazin-4-yl)propyl)-2-methylpropane-2-sulfinamide, and the other being (R)-N-((R)-1-(6-(2,5-dimethyl-1H-pyrrol-1-yl)-3-phenylpyridazin-4-yl)propyl)-2-methylpropane-2-sulfinamide. MS (m/z)=411 [M+H]⁺

(G) (R)-N-((R)-1-(6-amino-3-phenylpyridazin-4-yl)propyl)-2-methylpropane-2-sulfinamide and (R)-N-((S)-1-(6-amino-3-phenylpyridazin-4-yl)propyl)-2-methylpropane-2-sulfinamide To a solution of intermediate I-8 obtained in the last step reaction (0.18 g, 0.04 mmol) in EtOH (2.5 mL) and water (2.5 mL) was added NH$_2$OH.HCl (0.46 g, 6.58 mmol) and Et$_3$N (0.44 g, 4.38 mmol). The mixture was stirred at 90° C. overnight, and then was cooled to room temperature. The mixture was added aq. NH$_3$.H$_2$O until pH is 8~9, and than the mixture was concentrated in vacuo, and the residue was purified by flash column chromatography (MeOH/H$_2$O+0.5% NH$_3$.H$_2$O) to give 0.08 g of intermediate I-10. MS (m/z)=333 [M+H]⁺. Intermediate I-9 was prepared using intermediate I-7 under the same condition.

(H) (R)-2-methyl-N-((R)-1-(6-phenylimidazo[1,2-b]pyridazin-7-yl)propyl)propane-2-sulfinamide and (R)-2-methyl-N-((S)-1-(6-phenylimidazo[1,2-b]pyridazin-7-yl)propyl)propane-2-sulfinamide To a solution of intermediate I-10 (80 mg, 0.24 mmol) in EtOH (5 mL) was added 2-chloroacetaldehyde (0.32 mL, 1.92 mmol) and NaHCO$_3$ (40 mg, 0.48 mmol). The mixture was stirred at reflux overnight. The mixture was poured into water (10 mL), the aqueous layers was extracted with EA (20 mL×3). The combined organic layer was concentrated in vacuo, and the residue was purified by flash column chromatography (MeOH/H$_2$O+0.5% NH$_3$.H$_2$O) to give 67 mg of intermediate I-12. MS (m/z)=357 [M+H]⁺. Intermediate I-11 was prepared using Intermediate I-9 under the same condition.

(I) (R)-1-(6-phenylimidazo[1,2-b]pyridazin-7-yl)propan-1-amine and (S)-1-(6-phenylimidazo[1,2-b]pyridazin-7-yl)propan-1-amine

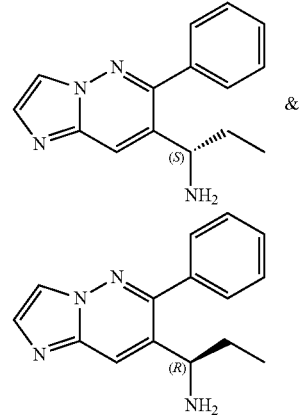

To a solution of intermediate I-12 (67 mg, 0.19 mmol) in EA (3 mL) was added HCl solution in EA (5 N, 1 mL) at 0° C. The mixture was stirred at room temperature for 1 hour, and then the mixture was concentrated in vacuo. The residue was dissolved in MeOH, and then basified by aq. NH$_3$.H$_2$O. Extra solvent was evaporated and the residue was purified by flash column chromatography (MeOH/H$_2$O+0.5% NH$_3$.H$_2$O) to give 30 mg of intermediate I-14. MS (m/z)=253 [M+H]⁺. Intermediate I-13 was prepared using intermediate I-11 under the same condition.

(J) (R)-4-amino-6-((1-(6-phenylimidazo[1,2-b]pyridazin-7-yl)propyl)amino)pyrimidine-5-carbonitrile and (S)-4-amino-6-((1-(6-phenylimidazo[1,2-b]pyridazin-7-yl)propyl)amino)pyrimidine-5-carbonitrile To a solution of intermediate I-14 (30 mg, 0.12 mmol) and 4-amino-6-chloropyrimidine-5-carbonitrile (27 mg, 0.19 mmol) in n-BuOH (3 mL) was added DIPEA (31 mg, 0.24 mmol). The mixture was stirred at reflux overnight. The mixture was cooled to room temperature, concentrated in vacuo, and the residue was purified by flash column chromatography (MeOH/H$_2$O+0.5% NH$_3$.H$_2$O) to give 30 mg of intermediate I-16. MS (m/z)=371 [M+H]$^+$. Intermediate I-15 was prepared using intermediate I-13 under the same condition.

(K) (R)-4-amino-6-((1-(3-chloro-6-phenylimidazo[1,2-b]pyridazin-7-yl)propyl)amino)pyrimidine-5-carbonitrile and (S)-4-amino-6-((1-(3-chloro-6-phenylimidazo[1,2-b]pyridazin-7-yl)propyl)amino)pyrimidine-5-carbonitrile The solution of intermediate I-16 (30 mg, 0.08 mmol) and NCS (16 mg, 0.12 mmol) in CHCl$_3$ (4 mL) was stirred at reflux for 2 hours. The mixture was coded to room temperature, concentrated in vacuo, and the residue was purified by flash column chromatography (MeOH/H$_2$O+0.5% NH$_3$ H$_2$O) to give 24 mg of one target compound 6. MS (m/z)=405 [M+H]$^+$. The other title compound 5 was prepared using intermediate I-15 under the same condition.

Compound 5: $^1$H NMR (400 MHz, CD$_3$OD) δ 8.03 (s, 1H), 7.92 (s, 1H), 7.73-7.69 (m, 3H), 7.53-7.50 (m, 3H), 5.29-5.25 (m, 1H), 1.83-1.71 (m, 2H), 0.80 (t, J=6.6 Hz, 3H).

Compound 6: $^1$H NMR (400 MHz, CD$_3$OD) δ 8.04 (s, 1H), 7.93 (s, 1H), 7.72 (dd, J=7.2 Hz, 2.4 Hz, 3H), 7.56-7.51 (m, 3H), 5.27 (dd, J=9.4 Hz, 5.0 Hz, 1H), 1.76 (qdd, J=12.4 Hz, 8.3 Hz, 6.1 Hz, 2H), 0.81 (t, J=7.3 Hz, 3H).

The following compounds were prepared according to the procedures of Compound 5 and 6 using the corresponding intermediates and reagents under appropriate conditions that will be recognized by the POSITA. More specifically, Compound 14 and 26 were prepared according to the procedures of Compound 5; Compound 18, 19, 24 and 25 were prepared according to the procedures of Compound 6.

| Compound | Structure | MS (M + H)$^+$ | NMR | Intermediate |
|---|---|---|---|---|
| 14 | (structure: 3-Cl-6-phenylimidazo[1,2-b]pyridazine with chiral propyl-NH-purinyl substituent) | 405 | $^1$H NMR (400 MHz, CD$_3$OD) δ: 8.19 (s, 1H), 8.10 (s, 1H), 8.05 (s, 1H), 7.83 (d, J = 3.6 Hz, 2H), 7.70 (s, 1H), 7.57-7.50 (m, 3H), 5.51-5.34 (m, 1H), 1.86-1.71 (m, 2H), 0.86 (t, J = 7.3 Hz, 3H). | (S)-intermediate with NH$_2$; MS (M + H)$^+$: 253 & |
| 18 | (structure: 3-Cl-6-phenylimidazo[1,2-b]pyridazine with chiral propyl-NH-purinyl substituent) | 405 | $^1$H NMR (400 MHz, CDCl$_3$) δ: 8.32 (s, 1H), 8.02 (s, 1H), 7.93 (s, 1H), 7.89-7.79 (m, 2H), 7.65 (d, J = 1.4 Hz, 1H), 7.58-7.47 (m, 4H), 6.53-6.41 (m, 1H), 5.48-5.37 (m, 1H), 1.68-1.59 (m, 2H), 0.85 (s, 3H). | (S)-intermediate with NH$_2$; MS (M + H)$^+$: 253 |

-continued

| Compound | Structure | MS (M + H)+ | NMR | Intermediate |
| --- | --- | --- | --- | --- |
| 19 | 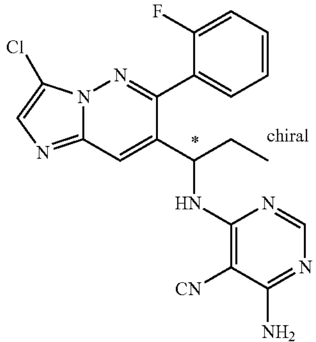 | 423 | ¹H NMR (400 MHz, CDCl₃) δ 7.98 (s, 1H), 7.93 (s, 1H), 7.73 (s, 1H), 7.58-7.46 (m, 2H), 7.32-7.26 (m, 1H), 7.22-7.18 (m, 1H), 5.50-5.41 (m, 1H), 5.10-4.98 (m, 1H), 1.95-1.84 (m, 1H), 1.83-1.75 (m, 1H), 0.92 (t, J = 7.3 Hz, 3H). | |
| 24 | 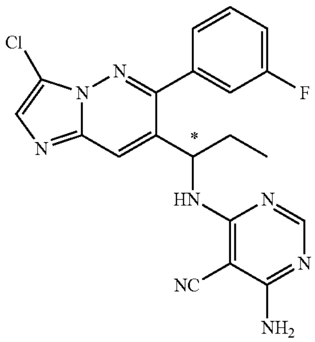 | 423 | ¹H NMR (400 MHz, CD₃OD) δ: 8.07 (s, 1H), 7.92 (s, 1H), 7.75 (s, 1H), 7.60-7.49 (m, 3H), 7.26 (d, J = 3.0 Hz, 1H), 5.25 (d, J = 4.2 Hz, 1H), 1.88-1.72 (m, 2H), 0.84 (t, J = 7.3 Hz, 3H). | MS (M + H)+: 271 |
| 25 | 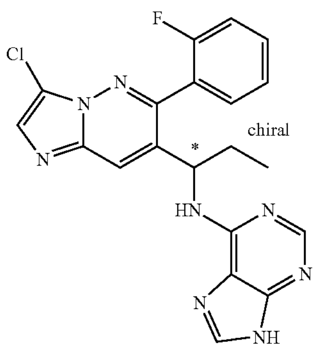 [SMILES: CCC(Nc1ncnc2[nH]cnc12)c1cc2ncc(Cl)n2nc1-c1ccccc1F] | 423 | ¹H NMR (400 MHz, CD₃OD) δ 8.14 (s, 1H), 8.03 (s, 1H), 8.00 (s, 1H), 7.75 (s, 1H), 7.68 (s, 1H), 7.56-7.47 (m, 1H), 7.31-7.16 (m, 2H), 5.28-5.15 (m, 1H), 2.01-1.88 (m, 2H), 0.95 (t, J = 7.3 Hz, 3H). | MS (M + H)+: 271 & |
| 26 | 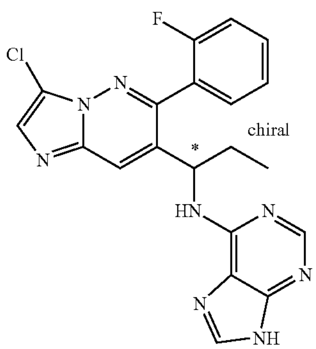 [SMILES: CCC(Nc1ncnc2[nH]cnc12)c1cc2ncc(Cl)n2nc1-c1ccccc1F] | 423 | ¹H NMR (400 MHz, CD₃OD) δ 8.14 (s, 1H), 8.04 (s, 1H), 8.02 (s, 1H), 7.75 (s, 1H), 7.67 (s, 1H), 7.54-7.46 (m, 1H), 7.32-7.14 (m, 2H), 5.31-5.09 (m, 1H), 2.01-1.90 (m, 2H), 0.95 (t, J = 7.3 Hz, 3H). | MS (M + H)+: 271 |

Retention time (Rt) of above compounds were tested by chiral HPLC. The R-HPLC conditions were as follows:
Column: daicel IA 4.6 × 250 mm;
Mobile phase: EtOH/DEA = 100/0.10;
Flow rate = 1.0 mL/min;
Detector: UV 254 nm.

Rt of compound 5 is 10.774 min, Rt of compound 6 is 5.032 min, Rt of compound 14 is 5.245 min, Rt of compound 18 is 7.030 min, Rt of compound 19 is 6.925 min, Rt of compound 24 is 4.991 min, Rt of compound 25 is 20.884 min, Rt of compound 26 is 14.505 min.

Compound 7 and 8

(R)-4-amino-6-((1-(3-chloro-6-(pyridin-2-yl)imidazo[1,2-b]pyridazin-7-yl)ethyl)amino)pyrimidine-5-carbonitrile and (S)-4-amino-6-((1-(3-chloro-6-(pyridin-2-yl)imidazo[1,2-b]pyridazin-7-yl)ethyl)amino)pyrimidine-5-carbonitrile

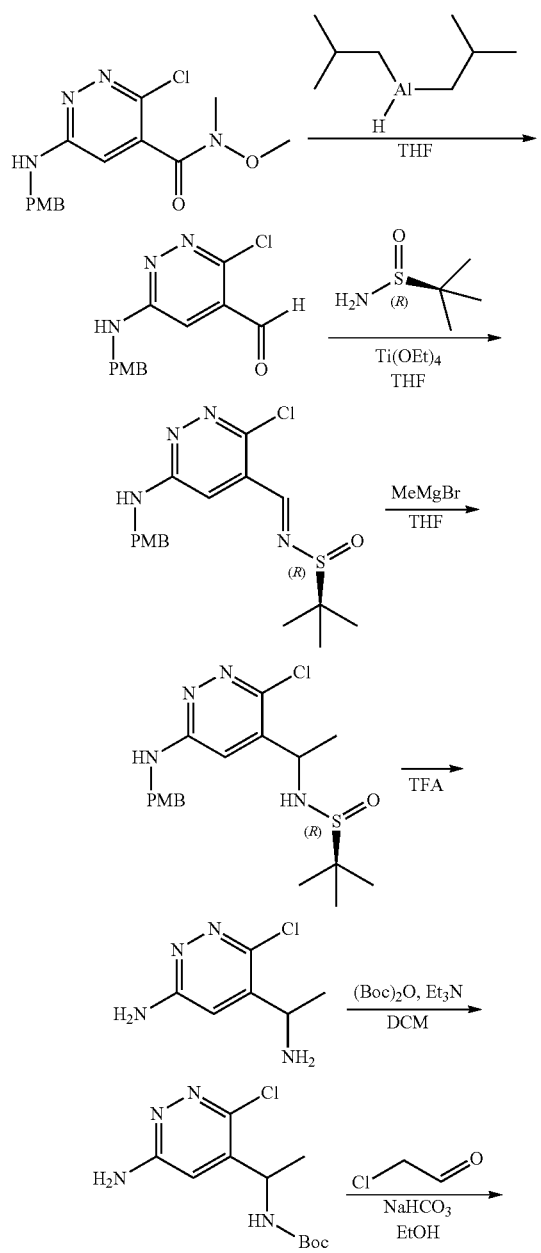

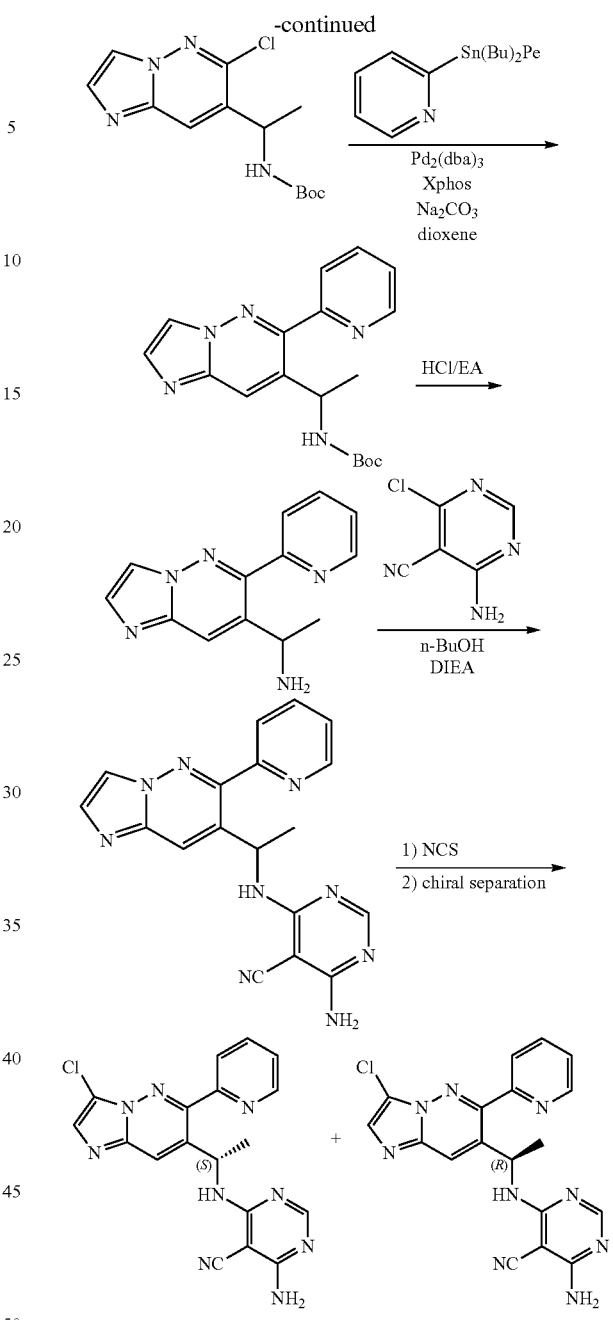

(A) 3-chloro-6-((4-methoxybenzyl)amino)pyridazine-4-carbaldehyde

To a solution of 3-chloro-N-methoxy-6-((4-methoxybenzyl)amino)-N-methylpyridazine-4-carboxamide (10 g, 29.75 mmol) in dry THF (120 mL) was added diisobutyl-aluminum hydride (89 mL, 89.26 mmol) drop wise at 0° C. under nitrogen atmosphere. The mixture was stirred at room temperature for 2 hours. Then the mixture was quenched with sat. NH$_4$Cl solution, filtered, the filtrate was extracted with EA (50 mL×3). The combined organic layer was dried over anhydrous Na$_2$SO$_4$, concentrated and purified by flash column chromatography (PE:EA=4:6) to give 2.4 g of target product. MS (m/z)=310 [M+H]$^+$, 312 [M+2+H]$^+$.

(B) (R,E)-N-((3-chloro-6-((4-methoxybenzyl)amino) pyridazin-4-yl)methylene)-2-methylpropane-2-sulfinamide To a solution of 3-chloro-6-((4-methoxybenzyl)amino) pyridazine-4-carbaldehyde (2.4 g, 8.66 mmol) and (R)-2-methylpropane-2-sulfinamide (1.6 g, 13 mmol) in dry THF (30 mL) was added Ti(OEt)$_4$ (4 g, 17.32 mmol) under nitrogen atmosphere. The mixture was stirred at reflux overnight. The mixture was cooled to room temperature, poured into water (20 mL), filtered and the filtrate was extracted with EA (30 mL×3). The combined organic layer was dried over anhydrous Na$_2$SO$_4$, concentrated and purified by flash column chromatography (PE:EA=4:6) to give 1.4 g of title product. MS (m/z)=381 [M+H]$^+$, 383 [M+2+H]$^+$.

(C) (R)-N-(1-(3-chloro-6-((4-methoxybenzyl)amino) pyridazin-4-yl)ethyl-2-methylpropane-2-sulfinamide To a solution of (R,E)-N-((3-chloro-6-((4-methoxybenzyl)amino)pyridazin-4-yl)methylene)-2-methylpropane-2-sulfinamide (1.4 g, 3.68 mmol) in dry THF (20 mL) was added MeMgBr (3.1 mL, 9.21 mmol) at −5° C.~0° C. under nitrogen atmosphere. The mixture was stirred at 0~10° C. for 2 hours. The mixture was poured into sat. NH$_4$Cl solution, extracted with EA (20 mL×3). The organic layer was concentrated in vacuo to give 1 g of crude title product. MS (m/z)=397 [M+H]$^+$, 399 [M+2+H]$^+$.

(D) 5-(1-aminoethyl)-6-chloropyridazin-3-amine

The solution of (R)-N-(1-(3-chloro-6-((4-methoxybenzyl)amino)pyridazin-4-yl)ethyl)-2-methylpropane-2-sulfinamide (1 g, 2.52 mmol) in TFA (5 mL) was stirred at reflux for 3 hours. Then the mixture was concentrated in vacuo, and the residue was partitioned between sat. NaHCO$_3$ solution and EA. The organic layer was separated and the aqueous layer was extracted with EA (10 mL×4). The combined organic layer was dried over anhydrous Na$_2$SO$_4$, concentrated to give 308 mg of crude title product. MS (m/z)=173 [M+H]$^+$.

(E) tert-butyl (1-(6-amino-3-chloropyridazin-4-yl) ethyl)carbamate

The solution of 5-(1-aminoethyl)-6-chloropyridazin-3-amine (308 mg, 1.79 mmol), (Boc)$_2$O (586 mg, 2.68 mmol) and Et$_3$N (543 mg, 5.37 mmol) in DCM (5 mL) was stirred overnight at room temperature. The mixture was concentrated at 20° C. and the residue was purified by flash column chromatography (MeOH:H$_2$O=4:6) to give 150 mg of title product. MS (m/z)=273 [M+H]$^+$, 275 [M+2+H]$^+$.

(F) tert-butyl (1-(6-chloroimidazo[1,2-b]pyridazin-7-yl)ethyl)carbamate

To a solution of tert-butyl (1-(6-amino-3-chloropyridazin-4-yl)ethyl)carbamate (150 mg, 0.55 mmol) in EtOH (5 mL) was added 2-chloroacetaldehyde (0.245 mL, 1.38 mmol) and NaHCO$_3$ (185 mg, 2.2 mmol). Then the mixture was heated to reflux and stirred overnight. Then the mixture was cooled, concentrated and purified by flash column chromatography (DCM:MeOH=4:96) to give 76 mg of title product. MS (m/z)=297 [M+H]$^+$, 299 [M+2+H]$^+$.

(G) tert-butyl (1-(6-(pyridin-2-yl)imidazo[1,2-b] pyridazin-7-yl)ethyl)carbamate To a solution of tert-butyl (1-(6-chloroimidazo[1,2-b] pyridazin-7-yl)ethyl)carbamate (56 mg, 0.19 mmol) and 2-(dibutyl(pentyl)stannyl)pyridine (140 mg, 0.38 mmol) in dioxane (2 mL) was added Pd$_2$(dba)$_3$ (17 mg, 0.019 mmol), X-phos (18 mg, 0.038 mmol) and Na$_2$CO$_3$ (61 mg, 0.57 mmol) under nitrogen atmosphere. The reaction mixture was heated to reflux and stirred for 4 hours. Then the mixture was cooled, concentrated and purified by flash column chromatography (MeOH:H$_2$O=55:45) to give 20 mg of title product. MS (m/z)=340 [M+H]$^+$.

(H) 1-(6-(pyridin-2-yl)imidazo[1,2-b]pyridazin-7-yl) ethanamine

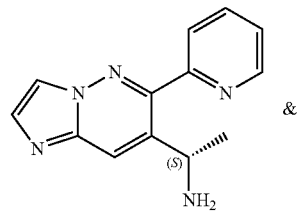

&

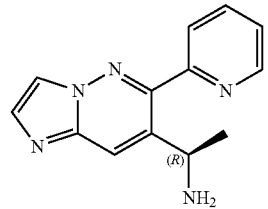

To a solution of tert-butyl (1-(6-(pyridin-2-yl)imidazo[1,2-b]pyridazin-7-yl)ethyl)carbamate (20 mg, 0.059 mmol) in EA/MeOH (20 mL) was added 4N HCl solution in EA (0.059 mL, 0.236 mmol) at 0° C. The mixture was heated to 40° C. and stirred for extra 0.5 hour. Then the mixture was concentrated in vacuo and the residue was purified by flash column chromatography (MeOH/H$_2$O+0.5% NH$_3$H$_2$O) to give 9 mg of title product MS (m/z)=240 [M+H]$^+$.

(I) 4-amino-6-((1-(6-(pyridin-2-yl)imidazo[1,2-b] pyridazin-7-yl)ethyl)amino)pyrimidine-5-carbonitrile To a solution of 1-(6-(pyridin-2-yl)imidazo[1,2-b] pyridazin-7-yl)ethanamine (9 mg, 0.037 mmol) and 4-amino-6-chloropyrimidine-5-carbonitrile (9 mg, 0.056 mmol) in n-BuOH (3 mL) was added DIPEA (24 mg, 0.185 mmol). The mixture was stirred at reflux overnight. The mixture was concentrated in vacuo, and the residue was purified by flash column chromatography (MeOH:H$_2$O=65:35+0.5% NH$_3$H$_2$O) to give 9 mg of title product. MS (m/z)=358 [M+H]$^+$.

(J) (R)-4-amino-6-((1-(3-chloro-6-(pyridin-2-yl)imidazo[1,2-b]pyridazin-7-yl)ethyl)amino)pyrimidine-5-carbonitrile and (S)-4-amino-6-((1-(3-chloro-6-(pyridin-2-yl)imidazo[1,2-b]pyridazin-7-yl)ethyl)amino)pyrimidine-5-carbonitrile The solution of 4-amino-6-((1-(6-(pyridin-2-yl)imidazo[1,2-b]pyridazin-7-yl)ethyl)amino)pyrimidine-5-carbonitrile (9 mg, 0.025 mmol) and NCS (7 mg, 0.05 mmol) in CHCl$_3$ (2 mL) was stirred at reflux for 1 hour. The mixture was cooled to room temperature, concentrated in vacuo, and the residue was purified by chiral prep-HPLC (column: Dalcel IA: 20*250 mm; mobile phase: 100% EtOH+0.1% DEA; flow rate: 8 mL/min; detect wavelength: UV 254 nm;) to give 1.8 mg of compound 7 (Rt=25.2 min) and 2 mg of compound 8 (Rt=29.1 min).

Compound 7: MS (m/z)=392 [M+H]$^+$, $^1$H NMR (400 MHz, CD$_3$OD) δ 8.70 (d, J=4.9 Hz, 1H), 8.16 (s, 1H), 8.01 (td, J=7.8 Hz, 1.8 Hz, 1H), 7.91 (d, J=7.9 Hz, 1H), 7.85 (d, J=1.9 Hz, 1H), 7.79 (s, 1H), 7.53-7.52 (m, 1H), 5.76 (q, J=7.1 Hz, 1H), 1.51 (d, J=7.0 Hz, 3H).

Compound 8: MS (m/z)=392 [M+H]$^+$, $^1$H NMR (400 MHz, CD$_3$OD) δ 8.70 (ddd, J=4.9 Hz, 1.7 Hz, 0.9 Hz, 1H), 8.16 (d, J=0.7 Hz, 1H), 8.01 (td, J=7.7 Hz, 1.8 Hz, 1H), 7.91 (dt, J=7.8 Hz, 1.1 Hz, 1H), 7.84 (s, 1H), 7.79 (s, 1H), 7.54-7.50 (m, 1H), 5.76 (q, J=7.0 Hz, 1H), 1.51 (d, J=7.0 Hz, 3H).

The following compounds were prepared according to the procedures of Compound 7 and 8 using the corresponding intermediates and reagents under appropriate conditions that will be recognized by the POSITA.

Rt of compound 28 is 9.443 min. Rt of compound 29 is 11.080 min. These two compounds were separated according to the conditions in procedure (J) of Compound 7 and 8.

Compound 20

(S)-9-(1-(3-chloro-6-phenylimidazo[1,2-b]pyridazin-7-yl)ethyl)-9H-purin-6-amine

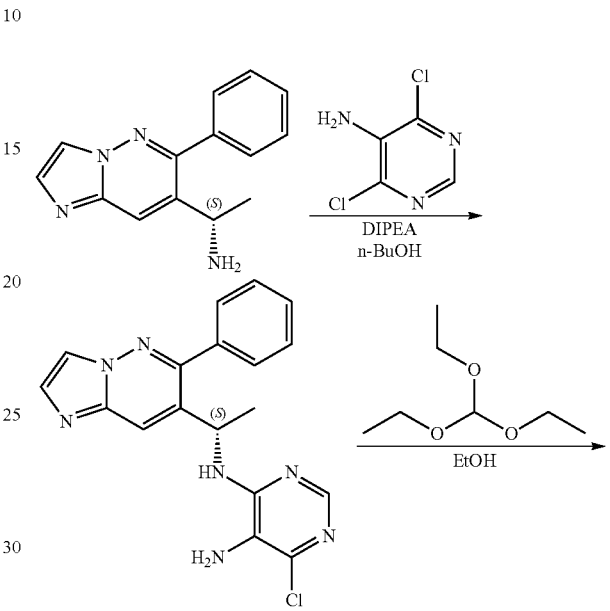

| Compound | Structure | MS (M + H)$^+$ | NMR |
|---|---|---|---|
| 28 | 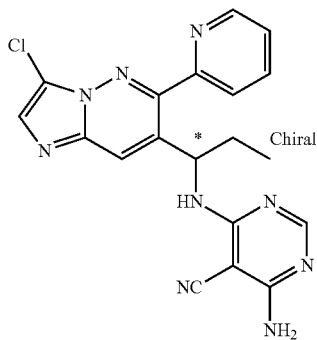 | 406 | $^1$H NMR (400 MHz, DMSO) δ 8.71 (d, J = 4.8, 1H), 8.33 (s, 1H), 8.02 (t, J = 7.7, 1H), 7.92 (s, 1H), 7.87 (t, J = 6.9, 2H), 7.72 (s, 1H), 7.60-7.52 (m, 1H), 7.15 (s, 2H), 5.42-5.33 (m, 1H), 1.87-1.81 (m, 2H), 0.84 (t, J = 7.3, 3H). |
| 29 | 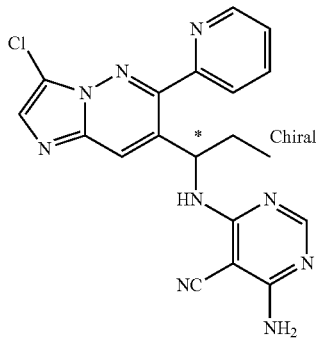 | 406 | $^1$H NMR (400 MHz, DMSO) δ 8.71 (dd, J = 4.9, 0.9, 1H), 8.33 (s, 1H), 8.04-8.01 (m, 1H), 7.92 (s, 1H), 7.89-7.85 (m, 2H), 7.72 (s, 1H), 7.57-7.54 (m, 1H), 7.15 (s, 2H), 5.40-5.34 (m, 1H), 1.90-1.78 (m, 2H), 0.84 (t, J = 7.3, 3H). |

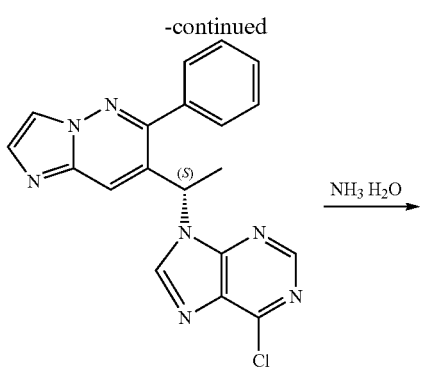

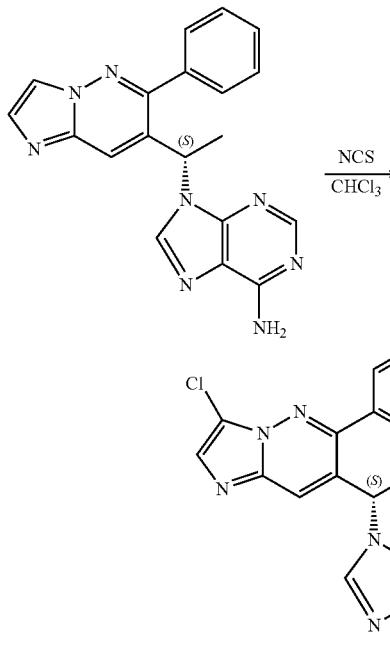

(A) (S)-6-chloro-N⁴-(1-(6-phenylimidazo[1,2-b]pyridazin-7-yl)ethyl)pyrimidine-4,5-diamine The title compound was prepared according to the procedures of compound 4(L).
MS (m/z)=366 [M+H]⁺

(B) (S)-6-chloro-9-(1-(6-phenylimidazo[1,2-b]pyridazin-7-yl)ethyl)-9H-purine

The solution of (S)-6-chloro-N⁴-(1-(6-phenylimidazo[1,2-b]pyridazin-7-yl)ethyl)pyrimidine-4,5-diamine (59 mg, 0.16 mmol) and triethoxymethane (0.5 mL) in EtOH (5 mL) was stirred in reflux for 30 hours. After cooling to room temperature, the mixture was concentrated in vacuo, and the residue was purified by flash column chromatography (MeOH/H₂O+0.5% NH₃.H₂O) to give 42 mg of title product. MS (m/z)=376 [M+H]⁺

(C) (S)-9-(1-(6-phenylimidazo[1,2-b]pyridazin-7-yl)ethyl)-9H-purin-6-amine

A solution of (S)-6-chloro-9-(1-(6-phenylimidazol[1,2-b]pyridazin-7-yl)ethyl)-9H-purine (42 mg, 0.11 mmol) in NH₃.H₂O (2 mL) was reacted in the microwave reactor oven at 110° C. for 30 minutes. Then the mixture was cooled to room temperature, concentrated in vacuo, and the residue was purified by flash column chromatography to give 26 mg of title product. MS (m/z)=357 [M+H]⁺

(D) (S)-9-(1-(3-chloro-6-phenylimidazo[1,2-b]pyridazin-7-yl)ethyl)-9H-purin-6-amine The title compound was prepared according to the procedures of compound 4 (M). MS (m/z)=391 [M+H]⁺
¹H NMR (400 MHz, dmso) δ 8.24 (s, 1H), 7.96 (s, 1H), 7.93 (d, J=5.2 Hz, 2H), 7.45-7.35 (m, 5H), 7.12 (s, 2H), 5.79 (q, J=6.9 Hz, 1H), 1.81 (d, J=7.0 Hz, 3H).

Compound 21

(S)-N⁴-(1-(3-chloro-6-phenylimidazo[1,2-b]pyridazin-7-yl)ethyl-5-(2H-tetrazol-5-yl)pyrimidine-4,6-diamine

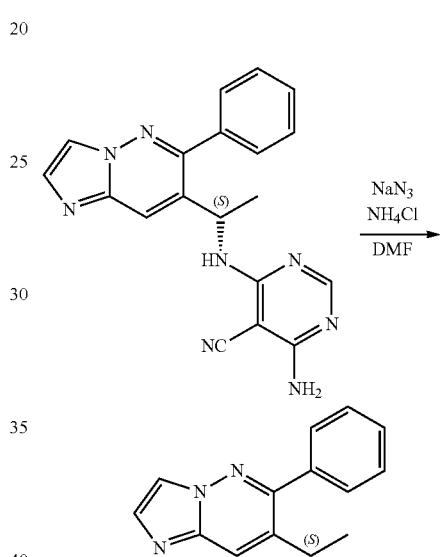

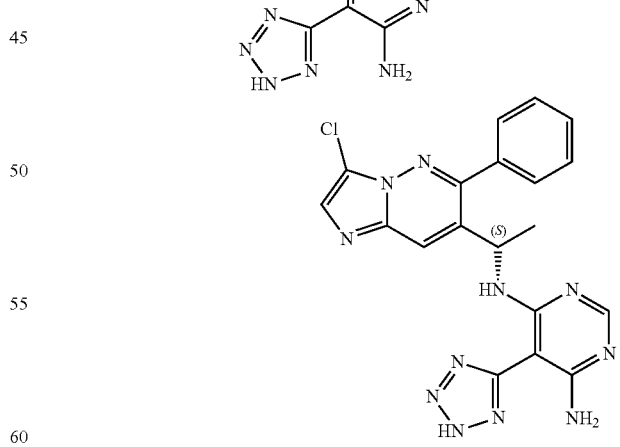

(A) (S)-N⁴-(1-(6-phenylimidazo[1,2-b]pyridazin-7-yl)ethyl)-5-(2H-tetrazol-5-yl)pyrimidine-4,6-diamine The mixture of compound 4 (L) (150 mg, 0.42 mmol), sodium azide (165 mg, 2.55 mmol) and ammonium chloride (135 mg, 2.55 mmol) in dry DMF (4 mL) was sealed in a tube and reacted in the microwave reactor oven at 140° C. for 40 minutes. Then the mixture was cooled to room temperature, concentrated in vacuo, and the residue was purified by flash column chromatography to give 36 mg of title product. MS (m/z)=400 [M+H]$^+$ (B) (S)-N$^4$(1-(3-chloro-6-phenylimidazo[1,2-b]pyridazin-7-yl)ethyl)-5-(2H-tetrazol-5-yl)pyrimidine-4,6-diamine The title compound was prepared according to the procedures of compound 4 (M). MS (m/z)=434 [M+H]$^+$ $^1$H NMR (400 MHz, dmso) δ 8.13 (d, J=6.4 Hz, 2H), 7.90 (s, 1H), 7.67-7.62 (m, 2H), 7.55-7.49 (m, 3H), 5.39-5.23 (m, 1H), 1.50 (d, J=6.8 Hz, 3H).

Compound 27

(S)-7-(1-(3-chloro-6-phenylimidazo[1,2-b]pyridazin-7-yl)ethyl)-7H-pyrrolo[2,3-d]pyrimidin-4-amine

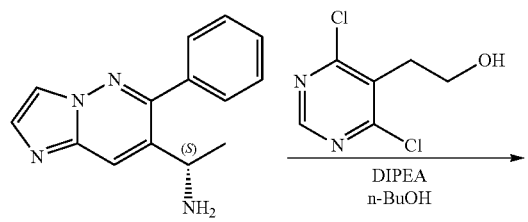

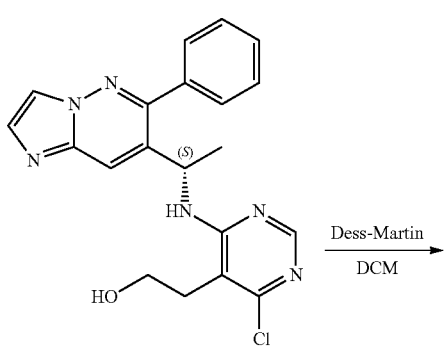

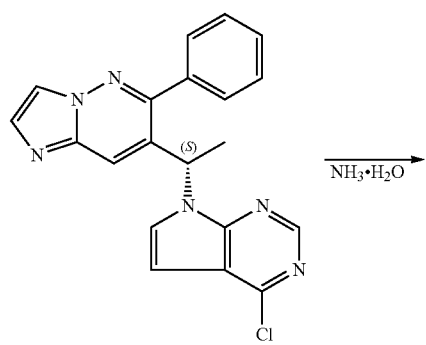

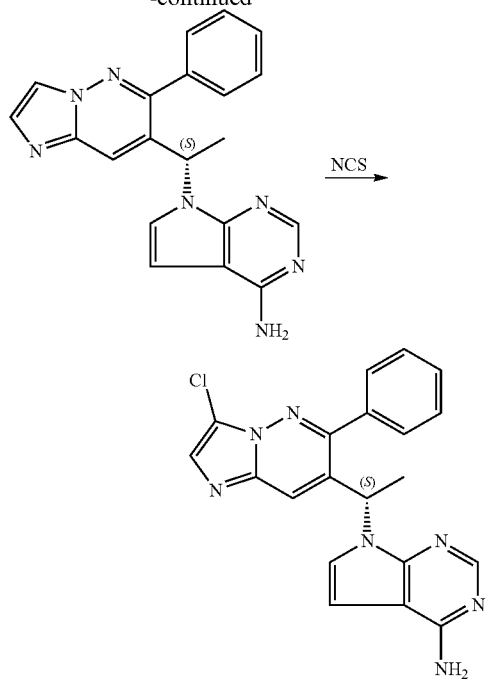

(A) (S)-2-(4-chloro-6-((6-phenylimidazo[1,2-b]pyridazin-7-yl)ethyl)amino)pyrimidin-5-yl)ethanol To a solution of (S)-1-(6-phenylimidazo[1,2-b]pyridazin-7-yl)ethanamine (compound 4(K), 100 mg, 0.42 mmol) and 2-(4,6-dichloropyrimidin-5-yl)ethanol (122 mg, 0.63 mmol) in n-BuOH (5 mL) was added DIPEA (109 mg, 0.84 mmol). The reaction mixture was stirred at 120° C. overnight, and then was stirred at room temperature. The mixture was concentrated in vacuo, and the residue was purified by flash column chromatography (MeOH:H$_2$O+0.5% NH$_3$ H$_2$O) to give 142 mg of product. MS (m/z)=395 [M+H]$^+$.

(B) (S)-4-chloro-7-(1-(6-phenylimidazo[1,2-b]pyridazin-7-yl)ethyl)-7H-pyrrolo[2,3-d]pyrimidine To a solution of (S)-2-(4-chloro-6-((1-(6-phenylimidazo[1,2-b]pyridazin-7-yl)ethyl)amino)pyrimidin-5-yl)ethanol (100 mg, 0.25 mmol) in DCM (10 ml) was added Dess-Martin (322 mg, 0.76 mmol) at 0° C. The mixture was stirred at room temperature for 1.5 hours, and then was poured into sat. Na$_2$S$_2$O$_3$ (10 mL) solution, extracted with DCM (30 mL). The organic layer was concentrated in vacuo, and the residue was purified by flash column chromatography (MeOH:H$_2$O+0.5% NH$_3$.H$_2$O) to give 55 mg of product. MS (m/z)=375 [M+H]$^+$.

(C) (S)-7-(1-(6-phenylimidazo[1,2-b]pyridazin-7-yl)ethyl)-7H-pyrrolo[2,3-d]pyrimidin-4-amine The mixture of (S)-4-chloro-7-(1-(6-phenylimidazo[1,2-b]pyridazin-7-yl)ethyl)-7H-pyrrolo[2,3-d]pyrimidine (55 mg, 0.15 mmol) in ammonia solution (3 mL) was sealed in a reaction tube, irradiated in the microwave reactor at 120° C. for 30 minutes, and then cooled to room temperature. The mixture was concentrated in vacuo, and the residue was purified by flash column chromatography (MeOH:H₂O+ 0.5% NH₃.H₂O) to give 35 mg of product. MS (m/z)=356 [M+H]⁺.

(D) (S)-7-(1-(3-chloro-6-phenylimidazo[1,2-b]pyridazin-7-yl)ethyl)-7H-pyrrolo[2,3-d]pyrimidin-4-amine The title compound was prepared according to the procedures of compound 4 (M). MS (m/z)=390 [M+H]⁺
¹H NMR (400 MHz, CD3OD) δ 8.10 (s, 1H), 7.99 (s, 1H), 7.87 (s, 1H), 7.79-7.78 (m, 1H), 7.27 (s, 5H), 6.98 (s, 1H), 6.11-6.06 (m, 1H), 1.76 (d, J=6.9 Hz, 4H).

Compound 30

(S)-4-amino-6-((1-(3-chloro-6-(3,5-difluorophenyl)imidazo[1,2-b]pyridazin-7-yl)ethyl)amino)pyrimidine-5-carbonitrile

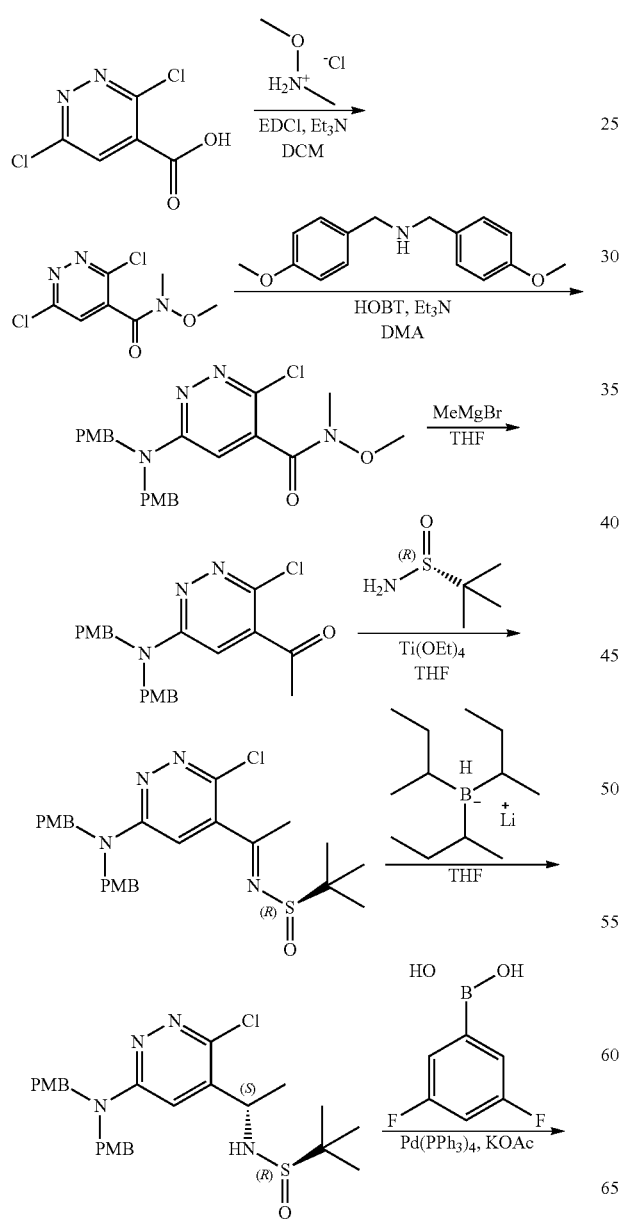

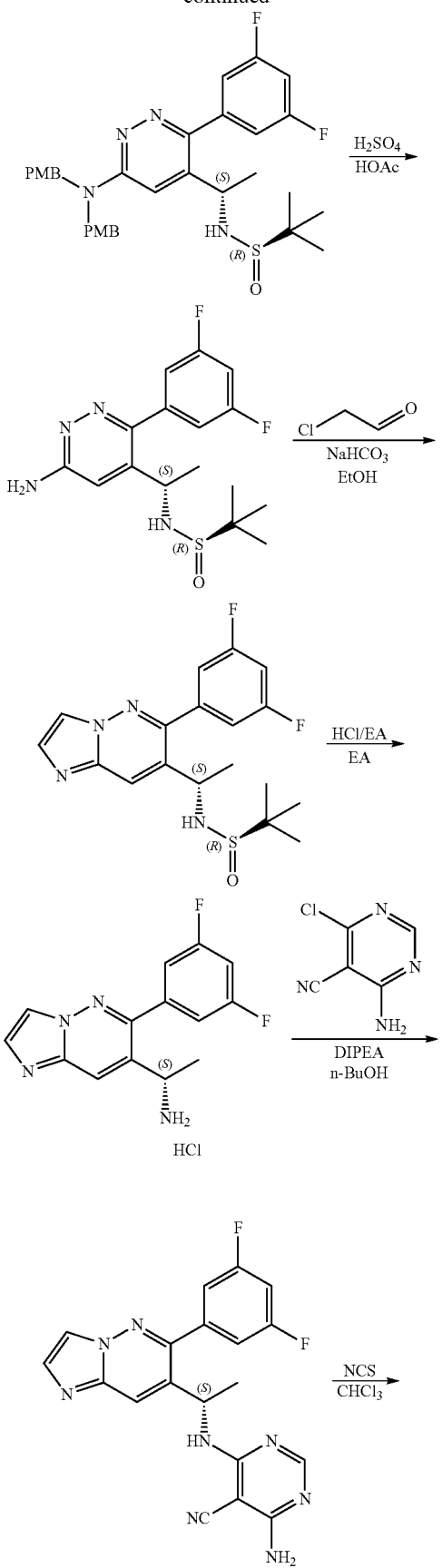

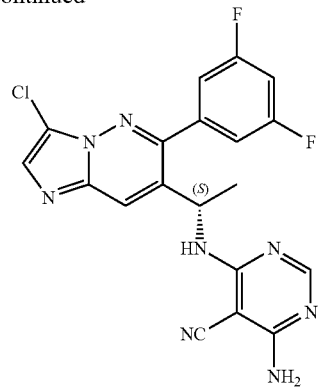

(A) 3,6-dichloro-N-methoxy-N-methylpyridazine-4-carboxamide

To a mixture of 3,6-dichloropyridazine-4-carboxylic add (100.0 g, 0.52 mol), N,O-Dimethylhydroxylamine hydrochloride (60.6 g, 0.62 mol) and EDCl (118.8 g, 0.62 mol) in DCM (800 mL) was dropwise added Et₃N (288 mL, 2.08 mol) at 0° C. Then the reaction mixture was stirred at room temperature overnight. The mixture was washed with saturated NaHCO₃ (1 L) aqueous solution and saturated brine (1 L). The organic layer was separated, dried over anhydrous Na₂SO₄ and concentrated to give 99.7 g of crude product. Yield: 81%. MS (m/z)=236 [M+H]⁺, 238 [M+2+H]⁺

(B) 6-(bis(4-methoxybenzyl)amino)-3-chloro-N-methoxy-N-methylpyridazine-4-carboxamide The solution of 3,6-dichloro-N-methoxy-N-methylpyridazine-4-carboxamide (100 g, 0.42 mol), HOBT (68 g, 0.51 mol) and Et₃N (149 g, 1.48 mot) in DMA (800 ml) was heated to 50° C. After 2 hours, TLC and LC-MS showed the starting material was consumed. Then N,N-Bis(4-methoxybenzyl)amine (163 g, 0.64 mol) was added and the mixture was stirred at 50° C. overnight. Then the mixture was treated with saturated brine (1 L) and extracted with EA (1 L×3). The combined organic layer was dried over anhydrous Na₂SO₄, concentrated and purified by silica-gel column chromatography (PE:EA=3:1 to 1:1) to give 75 g of product. Yield: 40%. MS (m/z)=457 [M+H]⁺.

(C) 1-(6-(bis(4-methoxybenzyl)amino)-3-chloropyridazin-4-yl)ethan-1-one

To a stirred solution of 6-(bis(4-methoxybenzyl)amino)-3-chloro-N-methoxy-N-methylpyridazine-4-carboxamide (9 g, 19.73 mmol) in dry THF (100 mL) was added MeMgBr (9.9 mL, 29.6 mmol) slowly at 5° C.~10° C. under the protection of nitrogen. The mixture was stirred at room temperature for 2 hours. Then the mixture was poured into sat. NH₄Cl (30 mL) aqueous solution, the aqueous layers was extracted with EA (100 mL×2), the organic layer was dried over anhydrous Na₂SO₄ and concentrated in vacuo to give 7.7 g crude product which was prepared for next step without purification. MS (m/z)=412 [M+H]⁺.

(D) (R,E)-N-(1-(6-(bis(4-methoxybenzyl)amino)-3-chloropyridazin-4-yl)ethylidene)-2-methylpropane-2-sulfinamide To a solution of 1-(6-(bis(4-methoxybenzyl)amino)-3-chloropyridazin-4-yl)ethan-1-one (7.7 g, 18.73 mmol) and (R)-(+)-2-Methyl-2-Propanesulfinamide (2.5 g, 20.6 mmol) in dry THF (80 mL) was added Ti(OEt)₄ (6.4 g, 28.1 mmol) dropwise under nitrogen. The mixture was healed to reflux overnight. After cooling to room temperature, the mixture was poured into water (100 mL), the precipitate was filtered and the filtrate was extracted with EA (100 mL×2), the combined organic layer was dried over anhydrous Na₂SO₄, concentrated and purified by flash column chromatography (PE:EA=2:1) to give 7.9 g of target compound as a pale yellow oil. Yield: 81%. MS (m/z)=515 [M+H]⁺.

(E) (R)-N-((S)-1-(6-(bis(4-methoxybenzyl)amino)-3-chloropyridazin-4-yl)ethyl)-2-methylpropane-2-sulfinamide To a solution of LiB(C₄H₇)₃ (39 mL, 38.42 mmol) in dry THF (80 ml) was added (R,E)-N-(1-(6-(bis(4-methoxybenzyl)amino)-3-chloropyridazin-4-yl)ethylidene)-2-methylpropane-2-sulfinamide (7.9 g, 15.37 mmol) at −78° C. under nitrogen. The mixture was stirred at −78° C. for 2 hours. The mixture was poured into sat. NH₄Cl aqueous solution (200 mL), the aqueous layer was extracted with EA (100 mL×2), the organic layer was dried and concentrated in vacuo, and the residue was purified by flash column chromatography (PE:EA=65%:35%) to give 3.8 g compound as a pale yellow oil. Yield: 48%. MS (m/z)=518 [M+H]⁺.

(F) (R)-N-((S)-1-(6-(bis(4-methoxybenzyl)amino)-3-(3,5-difluorophenyl)pyridazin-4-yl)ethyl)-2-methylpropane-2-sulfinamide To a solution of (R)-N-((S)-1-(6-(bis(4-methoxybenzyl)amino)-3-chloropyridazin-4-yl)ethyl)-2-methylpropane-2-sulfinamide (900 mg, 1.74 mmol) and 3,5-difluorophenylboronic acid (551 mg, 3.49 mmol) in dioxane (6 mL) and water (2 ml) was added Pd(PPh₃)₄ (201 mg, 0.174 mmol) and KOAC (511 mg, 5.22 mmol) under nitrogen. The reaction mixture was healed to reflux and stirred overnight. After cooling to room temperature, the mixture was treated with water, extracted with EA (10 mL×2). The organic layer was dried and concentrated in vacuo, the residue was purified by flash column chromatography (PE:EA=7:3) to give 635 mg target compound. Yield: 61%. MS (m/z)=595 [M+H]⁺.

(G) (R)-N-((s)-1-(6-amino-3-(3,5-difluorophenyl)pyridazin-4-yl)ethyl)-2-methylpropane-2-sulfinamide To a solution of (R)-N-((S)-1-(6-(bis(4-methoxybenzyl)amino)-3-(3,5-difluorophenyl)pyridazin-4-yl)ethyl)-2-methylpropane-2-sulfinamide (635 mg, 1.07 mmol) in AcOH (3.2 mL) was added concentrated sulfuric acid (1.6 mL) drop wise at 10° C. The mixture was stirred at room temperature for 2 hours. Then the mixture was slowly treated with the aqueous solution of NaOH (2 M, 45 mL) at 0° C. until pH=8~9, and then extracted with DCM (30 mL×3), the organic layer was dried over anhydrous Na₂SO₄, concentrated and purified by flash column chromatography (MeOH:H₂O=6:4 (+0.5% ammonia)) to give 165 mg target compound. Yield: 44%. MS (m/z)=355 [M+H]⁺.

(H) (R)-N-((S)-1-(6-(3,5-difluorophenyl)imidazo[1,2-b]pyridazin-7-yl)ethyl)-2-methylpropane-2-sulfinamide To a solution of (R)-N-((S)-1-(6-amino-3-(3,5-difluorophenyl)pyridazin-4-yl)ethyl)-2-methylpropane-2-sulfinamide (165 mg, 0.47 mmol) in EtOH (3 mL) was added 2-chloroacetaldehyde (55 mg, 0.70 mmol) and NaHCO$_3$ (79 mg, 0.94 mmol). Then the mixture was heated to reflux and stirred overnight. Then the mixture was cooled, concentrated and purified by flash column chromatography (MeOH: H$_2$O=7:3 (+0.5% ammonia)) to give 150 mg compound as solid. Yield: 84%. MS (m/z)=379 [M+H]$^+$.

(I) (S)-1-(6-(3,5-difluorophenyl)imidazo[1,2-b]pyridazin-7-yl)ethan-1-amine hydrochloride

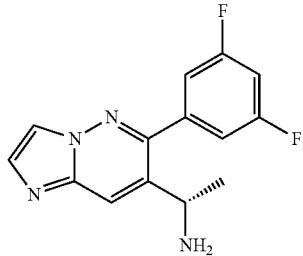 [SMILES: C[C@H](N)c1cc2nccn2nc1-c1cc(F)cc(F)c1]

To a solution of (R)-N-((S)-1-(6-(3,5-difluorophenyl)imidazo[1,2-b]pyridazin-7-yl)ethyl)-2-methylpropane-2-sulfinamide (150 mg, 0.4 mmol) in EA (3 mL) was added HCl-EA (2 mL) at 0° C. The mixture was stirred at room temperature for 1 hour, and then the mixture was concentrated in vacuo to give 99 mg of crude product as pale yellow solid which was used for next step without purification. MS (m/z)=275 [M+H]$^+$.

(J) (S)-4-amino-6-((1-(6-(3,5-difluorophenyl)imidazo[1,2-b]pyridazin-7-yl)ethyl)amino)pyrimidine-5-carbonitrile To a solution of (S)-1-(6-(3,5-difluorophenyl)imidazo[1,2-b]pyridazin-7-yl)ethan-1-amine hydrochloride (99 mg, 0.36 mmol) and 4-amino-6-chloropyrimidine-5-carbonitrile (84 mg, 0.54 mmol) in n-BuOH (3 mL) was added DIPEA (186 mg, 1.44 mmol). The mixture was stirred at reflux overnight. After cooling to room temperature, the mixture was concentrated in vacuo, and the residue was purified by flash column chromatography (MeOH:H$_2$O=55:45 (+0.5% ammonia)) to give 95 mg of target compound as pale yellow solid. Yield: 67%. MS (m/z)=393 [M+H]$^+$.

(K) (S)-4-amino-6-((1-(3-chloro-6-(3,5-difluorophenyl)imidazo[1,2-b]-pyridazin-7-yl)ethyl)amino)pyrimidine-5-carbonitrile The solution of (S)-4-amino-6-((1-(6-(3,5-difluorophenyl)imidazo[1,2-b]pyridazin-7-yl)ethyl)amino)pyrimidine-5-carbonitrile (95 mg, 0.24 mmol) and NCS (35 mg, 0.27 mmol) in CHCl$_3$ (3 mL) was stirred at 70° C. for 2 hours. After cooling to room temperature, the mixture was concentrated in vacuo, and the residue was purified by flash column chromatography (MeOH:H$_2$O=7:3 (+0.5% ammonia)) to give 77 mg of title compound as solid. Yield: 75%. MS (m/z)=427 [M+H]$^+$.

$^1$H NMR (400 MHz, CD$_3$OD) δ 8.10 (t, J=1.8 Hz, 1H), 7.96-7.86 (m, 1H), 7.82-7.72 (m, 1H), 7.40-7.26 (m, 2H), 7.12-6.98 (m, 1H), 5.44 (q, J=6.8 Hz, 1H), 1.48 (d, J=6.9 Hz, 3H).

The following compounds were prepared according to the procedure of Compound 30 using the corresponding intermediates and reagents under appropriate conditions that will be recognized by the POSITA.

| Compound | Structure | MS (M + H)$^+$ | NMR | Intermediate |
|---|---|---|---|---|
| 32 | 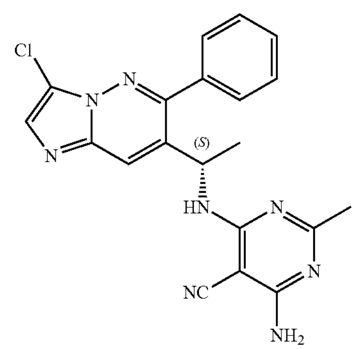 | 405 | $^1$H NMR (400 MHz, CD$_3$OD) δ 8.06 (s, 1H), 7.74-7.67 (m, 3H), 7.53-7.47 (m, 3H), 5.51 (q, J = 7.0 Hz, 1H), 2.17 (s, 3H), 1.39 (d, J = 7.0 Hz, 3H). |  |
| 35 | 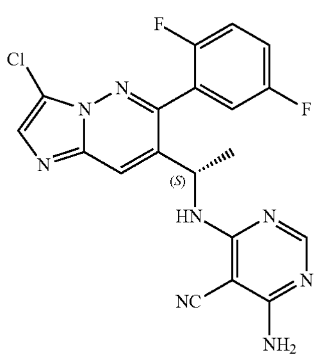 | 427 | $^1$H NMR (400 MHz, CD$_3$OD) δ 8.14 (d, J = 0.7 Hz, 1H), 7.78 (d, J = 3.6 Hz, 2H), 7.31 (dd, J = 9.3, 4.2 Hz, 1H), 7.19 (s, 2H), 5.32 (s, 1H), 1.55 (d, J = 6.9 Hz, 3H). | MS (M + H)$^+$: 275 |

-continued

| Compound | Structure | MS (M + H)+ | NMR | Intermediate |
|---|---|---|---|---|
| 36 | 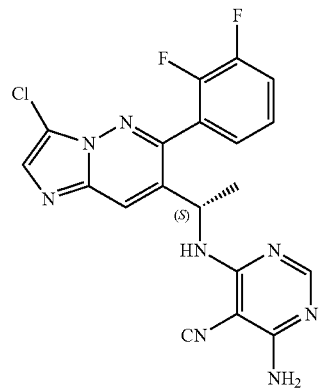 | 427 | ¹H NMR (400 MHz, CD₃OD) δ 8.15 (s, 1H), 7.78 (t, J = 2.6 Hz, 2H), 7.31 (s, 2H), 7.27-7.18 (m, 1H), 5.40-5.28 (m, 1H), 1.55 (d, J = 6.9 Hz, 3H). | MS (M + H)+: 275 |
| 41 | 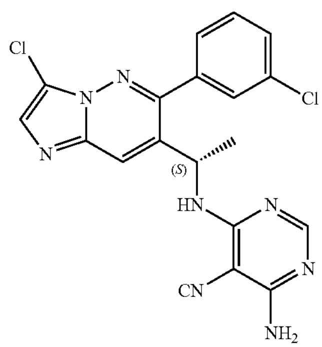 | 425 | ¹H NMR (400 MHz, CD₃OD) δ 8.08 (d, J = 0.7 Hz, 1H), 7.89 (s, 1H), 7.75 (s, 1H), 7.70-7.65 (m, 1H), 7.59-7.54 (m, 1H), 7.48-7.43 (m, 2H), 5.42 (d, J = 6.6 Hz, 1H), 1.46 (d, J = 6.9 Hz, 3H). | MS (M + H)+: 273/275 |
| 45 | 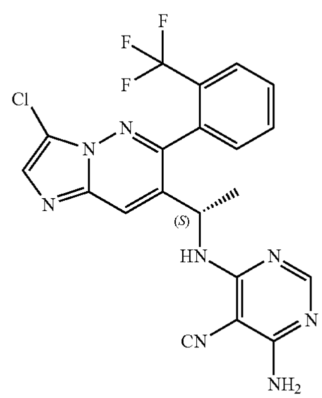 | 459 | ¹H NMR (400 MHz, CD₃OD) δ 8.21 (s, 0.29H), 8.13 (s, 0.67H), 7.86-7.83 (m, 0.65H), 7.80 (s, 0.62H), 7.78 (s, 0.27H), 7.77 (s, 0.61H), 7.73-7.69 (m, 1H), 7.69-7.57 (m, 2.69H), 5.35-5.23 (m, 1H), 1.58 (d, J = 6.8 Hz, 1H), 1.42 (d, J = 6.9 Hz, 2H). | MS (M + H)+: 307 |
| 46 | 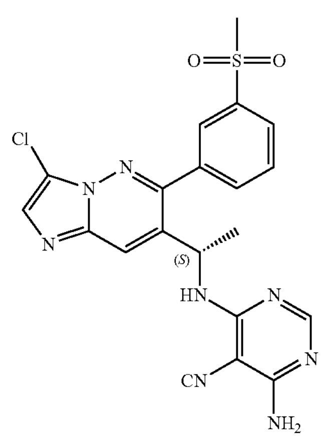 | 469 | ¹H NMR (400 MHz, CD₃OD) δ 8.39 (s, 1H), 8.14 (s, 1H), 8.09-8.04 (m, 1H), 8.01-7.96 (m, 1H), 7.94 (s, 1H), 7.80-7.73 (m, 2H), 5.35 (q, J = 7.0 Hz, 1H), 3.16 (s, 3H), 1.46 (d, J = 6.9 Hz, 3H). | MS (M + H)+: 317 |

-continued

| Compound | Structure | MS (M + H)+ | NMR | Intermediate |
|---|---|---|---|---|
| 48 | 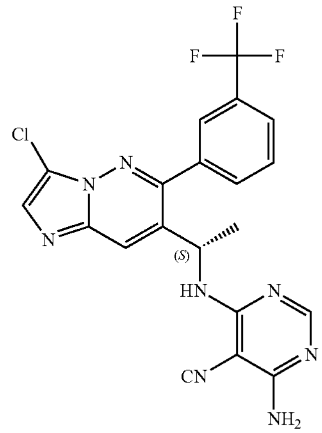 | 459 | ¹H NMR (400 MHz, CD₃OD) δ 8.12 (s, 1H), 8.01 (s, 1H), 7.91 (d, J = 7.6 Hz, 1H), 7.84 (s, 1H), 7.77-7.76 (m, 2H), 7.68 (t, J = 7.7 Hz, 1H), 5.42-5.31 (m, 1H), 1.46 (d, J = 6.9 Hz, 3H). | MS (M + H)+: 307 |
| 49 | 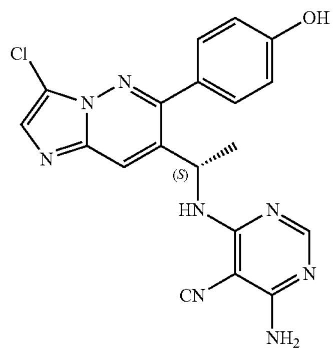 | 407 | ¹H NMR (400 MHz, CD₃OD) δ 7.98 (s, 1H), 7.92 (d, J = 0.5 Hz, 1H), 7.68 (d, J = 0.5 Hz, 1H), 7.52 (dd, J = 6.6, 5.0 Hz, 2H), 6.90 (dd, J = 6.5, 5.0 Hz, 2H), 5.48 (q, J = 6.8 Hz, 1H), 1.38 (d, J = 6.9 Hz, 3H). | MS (M + H)+: 255 |
| 54 | 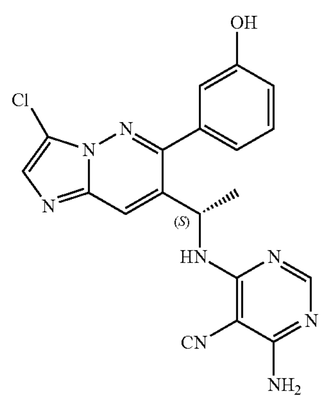 | 407 | ¹H NMR (400 MHz, CD₃OD) δ 8.00 (s, 1H), 7.91 (s, 1H), 7.69 (s, 1H), 7.29-7.25 (m, 1H), 7.10-7.02 (m, 2H), 6.91-6.83 (m, 1H), 5.47 (q, J = 6.8 Hz, 1H), 1.41 (d, J = 6.9 Hz, 3H). | MS (M + H)+: 255 |
| 60 | 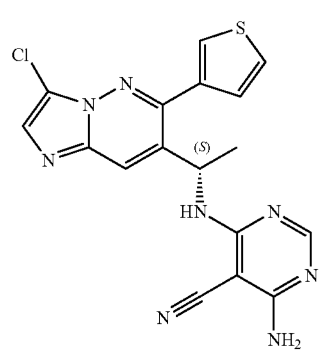 | 397 | ¹H NMR (400 MHz, dmso-6d) δ 8.26 (s, 1H), 7.95 (s, 1H), 7.90 (s, 1H), 7.87 (s, 1H), 7.78 (d, J = 7.3 Hz, 1H), 7.76-7.69 (m, 1H), 7.47 (d, J = 4.0 Hz, 1H), 7.23 (s, 2H), 5.36-5.29 (m, 1H), 1.36 (d, J = 6.9 Hz, 3H). | MS (M + H)+: 245 |

-continued

| Compound | Structure | MS (M + H)+ | NMR | Intermediate |
|---|---|---|---|---|
| 61 | 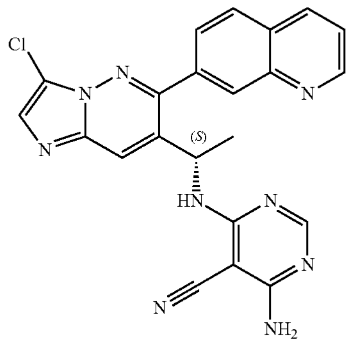 | 442 | ¹H NMR (400 MHz, CD₃OD) δ 8.91 (d, J = 4.0 Hz, 1H), 8.43 (d, J = 7.8 Hz, 1H), 8.29 (s, 1H), 8.13 (s, 1H), 8.07 (d, J = 8.4 Hz, 1H), 7.87 (d, J = 8.4 Hz, 1H), 7.78 (s, 1H), 7.68 (s, 1H), 7.60 (dd, J = 8.3, 4.3 Hz, 1H), 5.54-5.47 (m, 1H), 1.48 (d, J = 6.9 Hz, 4H). | MS (M + H)+: 290 |
| 62 | 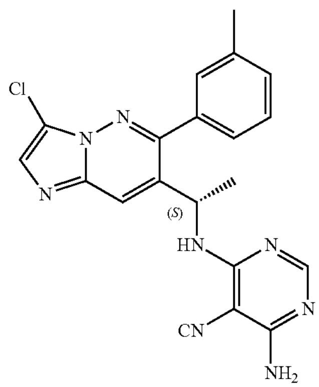 | 405 | ¹H NMR (400 MHz, CD₃OD) δ 8.03 (s, 1H), 7.87 (s, 1H), 7.72 (s, 1H), 7.43-7.38 (m, 2H), 7.34 (t, J = 7.5 Hz, 1H), 7.25 (d, J = 7.3 Hz, 1H), 5.46-5.44 (m, 1H), 2.38 (s, 3H), 1.42 (d, J = 6.9 Hz, 3H). | MS (M + H)+: 253 |
| 63 | 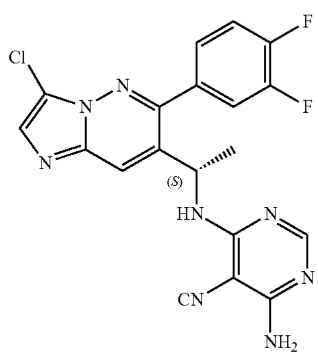 | 427 | ¹H NMR (400 MHz, CD₃OD) δ 8.08 (s, 1H), 7.91 (d, J = 1.3 Hz, 1H), 7.75 (d, J = 1.4 Hz, 1H), 7.70-7.60 (m, 1H), 7.54-7.46 (m, 1H), 7.42-7.38 (m, 1H), 5.41-5.39 (m, 1H), 1.45 (d, J = 6.9 Hz, 3H). | MS (M + H)+: 275 |
| 64 | 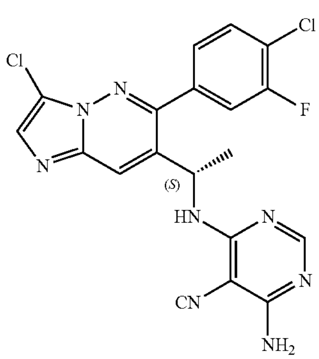 | 443 | ¹H NMR (400 MHz, CD₃OD) δ 8.09 (s, 1H), 7.90 (d, J = 1.2 Hz, 1H), 7.75 (d, J = 1.2 Hz, 1H), 7.64-7.55 (m, 2H), 7.47 (d, J = 8.2 Hz, 1H), 5.42-5.41 (m, 1H), 1.46 (d, J = 6.9 Hz, 3H). | MS (M + H)+: 291 |

| Compound | Structure | MS (M + H)+ | NMR | Intermediate |
|---|---|---|---|---|
| 65 | 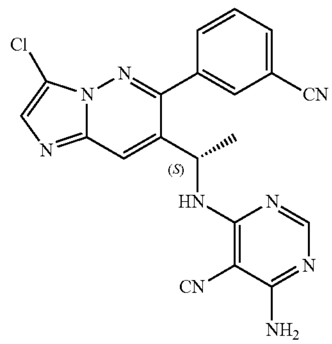 | 416 | 1H NMR (400 MHz, DMSO-6d) δ 8.34 (s, 1H), 8.11 (s, 1H), 8.00-7.88 (m, 3H), 7.84 (s, 1H), 7.71-7.64 (m, 2H), 7.18 (s, 2H), 5.19-5.05 (m, 1H), 1.41 (d, J = 6.8 Hz, 3H). | MS (M + H)+: 264 |
| 66 | 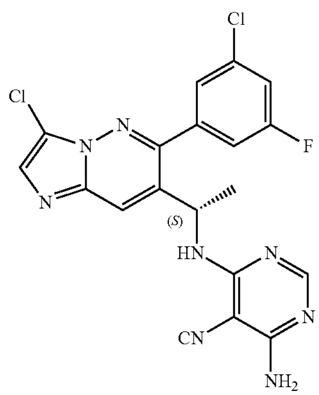 | 443 | 1H NMR (400 MHz, CD3OD) δ 8.10 (s, 1H), 7.90 (s, 1H), 7.77 (s, 1H), 7.52 (s, 1H), 7.42-7.36 (m, 1H), 7.29-7.26 (m, 1H), 5.44 (q, J = 6.8 Hz, 1H), 1.49 (d, J = 6.9 Hz, 3H). | MS (M + H)+: 291 |
| 67 | 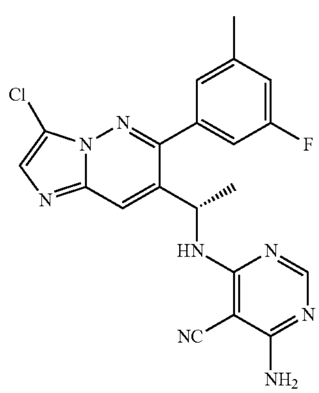 [SMILES: Cc1cc(F)cc(-c2nn3c(Cl)cnc3cc2[C@H](C)Nc2ncnc(N)c2C#N)c1] | 423 | 1H NMR (400 MHz, DMSO-6d) δ 8.27 (s, 1H), 7.90 (d, J = 1.3 Hz, 1H), 7.85 (d, J = 0.8 Hz, 1H), 7.66 (d, J = 7.4 Hz, 1H), 7.26-7.20 (m, 4H), 7.09 (d, J = 10.0 Hz, 1H), 5.21 (t, J = 7.0 Hz, 1H), 2.33 (s, 3H), 1.38 (d, J = 6.7 Hz, 3H). | MS (M + H)+: 271 |
| 68 | 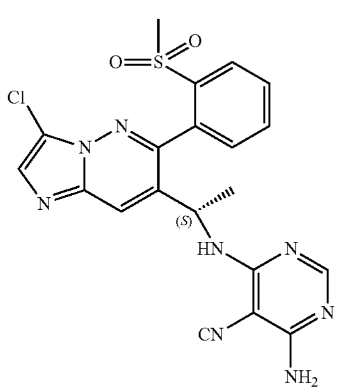 | 469 | 1H NMR (400 MHz, CD3OD) δ 8.25-8.22 (m, 0.27H), 8.20-8.16 (m, 0.74H), 8.10-8.08 (m, 0.76H), 7.96-7.91 (m, 1H), 7.88-7.86 (m, 0.7H), 7.82-7.80 (m, 0.49H), 7.78-7.74 (m, 2.27H), 7.77-7.64 (m, 0.56H), 7.55-7.53 (m, 0.23H), 5.65-5.55 (m, 0.25H), 5.30-5.19 (m, 0.81H), 3.25 (s, 2.12H), 3.23 (s, 0.77H), 1.60 (d, J = 6.8 Hz, 0.7H), 1.41 (d, J = 6.9 Hz, 2.2H). | MS (M + H)+: 317 |

-continued

| Compound | Structure | MS (M + H)+ | NMR | Intermediate |
|---|---|---|---|---|
| 70 | 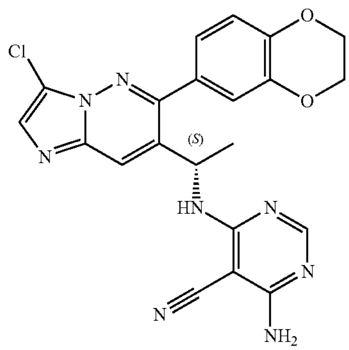 | 449 | ¹H NMR (400 MHz, dmso-6d) δ 8.19 (s, 1H), 7.86 (s, 2H), 7.70 (d, J = 7.4 Hz, 1H), 7.23 (s, 2H), 7.13-7.07 (m, 2H), 6.93 (d, J = 8.2 Hz, 1H), 5.30-5.26 (m, 1H), 4.25 (s, 4H), 1.34 (d, J = 6.9 Hz, 3H). | MS (M + H)+: 297 |
| 71 | 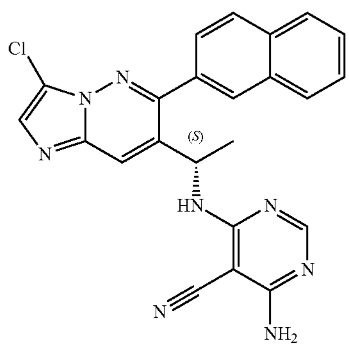 | 441 | ¹H NMR (400 MHz, dmso-6d) δ 8.33 (s, 1H), 8.21 (s, 1H), 8.10-7.95 (m, 3H), 7.92 (s, 1H), 7.85-7.73 (m, 3H), 7.59 (p, J = 6.4 Hz, 2H), 7.21 (s, 2H), 5.22 (t, J = 7.1 Hz, 1H), 1.37 (d, J = 6.9 Hz, 3H). | MS (M + H)+: 289 |
| 72 | 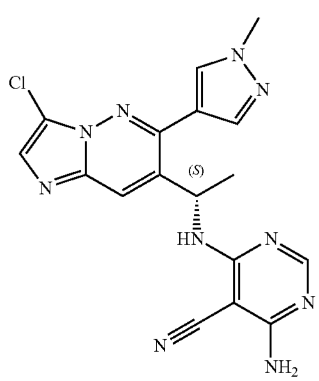 | 395 | ¹H NMR (400 MHz, dmso-6d) δ 8.23 (s, 2H), 7.93 (s, 1H), 7.88-7.84 (m, 3H), 7.28 (s, 2H), 5.50-5.46 (m, 1H), 3.91 (s, 3H), 1.43 (d, J = 6.9 Hz, 3H). | MS (M + H)+: 243 |
| 74 | 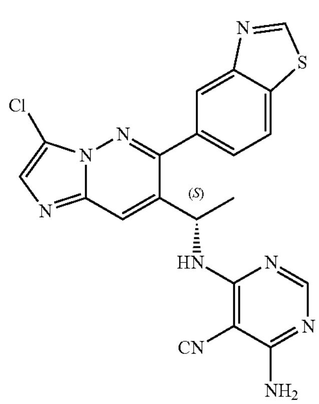 | 448 | ¹H NMR (400 MHz, dmso-6d) δ 9.47 (s, 1H), 8.36 (s, 4H), 8.32 (s, 1H), 8.30 (d, J = 8.3, 1H), 7.92 (s, 1H), 7.78-7.73 (m, 3H), 7.21 (s, 2H), 5.26-5.19 (m, 1H), 1.38 (d, J = 6.9, 4H). | MS (M + H)+: 296 |

-continued

| Compound | Structure | MS (M + H)+ | NMR | Intermediate |
|---|---|---|---|---|
| 75 | 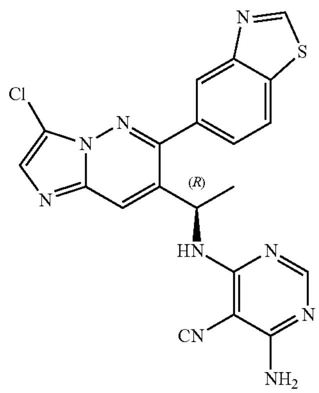 | 448 | ¹H NMR (400 MHz, dmso-6d) δ 9.47 (d, J = 0.8, 1H), 8.36 (s, 1H), 8.32 (s, 1H), 8.29 (d, J = 8.3, 1H), 7.92 (d, J = 1.2, 1H), 7.79-7.72 (m, 3H), 7.21 (s, 2H), 5.25-5.21 (m, 1H), 1.38 (d, J = 6.8, 3H). | MS (M + H)+: 296 |
| 76 | 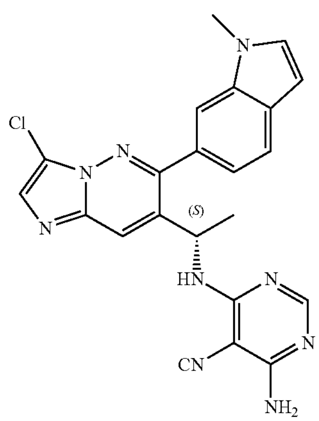 | 444 | ¹H NMR (400 MHz, CDCl₃) δ 8.03 (s, 1H), 7.98 (d, J = 4.7 Hz, 2H), 7.77 (s, 1H), 7.72 (d, J = 8.3 Hz, 1H), 7.65 (s, 1H), 7.47 (d, J = 8.4 Hz, 1H), 7.13 (s, 1H), 5.56-5.49 (m, 1H), 5.44-5.43 (m, 1H), 5.32 (s, 2H), 3.80 (s, 3H), 1.37 (d, J = 6.7 Hz, 3H). | MS (M + H)+: 292 |
| 77 | 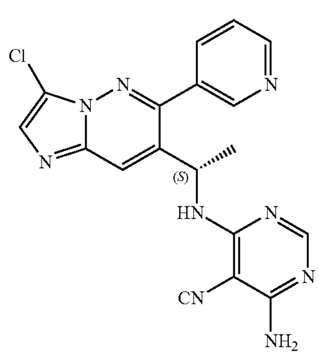 | 392 | ¹H NMR (400 MHz, CD₃OD) δ 8.85 (d, J = 1.5 Hz, 1H), 8.68-8.59 (m, 1H), 8.20-8.18 (m, 1H), 8.15-8.12 (m ,1H), 7.88 (d, J = 1.5 Hz, 1H), 7.78 (d, J = 2.6 Hz, 1H), 7.59-7.55 (m, 1H), 5.36 (q, J = 6.8 Hz, 1H), 1.49 (d, J = 6.9 Hz, 3H). | MS (M + H)+: 293 |

89

Compound 31

(S)-4-amino-6-((1-(3-chloro-6-(o-tolyl)imidazo[1,2-b]pyridazin-7-yl)ethyl)amino)pyrimidine-5-carbonitrile

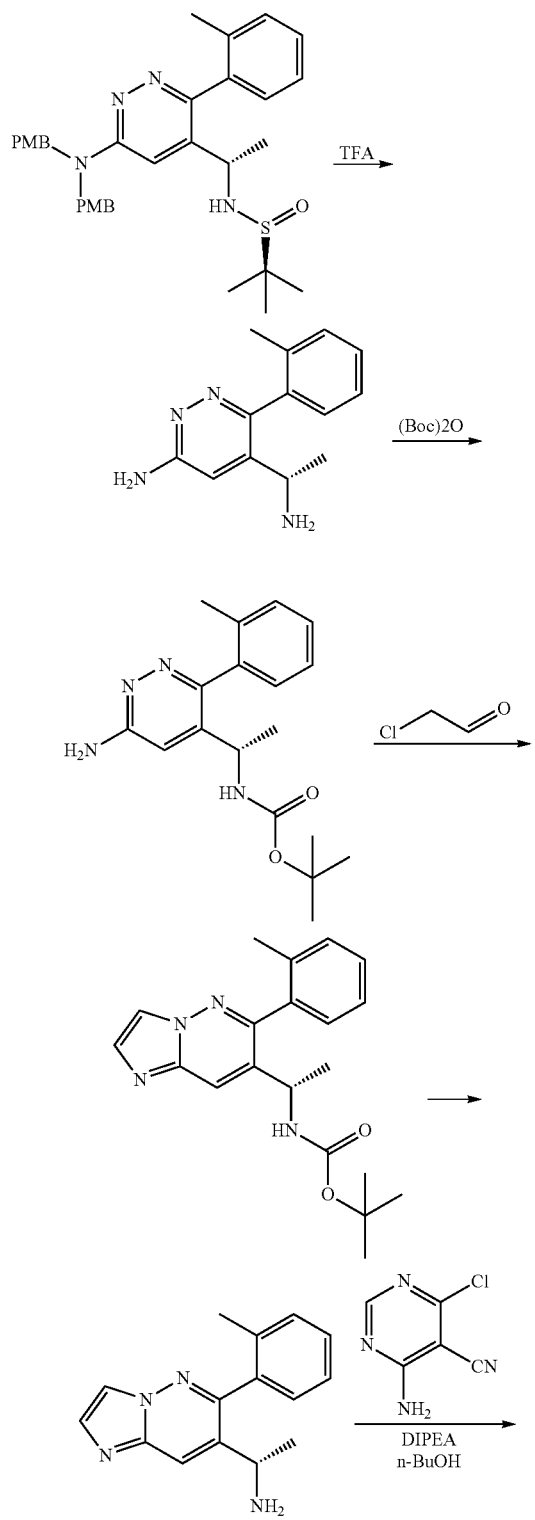

90

-continued

(A) (S)-5-(1-aminoethyl)-6-(o-tolyl)pyridazin-3-amine

The solution of (R)-N-((S)-1-(6-(bis(4-methoxybenzyl)amino)-3-(o-tolyl)pyridazin-4-yl)ethyl)-2-methylpropane-2-sulfinamide (This compound was prepared according to the procedure of Compound 30 (G)) (960 mg, 1.68 mmol) in CF₃COOH (5 mL) was heated and stirred at reflux for 1 hour. After it was cooled to room temperature, the mixture was concentrated in vacuo, adjusted pH=9 with ammonia, concentrated and purified by flash column chromatography (MeOH:H₂O=4:6 (+0.5% ammonia)) to give 140 mg of target compound as pale yellow solid. Yield: 37%. MS (m/z)=229 [M+H]⁺.

(B) tert-butyl (S)-(1-(6-amino-3-(o-tolyl)pyridazin-4-yl)ethyl)carbamate

The solution of (S)-5-(1-aminoethyl)-6-(o-tolyl)pyridazin-3-amine (140 mg, 0.61 mmol) and (Boc)₂O (200 mg, 0.92 mmol) in DCM (2 mL) was stirred overnight at room temperature. Then the mixture was concentrated at 20° C. and the residue was purified by flash column chromatography (MeOH:H₂O=4:6 (+0.5% ammonia)) to give 140 mg of target compound as pale yellow solid. Yield: 70%. MS (m/z)=329 [M+H]⁺.

(C) tert-butyl (S)-(1-(6-(o-tolyl)imidazo[1,2-b]pyridazin-7-yl)ethyl)carbamate This compound was prepared according to the procedure of Compound 30(H). MS (m/z)=353 [M+H]⁺.

(D) (S)-1-(6-(o-tolyl)imidazo[1,2-b]pyridazin-7-yl)ethan-1-amine

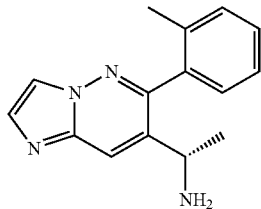 [SMILES: Cc1ccccc1-c1nn2ccnc2cc1[C@H](C)N]

This compound was prepared according to the procedure of Compound 30 (I). MS (m/z)=253 [M+H]⁺.

(E) (S)-4-amino-6-((1-(6-(o-tolyl)imidazo[1,2-b]pyridazin-7-yl)ethyl)amino)pyrimidine-5-carbonitrile This compound was prepared according to the procedure of Compound 30(J). MS (m/z)=371 [M+H]⁺.

(F) (S)-4-amino-6-((1-(3-chloro-6-(o-tolyl)imidazo[1,2-b]pyridazin-7-yl)ethyl)amino)pyrimidine-5-carbonitrile This compound was prepared according to the procedure of Compound 4 (M). MS (m/z)=405 [M+H]⁺.
¹H NMR (400 MHz, CD₃OD) δ 8.08 (s, 1H), 7.90-7.66 (m, 2H), 7.53-7.16 (m, 4H), 5.33-5.22 (m, 1H), 2.25-2.14 (m, 3H), 1.45 (d, J=31.3 Hz, 3H).

The following compounds were prepared according to the procedure of Compound 31 using the corresponding intermediates and reagents under appropriate conditions that will be recognized by the POSITA.

Compound 33

(S)-4-((1-(3-chloro-6-phenylimidazo[1,2-b]pyridazin-7-yl)ethyl)amino)-6-(methylamino)pyrimidine-5-carbonitrile

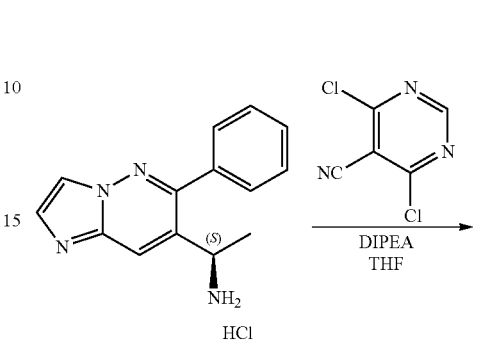

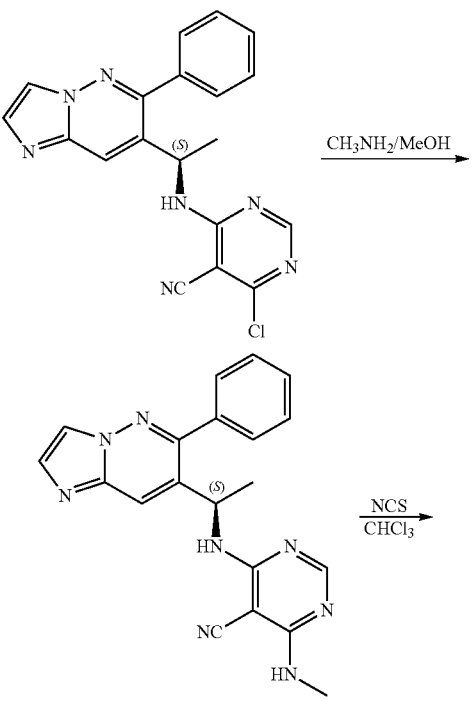

| Compound | Structure | MS (M + H)⁺ | NMR | Intermediate |
|---|---|---|---|---|
| 73 | ![structure] | 392 | ¹H NMR (400 MHz, CD₃OD) δ 8.70-8.66 (m, 2H), 8.16-8.15 (m, 1H), 7.90-7.88 (m, 1H), 7.81-7.78 (m, 1H), 7.78-7.73 (m, 2H), 5.41-5.34 (m, 1H), 1.50 (d, J = 7.1 Hz, 3H). | ![intermediate] MS (M + H)⁺: 240 |

93

-continued

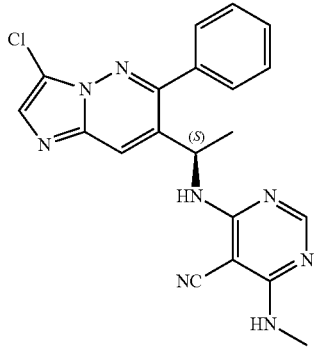

(A) (S)-4-chloro-6-((1-(6-phenylimidazo[1,2-b]pyridazin-7-yl)ethyl)amino)pyrimidine-5-carbonitrile (S)-1-(6-phenylimidazo[1,2-b]pyridazin-7-yl)ethan-1-amine was prepared according to the procedure of Compound 30 (I). The title compound was prepared according to the procedure of Compound 30 (J). MS (m/z)=376 [M+H]$^+$.

94

(B) (S)-4-(methylamino)-6-((1-(6-phenylimidazo[1,2-b]pyridazin-7-yl)ethyl)amino)pyrimidine-5-carbonitrile The mixture of (S)-4-chloro-6-((1-(6-phenylimidazo[1,2-b]pyridazin-7-yl)ethyl)amino) pyrimidine-5-carbonitrile (55.0 mg, 0.146 mmol) and CH$_3$NH$_2$ (35% in CH$_3$OH) (2 mL) was stirred in microwave reactor at 120° C. for 1.5 hours. After concentration, the residue was purified by flash column chromatograph with (H$_2$O:MeOH=3:2-2:3) to give 15.0 mg of the product as white solid. Yield 28%. MS (m/z)=371 [M+H]$^+$.

(C) (S)-4-((1-(3-chloro-6-phenylimidazo[1,2-b]pyridazin-7-yl)ethyl)amino)-6-(methylamino)pyrimidine-5-carbonitrile This compound was prepared according to the procedure of Compound 4 (M). MS (m/z)=405 [M+H]$^+$.

$^1$H NMR (400 MHz, CD$_3$OD) δ 8.03 (s, 1H), 7.96 (s, 1H), 7.70 (s, 1H), 7.69-7.65 (m, 2H), 7.51-7.45 (m, 3H), 5.42 (q, J=6.9 Hz, 1H), 2.90 (s, 3H), 1.38 (d, J=6.9 Hz, 3H).

The following compounds were prepared according to the procedure of Compound 33 using the corresponding intermediates and reagents under appropriate conditions that will be recognized by the POSITA.

| Compound | Structure | MS (M + H)$^+$ | NMR |
| --- | --- | --- | --- |
| 34 | 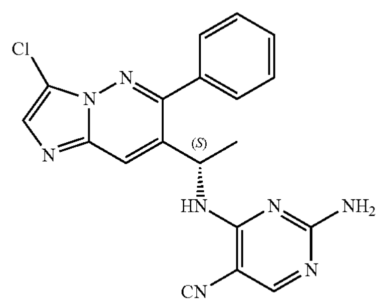 | 391 | $^1$H NMR (400 MHz, CD$_3$OD) δ 8.08 (s, 1H), 8.01 (s, 1H), 7.71-7.66 (m, 3H), 7.53-7.48 (m, 3H), 5.24 (q, J = 6.7 Hz, 1H), 1.29 (d, J = 6.7 Hz, 3H). |
| 40 | 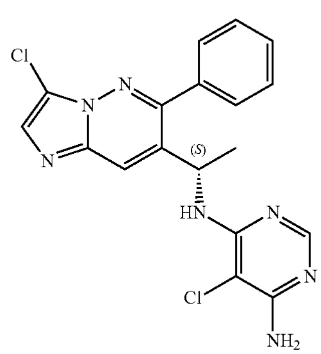 | 400, 402 | $^1$H NMR (400 MHz, dmso-6d) δ 8.19 (s, 1H), 7.85 (s, 1H), 7.71 (s, 1H), 7.68-7.66 (m, 2H), 7.55-7.47 (m, 3H), 7.01 (d, J = 7.5 Hz, 1H), 6.48 (s, 2H), 5.15-5.11 (m, 1H), 1.31 (d, J = 7.0 Hz, 3H). |

Compound 37

(S)-N⁴-(1-(3-chloro-6-phenylimidazo[1,2-b]pyridazin-7-yl)ethyl)-5-(3-fluorophenyl)pyrimidine-4,6-diamine

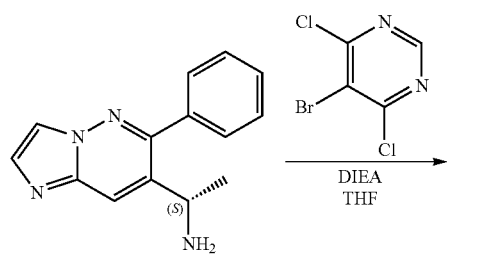

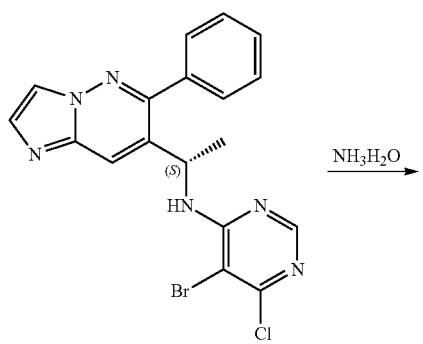

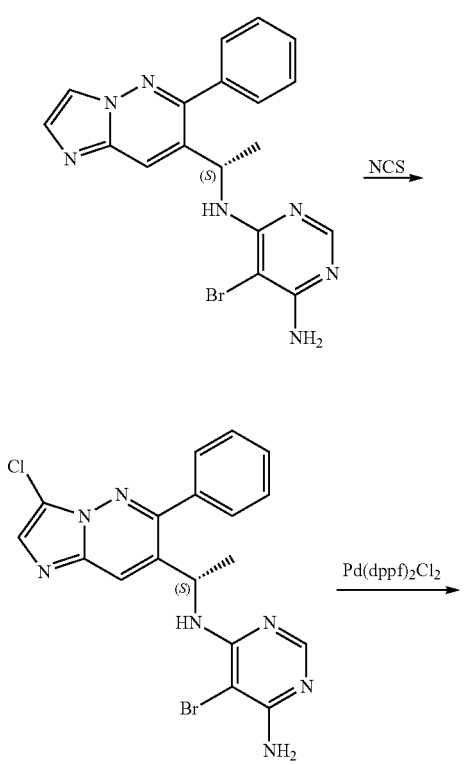

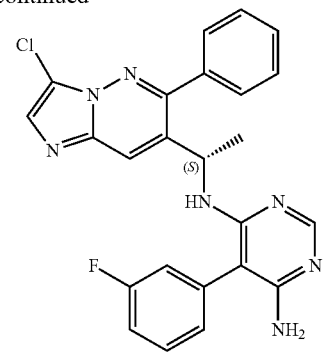

(A) (S)-5-bromo-6-chloro-N-(1-(6-phenylimidazo[1,2-b]pyridazin-7-yl)ethyl)pyrimidin-4-amine This compound was prepared according to the procedure of Compound 30(J). MS (m/z)=431 [M+H]⁺.

(B) (S)-5-bromo-N⁴-(1-(6-phenylimidazo[1,2-b]pyridazin-7-yl)ethyl)pyrimidine-4,6-diamine The mixture of (S)-5-bromo-6-chloro-N-(1-(6-phenylimidazo[1,2-b]pyridazin-7-yl)ethyl)pyrimidin-4-amine (850 mg, 1.97 mmol), ammonium hydroxide solution (5 mL, 36%), and EtOH (2 mL) was irradiated in the microwave reactor at 150° C. for 4 hours. After cooling to room temperature, the mixture was concentrated in vacuo to give 1 g crude product which was used for the next step without purification. MS (m/z)=441 [M+H]⁺.

(C) (S)-5-bromo-N⁴-(1-(3-chloro-6-phenylimidazo[1,2-b]pyridazin-7-yl)ethyl)pyrimidine-4,6-diamine This compound was prepared according to the procedure of Compound 4(M). MS (m/z)=446 [M+H]⁺.

(D) (S)-N⁴-(1-(3-chloro-6-phenylimidazo[1,2-b]pyridazin-7-yl)ethyl)-5-(3-fluorophenyl)pyrimidine-4,6-diamine This compound was prepared according to the procedure of Compound 30(F). MS (m/z)=460 [M+H]⁺.
$^1$H NMR (400 MHz, CD$_3$OD) δ 7.92 (s, 1H), 7.88 (s, 1H), 7.76-7.64 (m, 3H), 7.62-7.45 (m, 4H), 7.25-7.04 (m, 3H), 5.37 (q, J=7.0 Hz, 1H), 1.20 (d, J=6.9 Hz, 3H).

The following compounds were prepared according to the procedure of Compound 37 using the corresponding intermediates and reagents under appropriate conditions that will be recognized by the POSITA.

| Compound | Structure | MS (M + H)+ | NMR |
|---|---|---|---|
| 38 | 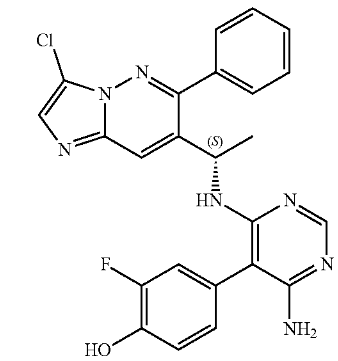 | 476 | ¹H NMR (400 MHz, CD₃OD) δ 7.94 (s, 1H), 7.90 (s, 1H), 7.68 (m, 3H), 7.51 (m, 3H), 7.01-7.12 (m, 3H), 5.33 (q, J = 6.9 Hz, 1H), 1.20 (d, J = 6.9 Hz, 3H). |
| 39 | 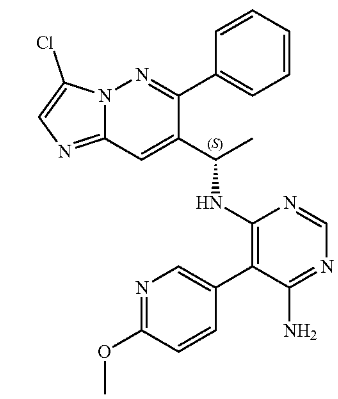 | 473 | ¹H NMR (400 MHz, CD₃OD) δ 8.03 (s, 1H), 7.97 (s, 1 H), 7.92 (s, 1H), 7.75-7.66 (m, 3H), 7.60 (s, 1H), 7.56-7.47 (m, 3H), 6.96 (d, J = 8.4 Hz, 1H), 5.37 (q, J = 6.9 Hz, 1H), 3.94 (s, 3H), 1.22 (d, J = 6.9 Hz, 3H). |
| 50 | 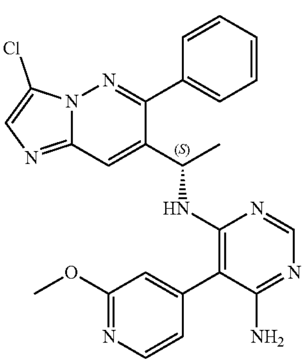 | 473 | ¹H NMR (400 MHz, CD₃OD) δ 8.25 (d, J = 4.2 Hz, 1H), 7.90-7.88 (m, 2H), 7.76-7.61 (m, 3H), 7.52 (m, 3H), 6.89 (d, J = 5.2 Hz, 1H), 6.78 (s, 1H), 5.37 (q, J = 6.9 Hz, 1H), 3.93 (s, 3H), 1.21 (d, J = 6.9 Hz, 3H). |
Compound 42
(S)-4-amino-6-((1-(3-chloro-6-phenylimidazo[1,2-b]pyridazin-7-yl)ethyl)methyl)amino)pyrimidine-5-carbonitrile
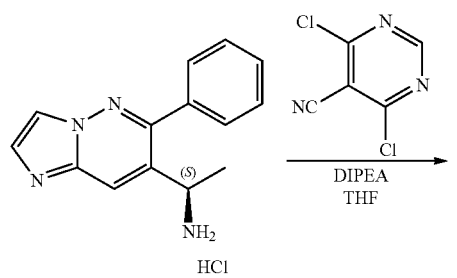
-continued
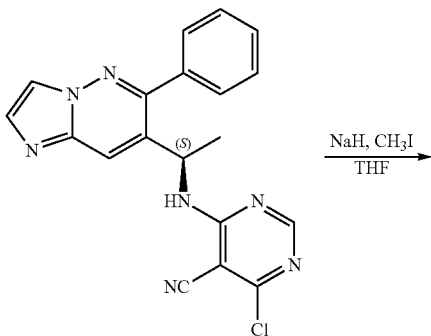

-continued

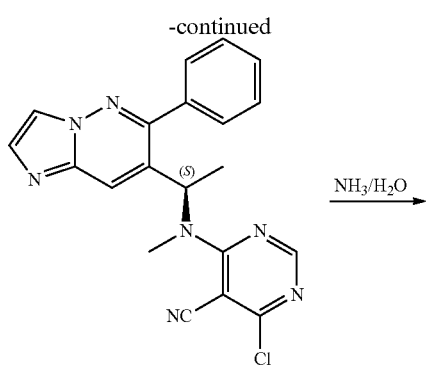

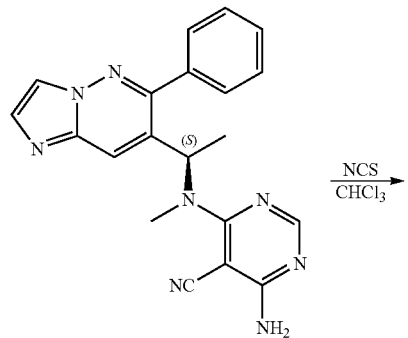

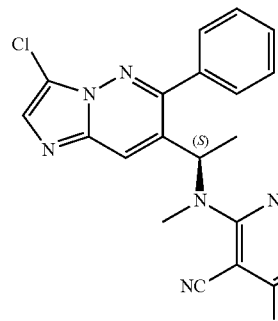

(A) (S)-4-chloro-6-((1-(6-phenylimidazo[1,2-b]pyridazin-7-yl)ethyl)amino)pyrimidine-5-carbonitrile This compound was prepared according to the procedure of Compound 30(J). MS (m/z)=376 [M+H]⁺.

(B) (S)-4-chloro-6-(methyl(1-(6-phenylimidazo[1,2-b]pyridazin-7-yl)ethyl)amino)pyrimidine-5-carbonitrile (S)-4-chloro-6-((1-(6-phenylimidazo[1,2-b]pyridazin-7-yl)ethyl)amino) pyrimidine-5-carbonitrile (70 mg, 0.19 mmol) was dissolved in anhydrous THF (4 mL). The mixture was cooled to 0° C., and then to which was added NaH (60% suspended in mineral oil, 11.2 mg, 0.28 mmol). After stirring at room temperature for 0.5 hour, the mixture was cooled to 0° C. again, and then to which was added CH₃I (39.6 mg, 0.28 mmol) dropwise. The mixture was stirred at room temperature overnight. The mixture was added H₂O (8 mL) and stirred for 5 minutes, then extracted by DCM. The combined organic layers was concentrated and the residue was purified by flash column chromatograph with (DCM: MeOH=19:1-9:1) to give 32.0 mg product as white solid. Yield 45%. MS (m/z)=386 [M+H]⁺.

(C) (S)-4-amino-6-(methyl(1-(6-phenylimidazo[1,2-b]pyridazin-7-yl)ethyl)amino)pyrimidine-5-carbonitrile This compound was prepared according to the procedure of Compound 37(B). MS (m/z)=371 [M+H]⁺.

(D) (S)-4-amino-6-((1-(3-chloro-6-phenylimidazo[1,2-b]pyridazin-7-yl)ethyl)(methyl)amino)pyrimidine-5-carbonitrile This compound was prepared according to the procedure of Compound 4(M). MS (m/z)=405 [M+H]⁺.
¹H NMR (400 MHz, CD₃OD) δ 8.12 (d, J=1.0 Hz, 1H), 7.78 (s, 1H), 7.75 (s, 1H), 7.43-7.37 (m, 2H), 7.31-7.23 (m, 3H), 6.25 (q, J=6.7 Hz, 1H), 2.77 (s, 3H), 1.62 (d, J=6.7 Hz, 3H).

Compound 43

(R)-4-amino-6-((1-(3-chloro-6-(3-fluorophenyl)imidazo[1,2-b]pyridazin-7-yl)propyl)amino)pyrimidine-5-carbonitrile

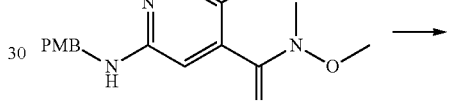

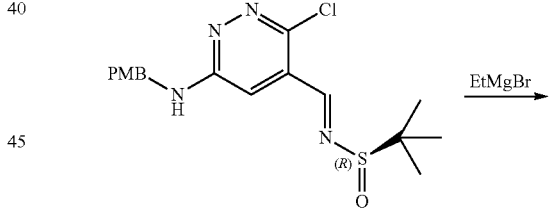

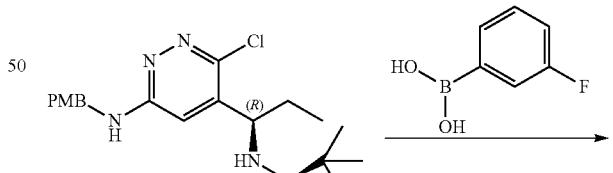

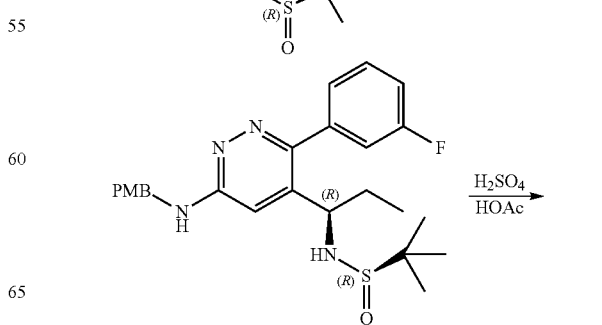

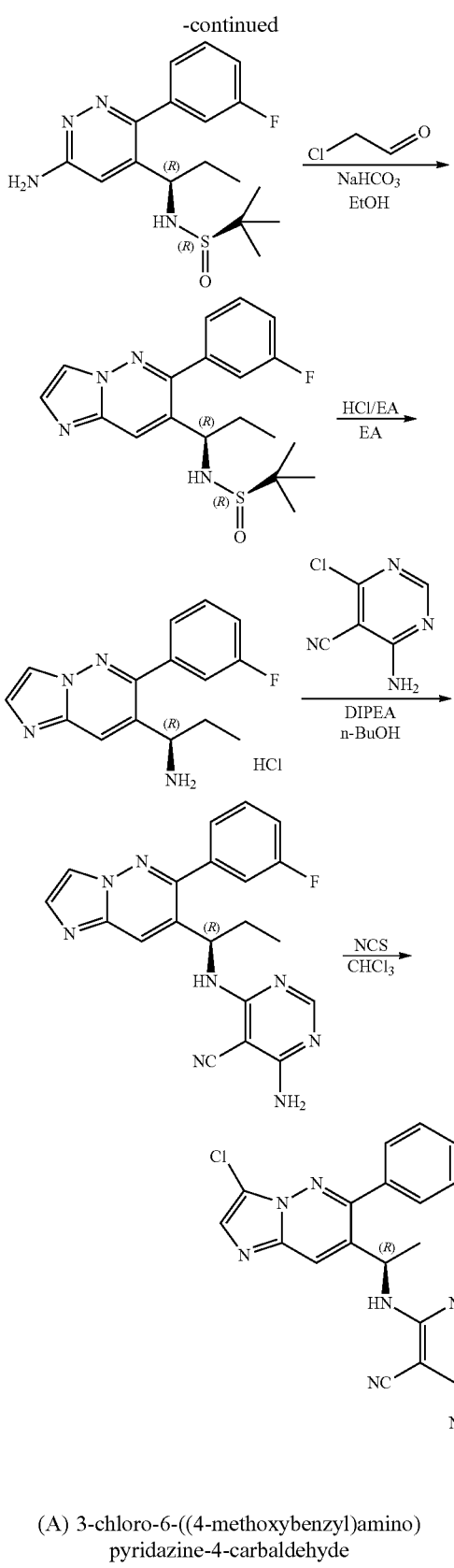

(A) 3-chloro-6-((4-methoxybenzyl)amino)pyridazine-4-carbaldehyde

This compound was prepared according to the procedure of Compound 7 and 8 (A). MS (m/z)=310 [M+H]+, 312 [M+2+H]+.

(B) (R,E)-N-((3-chloro-6-((4-methoxybenzyl)amino)pyridazin-4-yl)methylene)-2-methylpropane-2-sulfinamide This compound was prepared according to the procedure of Compound 7 and 8 (B). MS (m/z)=381 [M+H]+, 383 [M+2+H]+.

(C) (R)-N-(1-(3-chloro-6-((4-methoxybenzyl)amino)pyridazin-4-yl)ethyl)-2-methylpropane-2-sulfinamide This compound was prepared according to the procedure of Compound 7 and 8 (C). MS (m/z)=411 [M+H]+, 413 [M+2+H]+.

(D) (R)-N-((R)-1-(3-(3-fluorophenyl)-6-((4-methoxybenzyl)amino)pyridazin-4-yl)propyl)-2-methylpropane-2-sulfinamide This compound was prepared according to the procedure of Compound 4 (C). MS (m/z)=471 [M+H]+

(E) (R)-N-((R)-1-(6-amino-3-(3-fluorophenyl)pyridazin-4-yl)propyl)-2-methylpropane-2-sulfinamide (R)-N-((R)-1-(3-(3-fluorophenyl)-6-((4-methoxybenzyl)amino)pyridazin-4-yl)propyl)-2-methylpropane-2-sulfinamide (1.1 g, 2.34 mmol) was dissolved in HOAc (5.5 mL). The mixture was cooled to 10° C. and was slowly added conc. H2SO4 (2.75 mL) drop wise. After stirring at room temperature for 1 hour, the mixture was added drop wise to the solution of NaOH (8.0 g) in ice water (100 mL) and stirred for 5 minutes, and then extracted with DCM (100 mL). The combined organic layers was concentrated and the residue was purified by flash column chromatograph (H2O: MeOH=3:2-2:3 (+0.5% NH3.H2O)) to give 545.0 mg of target product as pale brown solid. Yield 66%. MS (m/z)=351 [M+H]+.

(F) (R)-N*((R)-1-(6-(3-fluorophenyl)imidazo[1,2-b]pyridazin-7-yl)propyl)-2-methylpropane-2-sulfinamide This compound was prepared according to the procedure of Compound 4 (J). MS (m/z)=375 [M+H]+.

(G) (R)-1-(6-(3-fluorophenyl)imidazo[1,2-b]pyridazin-7-yl)propan-1-amine hydrochloride

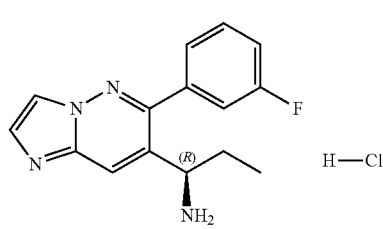

This compound was prepared according to the procedure of Compound 4 (K). MS (m/z)=271 [M+H]+.

(H) (R)-4-amino-6-((1-(6-(3-fluorophenyl)imidazo[1,
2-b]pyridazin-7-yl)propyl)amino)pyrimidine-5-car-
bonitrile This compound was prepared according to the procedure of Compound 4 (L). MS (m/z)=389 [M+H]+.

(I) (R)-4-amino-6-((1-(3-chloro-6-(3-fluorophenyl)
imidazo[1,2-b]pyridazin-7-yl)propyl)amino)pyrimi-
dine-5-carbonitrile This compound was prepared according to the procedure of Compound 4 (M). MS (m/z)=423 [M+H]+.
$^1$H NMR (400 MHz, CD$_3$OD) δ 8.06 (s, 1H), 7.91 (d, J=0.9 Hz, 1H), 7.73 (d, J=0.9 Hz, 1H), 7.55-7.48 (m, 3H), 7.28-7.21 (m, 1H), 5.24 (q, J=5.2 Hz, 1H), 1.89-1.70 (m, 2H), 0.83 (t, J=7.3 Hz, 3H).

The following compounds were prepared according to the procedure of Compound 43 using the corresponding intermediates and reagents under appropriate conditions that will be recognized by the POSITA.

Compound 51

(S)-6-amino-4-((1-(3-chloro-6-phenylimidazo[1,2-b]
pyridazin-7-yl)ethyl)amino)-5-cyanopyrimidine
1-oxide

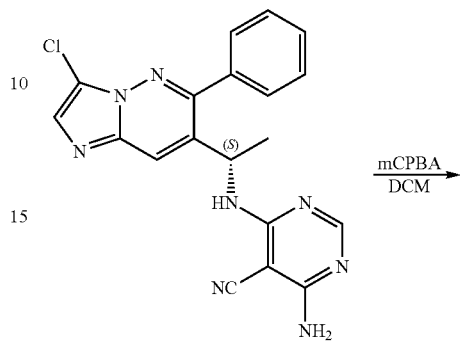

| Compound | Structure | MS (M + H)+ | NMR |
|---|---|---|---|
| 44 | 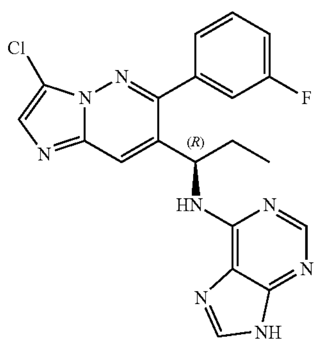 | 423 | $^1$H NMR (400 MHz, CD$_3$OD) δ 8.17 (s, 1H), 8.08-8.07 (m, 2H), 7.69 (s, 1H), 7.64-7.62 (m, 2H), 7.56-7.48 (m, 1H), 7.28-7.20 (m, 1H), 5.50-5.28 (m, 1H), 1.81 (p, J = 7.2 Hz, 2H), 0.87 (t, J = 7.3 Hz, 3H). |
| 47 | 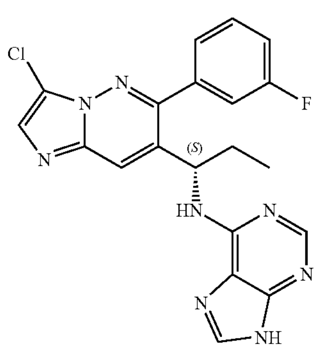 | 423 | $^1$H NMR (400 MHz, CD$_3$OD) δ 8.17 (s, 1H), 8.08 (s, 2H), 7.70 (s, 1H), 7.67-7.59 (m, 2H), 7.57-7.50 (m, 1H), 7.29-7.22 (m, 1H), 5.46-5.26 (m, 1H), 1.82 (p, J = 7.2 Hz, 2H), 0.89 (t, J = 7.3 Hz, 3H). |

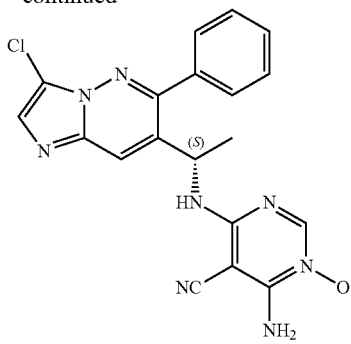

To a solution of compound 4 (40 mg, 0.10 mmol) in DCM (10 mL) was added mCPBA (53 mg, 0.30 mmol) at 5° C. The mixture was stirred at room temperature for 5 hours. The mixture was concentrated in vacuo, and the residue was purified by flash column chromatography (MeOH:H$_2$O (+0.5% NH$_3$.H$_2$O)) to give 15 mg of title compound as white solid. Yield: 36%; MS (m/z)=407 [M+H]$^+$.

$^1$H NMR (400 MHz, CD$_3$OD) δ 8.20 (s, 1H), 8.06 (s, 1H), 7.73 (s, 1H), 7.60-7.58 (m, 2H), 7.50-7.47 (m, 3H), 5.44-5.39 (m, 1H), 1.47 (d, J=6.9 Hz, 3H).

Compound 52

(S)-4-amino-6-((1-(3-chloro-6-phenylimidazo[1,2-b]pyridazin-7-yl)ethyl)amino)pyrimidine-5-carboxylic acid

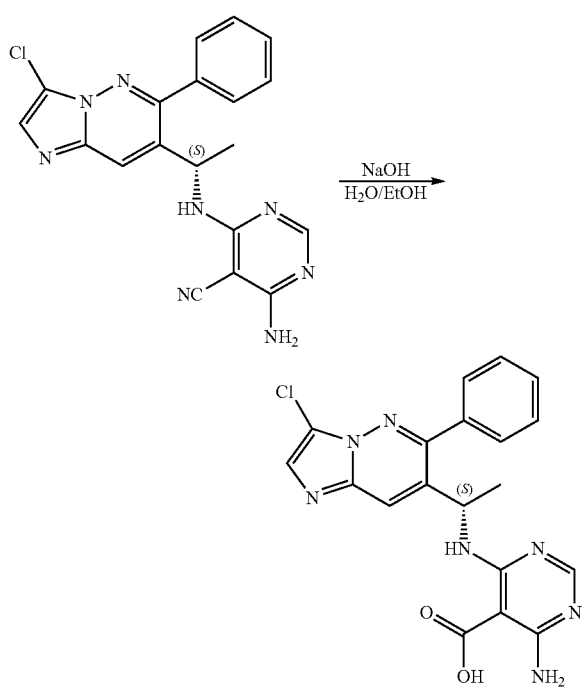

Compound 4 (50.0 mg, 0.13 mmol) was dissolved in aqueous solution of NaOH (2.0 mol/L, 2 mL) and EtOH (0.4 mL) was added. The mixture was stirred at 60° C. overnight, and then cooled to room temperature. Hydrochloric acid (2 mol/L) was added to adjust the pH value to 8~9. The mixture was concentrated and the residue was purified by flash column chromatograph (H$_2$O:MeOH=3:2-1:2) to give 60.0 mg product as white solid. Yield 95%. MS (m/z)=410 [M+H]$^+$.

$^1$H NMR (400 MHz, CD$_3$OD) δ 10.49-10.38 (m, 1H), 7.99 (s, 1H), 7.73-7.68 (m, 3H), 7.68-7.64 (m, 1H), 7.53-7.46 (m, 3H), 5.33-5.22 (m, 1H), 1.31 (d, J=6.8 Hz, 3H).

Compound 53

(S)-4-amino-6-((1-(3-chloro-6-phenylimidazo[1,2-b]pyridazin-7-yl)ethyl)amino)pyrimidine-5-carboxamide

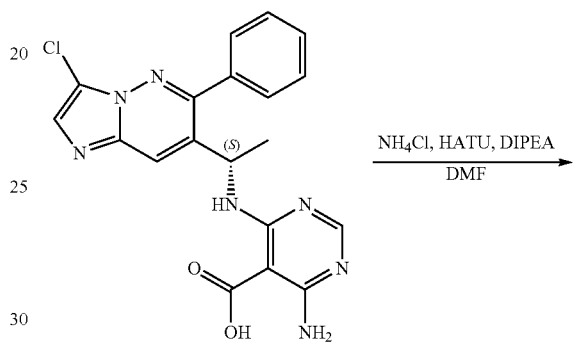

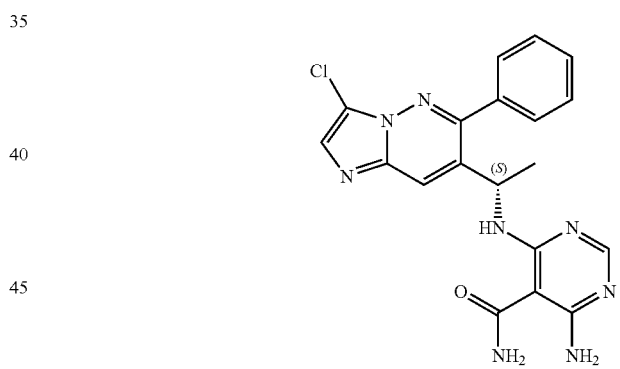

(S)-4-amino-6-((1-(3-chloro-6-phenylimidazo[1,2-b]pyridazin-7-yl)ethyl)amino) pyrimidine-5-carboxylic acid (20.0 mg, 0.049 mmol), NH$_4$Cl (10.4 mg, 0.19 mmol) and HATU (37.2 mg, 0.098 mmol) was dissolved in DMF (2 mL), then DIPEA (12.7 mg, 0.098 mmol) was added slowly. The mixture was stirred at room temperature for 2 hours. The mixture was concentrated and the residue was purified by flash column chromatograph with (H$_2$O:MeOH=1:1-1:4) to give 14.5 mg product as white solid. Yield 72%. MS (m/z)=409 [M+H]$^+$.

$^1$H NMR (400 MHz, CD$_3$OD) δ 8.01-7.97 (m, 1H), 7.82 (s, 1H), 7.73-7.68 (m, 2H), 7.67-7.64 (m, 1H), 7.52-7.47 (m, 3H), 5.33-5.24 (m, 1H), 1.31 (d, J=6.9 Hz, 3H).

The following compounds were prepared according to the procedure of Compound 53 using the corresponding intermediates and reagents under appropriate conditions that will be recognized by the POSITA.

| Compound | Structure | MS (M + H)+ | NMR |
|---|---|---|---|
| 56 | 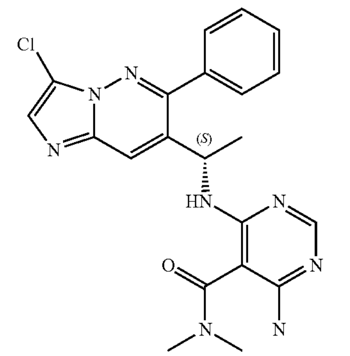 | 437 | ¹H NMR (400 MHz, CD₃OD) δ 8.00 (s, 1H), 7.85 (s, 1H), 7.74-7.69 (m, 2H), 7.69-7.66 (m, 1H), 7.53-7.48 (m, 3H), 5.38-5.31 (m, 1H), 3.05 (s, 3H), 3.03 (s, 3H), 1.30 (d, J = 6.9 Hz, 3H). |
| 57 | 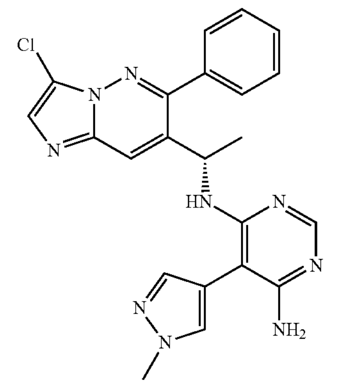 [SMILES: C[C@H](Nc1ncnc(N)c1-c1cnn(C)c1)c1cc2ncc(Cl)n2nc1-c1ccccc1] | 446 | 1 H NMR (400 MHz, cd 3 od) δ 7.92 (s, 1H), 7.85 (s, 1H), 7.76-7.67 (m, 4H), 7.58-7.48 (m, 4H), 5.37-5.32 (m, 1H), 3.97 (s, 3H), 1.22 (d, J = 6.9 Hz, 3H). |
Compound 55
(S)-4-amino-6-((1-(3-chloro-6-phenylimidazo[1,2-b]pyridazin-7-yl)ethyl)amino)-2-hydroxypyrimidine-5-carbonitrile
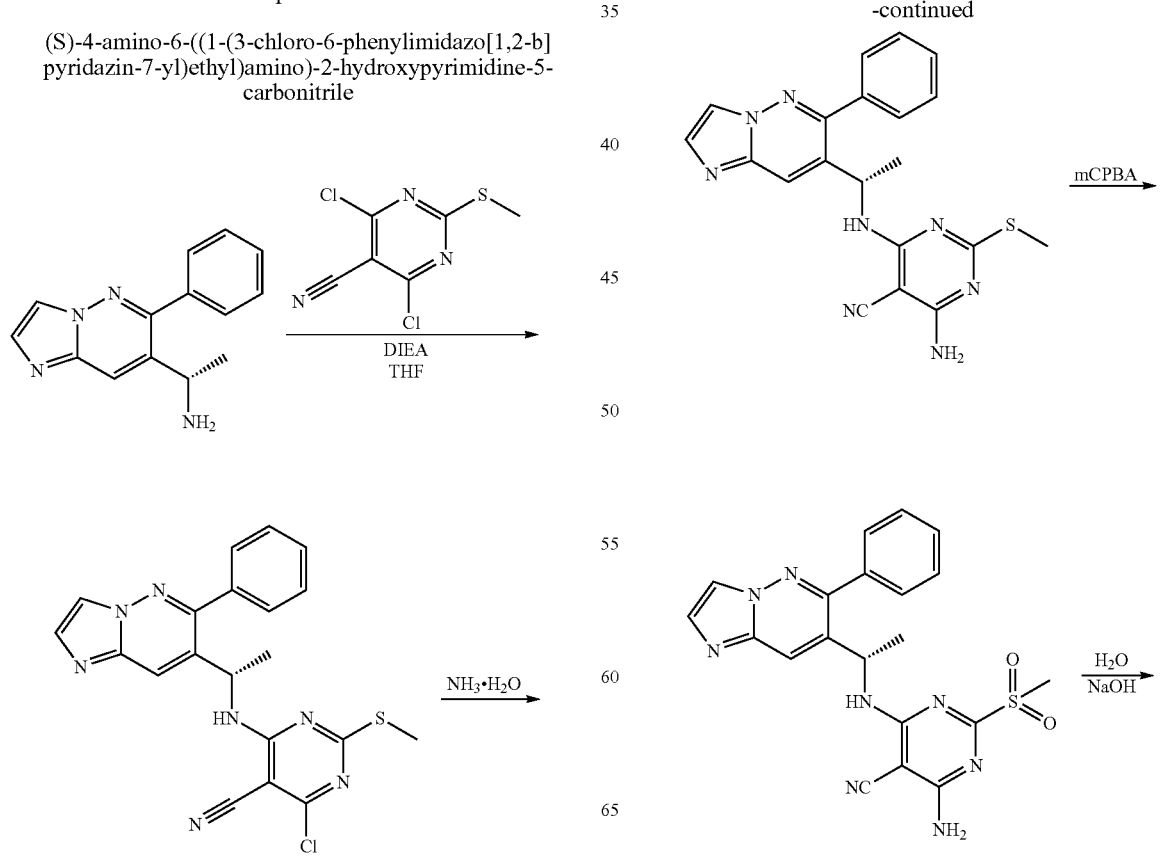
-continued

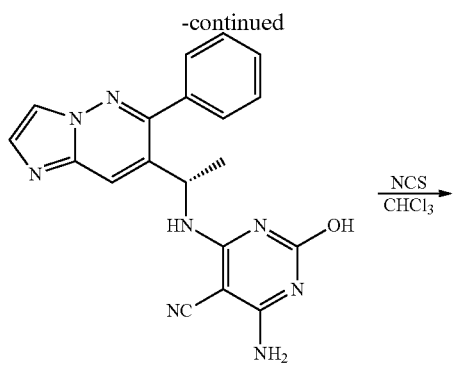

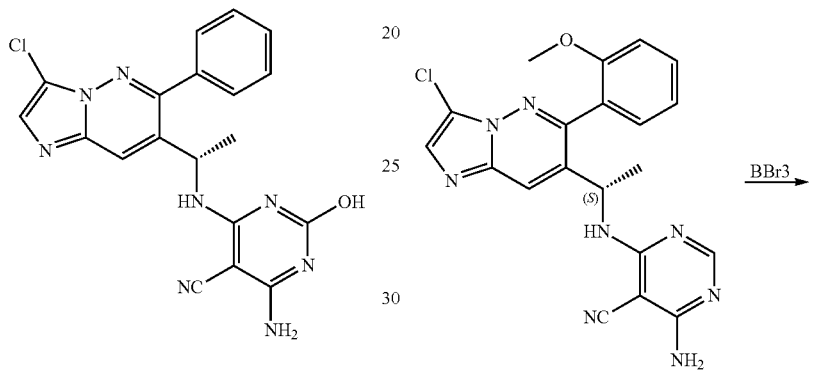

(A) (S)-4-chloro-2-(methylthio)-6-((1-(6-phenylimidazo[1,2-b]Pyridazin-7-yl)ethyl)amino)pyrimidine-5-carbonitrile This compound was prepared according to the procedure of Compound 30(J). MS (m/z)=422 [M+H]+.

(B) (S)-4-amino-2-(methylthio)-6-((1-(6-phenylimidazo[1,2-b]pyridazin-7-yl)ethyl)amino)pyrimidine-5-carbonitrile This compound was prepared according to the procedure of Compound 37 (B). MS (m/z)=403 [M+H]+.

(C) (S)-4-amino-2-(methylsulfonyl)-6-((1-(6-phenylimidazo[1,2-b]pyridazin-7-yl)ethyl)amino)pyrimidine-5-carbonitrile This compound was prepared according to the procedure of Compound 51. MS (m/z)=435 [M+H]+.

(D) (S)-4-amino-2-hydroxy-6-((1-(6-phenylimidazo[1,2-b]pyridazin-7-yl)ethyl)amino)pyrimidine-5-carbonitrile The mixture of (S)-4-amino-2-(methylsulfonyl)-6-((1-(6-phenylimidazo[1,2-b]pyridazin-7-yl)ethyl)amino)pyrimidine-5-carbonitrile (150 mg, 0.34 mmol) and aqueous solution of NaOH (2 mL, 2 N) in THF (5 mL) was stirred at room temperature for 1 hour. The mixture was extracted with DCM (20 mL×3), the combined organic layer was concentrated to give 200 mg crude product which was used for the next step without purification. MS (m/z)=373 [M+H]+.

(E) (S)-4-amino-6-((1-(3-chloro-6-phenylimidazo[1,2-b]pyridazin-7-yl)ethyl)amino)-2-hydroxypyrimidine-5-carbonitrile This compound was prepared according to the procedure of Compound 4 (M). MS (m/z)=407 [M+H]+.

$^1$H NMR (400 MHz, CD$_3$OD) δ 8.00 (s, 1H), 7.78-7.67 (m, 3H), 7.55-7.40 (m, 3H), 5.44 (q, J=6.8 Hz, 1H), 1.36 (d, J=6.9 Hz, 3H).

Compound 69

(S)-4-amino-6-((1-(3-chloro-6-(2-hydroxyphenyl)imidazo[1,2-b]pyridazin-7-yl)ethyl)amino)pyrimidine-5-carbonitrile

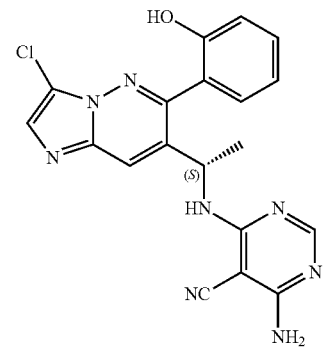

To a solution of (S)-4-amino-6-((1-(3-chloro-6-(2-methoxyphenyl)imidazo[1,2-b]pyridazin-7-yl)ethyl)amino)pyrimidine-5-carbonitrile (120 mg, 0.28 mmol, this compound was prepared according to the procedure of Compound 30) in DCM (3 mL) was added BBr$_3$ (1.4 mL, 1.4 mmol) dropwise at 0° C. The mixture was stirred for 6 hours at room temperature. Then the mixture was quenched with MeOH, concentrated and the residue was purified by flash column chromatograph (MeOH:H$_2$O=7:3) to give 36 mg of title compound as pale yellow solid. Yield: 32%. MS (m/z)=411 [M+H]+.

$^1$H NMR (400 MHz, CD$_3$OD) δ 8.08 (s, 1H), 7.76 (s, 1H), 7.72 (s, 1H), 7.31-7.19 (m, 2H), 6.93-6.82 (m, 2H), 5.39 (d, J=6.9 Hz, 1H), 1.53 (d, J=6.9 Hz, 3H).

111

Compound 78

(S)-4-amino-6-((1-(3-fluoro-6-phenylimidazo[1,2-b]pyridazin-7-yl)ethyl)amino)pyrimidine-5-carbonitrile

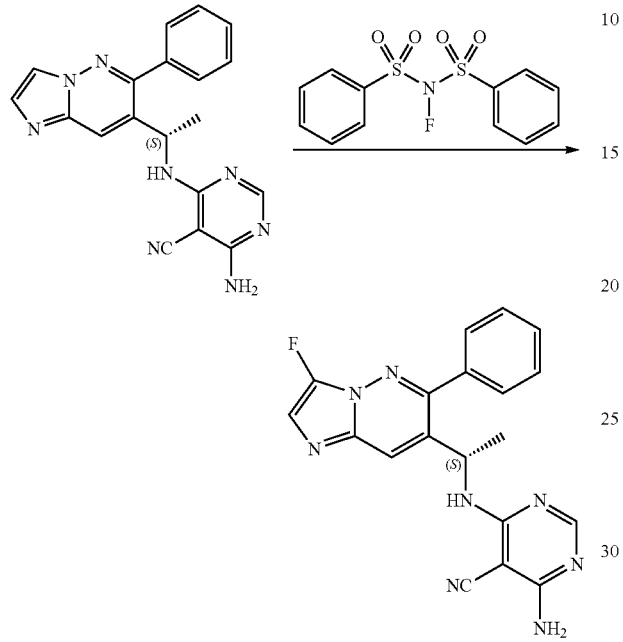

To a solution of (S)-4-amino-6-((1-(6-phenylimidazo[1,2-b]pyridazin-7-yl)ethyl)amino)pyrimidine-5-carbonitrile (100 mg, 0.28 mmol) in CHCl$_3$ (15 mL) was added N-fluoro-N-(phenylsulfonyl)benzenesulfonamide (886 mg, 2.81 mmol). The mixture was stirred at reflux for 32 hours. The mixture was concentrated in vacuo and the residue was purified by thin-layer chromatography to give 5 mg of title compound as white solid. MS (m/z)=375 [M+H]$^+$.

$^1$H NMR (400 MHz, CDCl$_3$) δ 8.05 (s, 1H), 7.87 (d, J=1.4 Hz, 1H), 7.67-7.64 (m, 2H), 7.53-7.49 (m, 3H), 7.49-7.43 (m, 1H), 7.37 (d, J=7.0 Hz, 1H), 5.46-5.31 (m, 3H), 1.37 (d, J=6.8 Hz, 3H).

Compound 79

(chiral)-4-amino-6-((1-(3-chloro-6-(3-(2-hydroxypropan-2-yl)phenyl)imidazo[1,2-b]pyridazin-7-yl)ethyl)amino)pyrimidine-5-carbonitrile

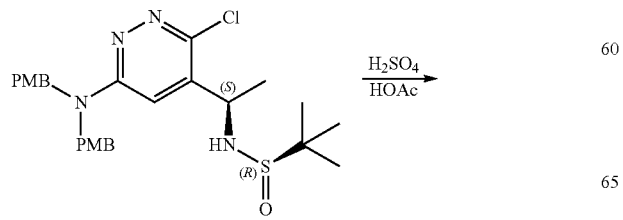

112

-continued

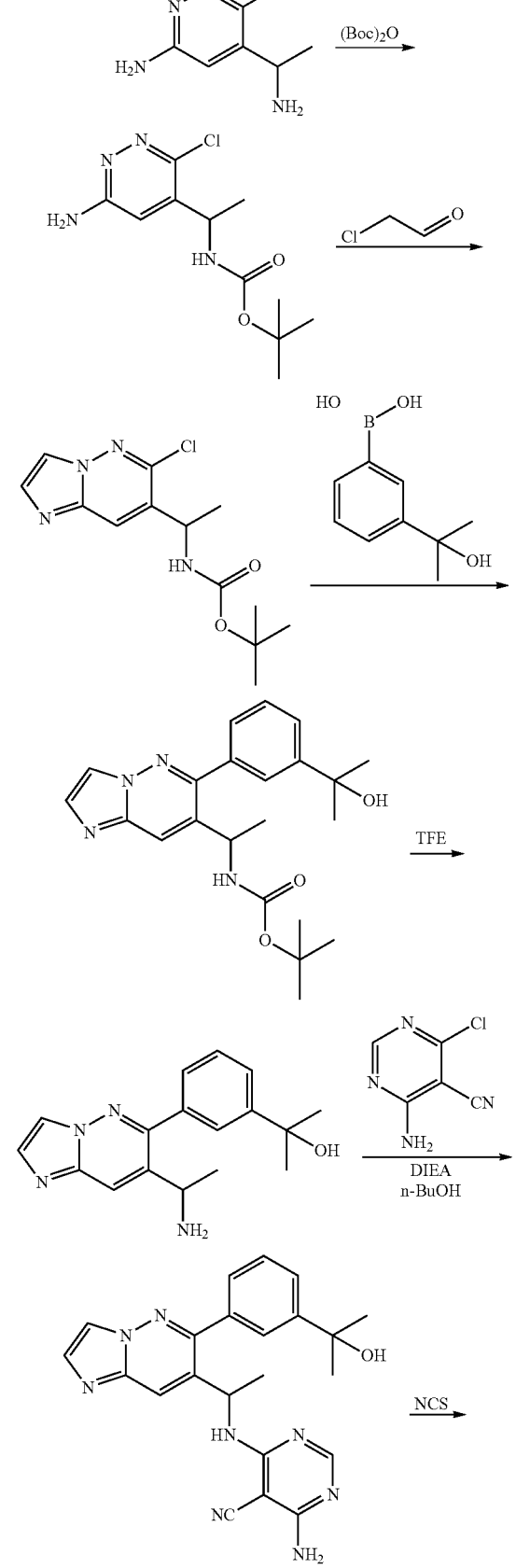

-continued

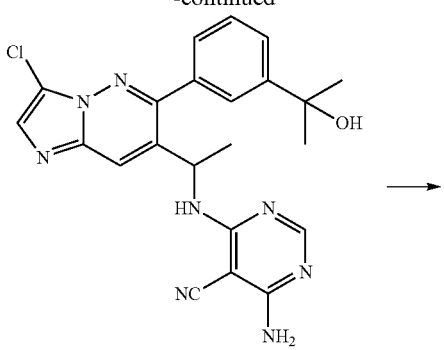

(A) 5-(1-aminoethyl)-6-chloropyridazin-3-amine

This compound was prepared according to the procedure of Compound 30 (G). ((R)-N-(1-(6-(bis(4-methoxybenzyl)amino)-3-chloropyridazin-4-yl)ethyl-2-methylpropane-2-sulfinamide was prepared according to the procedure of compound 30 (E)).

(B) tert-butyl (1-(6-amino-3-chloropyridazin-4-yl)ethyl)carbamate

This compound was prepared according to the procedure of Compound 31 (B).

(C) tert-butyl (1-(6-chloroimidazo[1,2-b]pyridazin-7-yl)ethyl)carbamate

This compound was prepared according to the procedure of Compound 31 (C).

(D) tert-butyl (1-(6-(3-(2-hydroxypropan-2-yl)phenyl)imidazo[1,2-b]pyridazin-7-yl)ethyl)carbamate This compound was prepared according to the procedure of Compound 30 (F). MS (m/z)=397 [M+H]⁺.

(E) 2-(3-(7-(1-aminoethyl)imidazo[1,2b]pyridazin-6-yl)phenyl)propan-2-ol

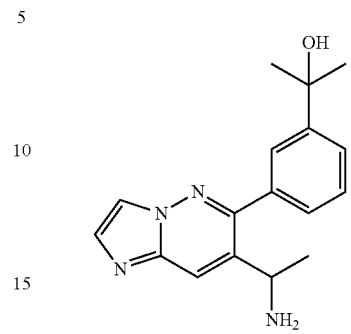

The mixture of tert-butyl (1-(6-(3-(2-hydroxypropan-2-yl)phenyl)imidazo[1,2-b]pyridazin-7-yl)ethyl)carbamate (120 mg, 0.30 mmol) in TFE (3 mL) was stirred at 140° C. for 1 hour in the microwave reactor. The mixture was concentrated in vacuo to give 95 mg of crude product which was used for the next step without purification. MS (m/z)=297 [M+H]⁺.

(F) 4-amino-6-((1-(6-(3-(2-hydroxypropan-2-yl)phenyl)imidazo[1,2-b]pyridazin-7-yl)ethyl)amino)pyrimidine-5-carbonitrile This compound was prepared according to the procedure of Compound 4 (L). MS (m/z)=415 [M+H]⁺.

(G) 4-amino-6-((1-(3-chloro-6-(3-(2-hydroxypropan-2-yl)phenyl)imidazo[1,2-b]pyridazin-7-yl)ethyl)amino)pyrimidine-5-carbonitrile This compound was prepared according to the procedure of Compound 4 (M).

(H) (chiral)-4-amino-6-((1-(3-chloro-6-(3-(2-hydroxypropan-2-yl)phenyl)imidazo[1,2-b]pyridazin-7-yl)ethyl)amino)pyrimidine-5-carbonitrile The racemic compound G was resolved by chiral HPLC to provide the optically pure enantiomers compound 79 (HPLC conditions: column: CHIRALPAK Ia 20 mm I.D.× 25 cm L; mobile phase: EtOH/DEA=100/0.10; flow rate=8.0 mL/min; detector: UV 254 nm). The eluent (Rt=3.958 min) was 97.51% ee. MS (m/z): 449 [M+H]⁺.

$^1$H NMR (400 MHz, dmso-6d) δ 8.26 (s, 1H), 7.87 (d, J=5.3 Hz, 2H), 7.78-7.76 (m, 2H), 7.60-7.58 (m, 1H), 7.43-7.72 (m, 2H), 7.21 (s, 2H), 5.19-5.11 (m, 1H), 1.43 (s, 3H), 1.43 (s, 3H), 1.34 (d, J=6.8 Hz, 3H).

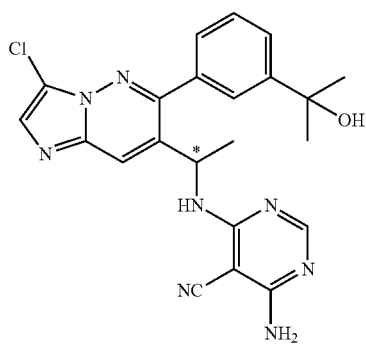

Compound 79 may be:

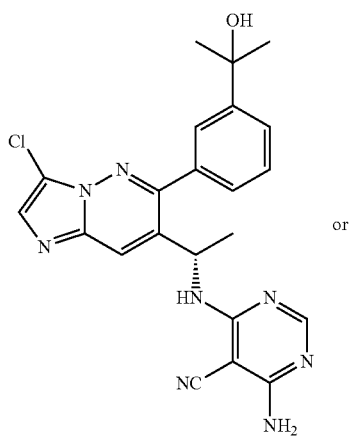

or

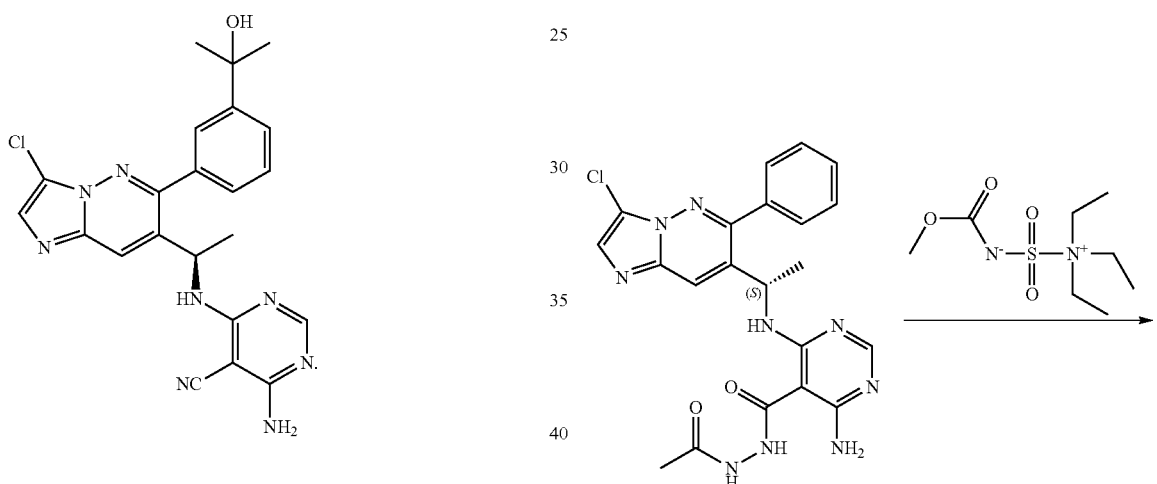

The following compound was prepared according to the procedure of Compound 79 (G) using the corresponding intermediates and reagents under appropriate conditions that will be recognized by the POSITA.

Compound 81

(S)-$N^4$-(1-(3-chloro-6-phenylimidazo[1,2-b]pyridazin-7-yl)ethyl)-5-(5-methyl-1,3,4-oxadiazol-2-yl)pyrimidine-4,6-diamine

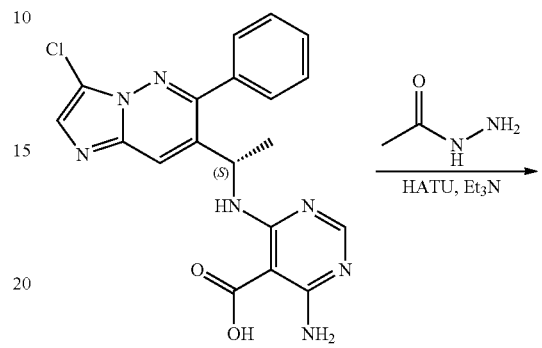

| Compound | Structure | MS (M + H)⁺ | NMR | Intermediate |
|---|---|---|---|---|
| 80 | 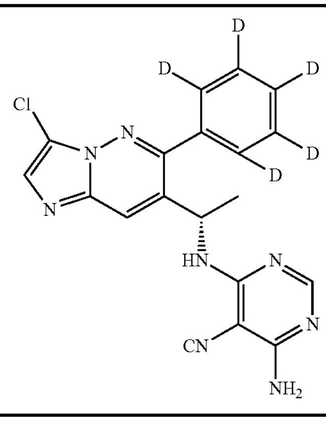 | 396 | ¹H NMR (400 MHz, CDCl₃) δ 8.05 (s, 1H), 7.93 (s, 1H), 7.70 (s, 1H), 5.46-5.44 (m, 1H), 5.41-5.34 (m, 1H), 5.33 (s, 2H), 1.36 (d, J = 6.8 Hz, 3H). | MS (M + H)⁺: 244 |

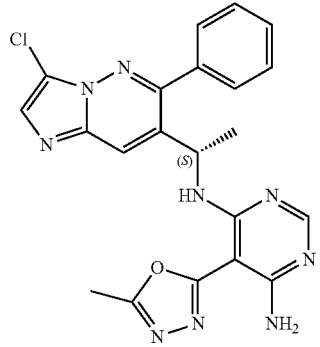 [SMILES: Cc1noc(-c2c(N)ncnc2N[C@@H](C)c2cc3ncc(Cl)n3nc2-c2ccccc2)n1]

(A) (S)-N'-acetyl-4-amino-6-((1-(3-chloro-6-phenylimidazo[1,2-b]pyridazin-7-yl)ethyl)amino)pyrimidine-5-carbohydrazide To a solution of (S)-4-amino-6-((1-(3-chloro-6-phenylimidazo[1,2-b]pyridazin-7-yl)ethyl)amino)pyrimidine-5-carboxylic acid (88 mg, 0.21 mmol), acetic hydrazide (19 mg, 0.25 mmol), HATU (95 mg, 0.25 mmol) in DMF (2 ml) was dropwise added Et$_3$N (64 mg, 0.63 mmol). The mixture was stirred at room temperature overnight. TLC and LC-MS showed the starting material was consumed. Then the mixture was partitioned between water (2 mL) and EA (5 mL). The organic layer was separated and the water layer was extracted with EA (5 mL×3). The combined organic layers was dried over anhydrous Na$_2$SO$_4$, concentrated to give 70 mg of crude product which was used for next step without any purification. MS (m/z)=466 [M+H]$^+$.

(B) (S)-N$^4$-(1-(3-chloro-6-phenylimidazo[1,2-b]pyridazin-7-yl)ethyl)-5-(5-methyl-1,3,4-oxadiazol-2-yl)pyrimidine-4,6-diamine To a stirred solution of (S)-N'-acetyl-4-amino-6-((1-(3-chloro-6-phenylimidazo[1,2-b]pyridazin-7-yl)ethyl)amino)pyrimidine-5-carbohydrazide (70 mg, 0.15 mmol) in dry THF (3 mL) was added methyl N-(triethylammoniumsulfonyl)carbamate (89 mg, 0.38 mmol). The mixture was heated and stirred for 3 hours at reflux. Then the mixture was cooled and concentrated. The residue was purified by flash column chromatograph (MeOH:H$_2$O=6:4) to give 10 mg of title compound. MS (m/z)=448 [M+H]$^+$.
$^1$H NMR (400 MHz, DMSO) δ 8.25 (d, J=6.4 Hz, 1H), 8.14 (s, 1H), 7.90 (s, 1H), 7.87 (s, 1H), 7.71-7.66 (m, 2H), 7.54-7.50 (m, 3H), 7.22 (s, 2H), 5.24-5.17 (m, 1H), 2.57 (s, 3H), 1.37 (d, J=6.9 Hz, 3H).

Compound 82

(S)-N$^4$-(1-(3-chloro-6-phenylimidazo[1,2-b]pyridazin-7-yl)ethyl)-5-(3-methyl-1,2,4-oxadiazol-5-yl)pyrimidine-4,6-diamine

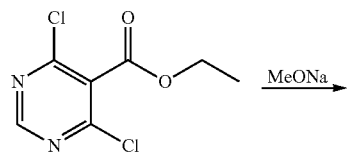

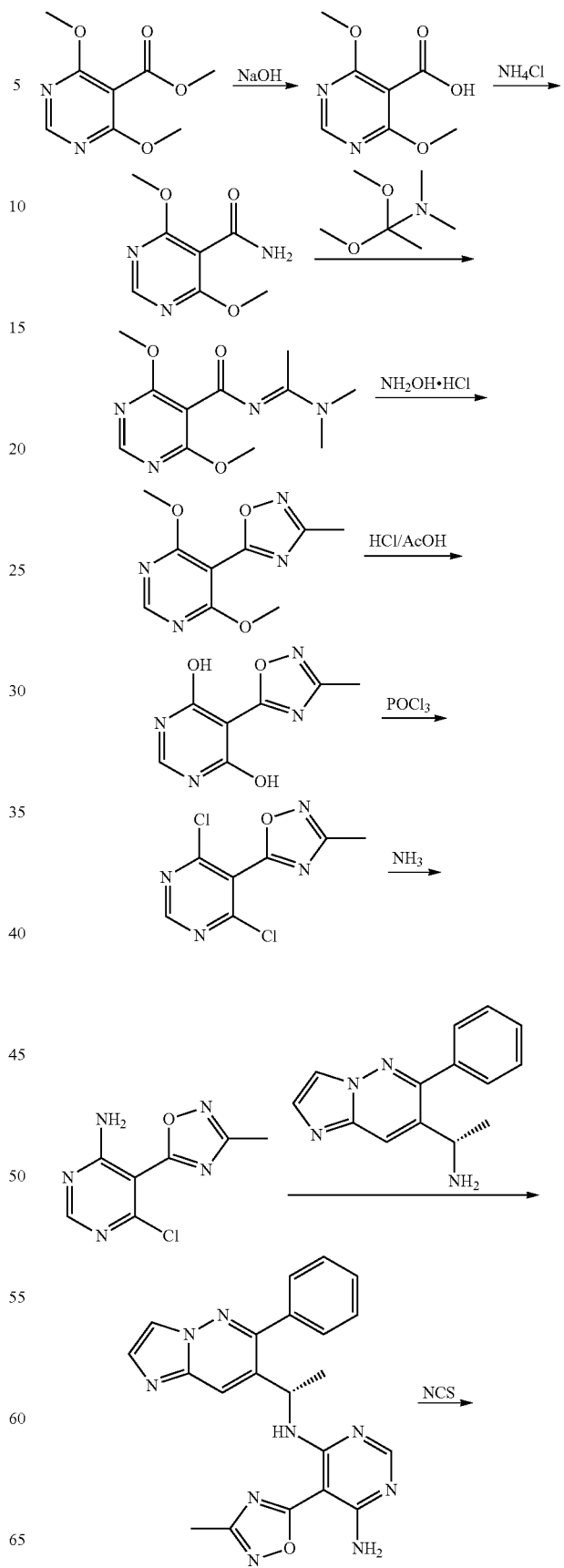

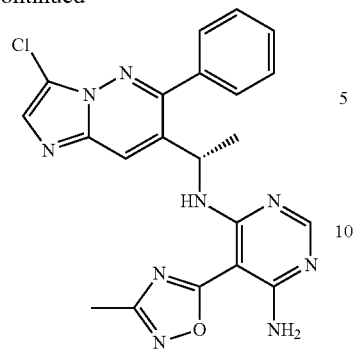

(A) methyl 4,6-dimethoxypyrimidine-5-carboxylate

To a solution of ethyl 4,6-dichloropyrimidine-5-carboxylate (5 g, 22.73 mmol) in MeOH (50 mL) was added sodium methoxide (4.3 g, 79.55 mmol) in batches. The reaction mixture was heated and stirred overnight at reflux. Than the mixture was added water (50 mL) and extracted with EA (50 mL×2). The combined organic layers was dried over anhydrous $Na_2SO_4$, concentrated to give 3.9 g of crude product. Yield: 88%. MS (m/z)=199 $[M+H]^+$.

(B) 4,6-dimethoxypyrimidine-5-carboxylic acid

To a solution of methyl 4,6-dimethoxypyrimidine-5-carboxylate (3.9 g, 19.69 mmol) in MeOH (40 mL) was added solution of NaOH (1.6 g, 39.38 mmol) in water (5 mL). Then the reaction mixture was heated to reflux and stirred for 2 hours. After cooling to room temperature, to the mixture was added hydrochloric acid (4 M, 10 mL) until pH=4-5. The precipitate was filtered to give 3.5 g of title compound. Yield: 95%. MS (m/z)=185 $[M+H]^+$.

(C) 4,6-dimethoxypyrimidine-5-carboxamide

To a solution of 4,6-dimethoxypyrimidine-5-carboxylic acid (2.5 g, 13.58 mmol), ammonia chloride (864 mg, 16.3 mmol), HATU (6.2 g, 16.3 mmol) in DMF (30 mL) was added dropwise $Et_3N$ (4.1 g, 40.74 mmol). The reaction mixture was stirred at room temperature overnight. TLC and LC-MS showed the starting material was consumed. Then the mixture was quenched with water (30 mL) and extracted with DCM (50 mL×3). The combined organic layers was dried over anhydrous $Na_2SO_4$, concentrated and the residue was purified by flash column chromatograph (DCM:MeOH=8:2) to give 1.3 g of title compound. Yield: 51%. MS (m/z)=184 $[M+H]^+$.

(D) (E)-N-(1-(dimethylamino)ethylidene)-4,6-dimethoxypyrimidine-5-carboxamide The solution of 4,6-dimethoxypyrimidine-5-carboxamide (1.3 g, 7.1 mmol) and N,N-Dimethylacetamide dimethyl acetal (4.7 g, 35.5 mmol) in dry toluene (20 mL) was heated to reflux and stirred overnight. Then the mixture was concentrated and the residue was purified by flash column chromatograph (EA:MeOH=7:3) to give 715 mg of title compound. Yield: 40%. MS (m/z)=253 $[M+H]^+$.

(E) 5-(4,6-dimethoxypyrimidin-5-yl)-3-methyl-1,2,4-oxadiazole (E)-N-(1-(dimethylamino)ethylidene)-4,6-dimethoxypyrimidine-5-carboxamide (715 mg, 2.83 mmol) was added to the solution of hydroxylamine hydrochloride (254 mg, 3.68 mmol) in the aqueous solution of NaOH (2 M, 2.4 mL, 4.81 mmol). Then dioxane (8 mL) and AcOH (5.6 mL, 99.05 mmol) were added. The mixture was heated to reflux and stirred overnight. Then the mixture was cooled, concentrated and the residue was purified by flash column chromatograph (MeOH:$H_2O$=6:4) to give 131 mg of title compound. Yield: 21%. MS (m/z)=223 $[M+H]^+$.

(F) 5-(3-methyl-1,2,4-oxadiazol-5-yl)pyrimidine-4,6-diol

To a stirred solution of 5-(4,6-dimethoxypyrimidin-5-yl)-3-methyl-1,2,4-oxadiazole (131 mg, 0.59 mmol) in AcOH (0.2 mL) was slowly added concentrated hydrochloric acid (0.2 mL) dropwise. Then the mixture was heated to 50° C. and stirred for 3 hours. Then the mixture was cooled and concentrated, the residue was purified by flash column chromatograph (MeOH:$H_2O$=15:85) to give 71 mg of title compound. Yield: 62%. MS (m/z)=195 $[M+H]^+$.

(G) 5-(4,6-dichloropyrimidin-5-yl)-3-methyl-1,2,4-oxadiazole

The solution of 5-(3-methyl-1,2,4-oxadiazol-5-yl)pyrimidine-4,6-diol (71 mg, 0.36 mmol) in $POCl_3$ (1 mL) was heated to 100° C. and stirred for 1 hour. The mixture was cooled and added to ice water very slowly at drop wise. The aqueous layer was extracted with DCM (5 mL×3). The combined organic layers was dried over anhydrous $Na_2SO_4$, concentrated to give 54 mg of title compound which was used for next step without any purification. Yield: 64% MS (m/z)=231 $[M+H]^+$.

(H) 6-chloro-5-(3-methyl-1,2,4-oxadiazol-5-yl)pyrimidin-4-amine

The solution of 5-(4,6-dichloropyrimidin-5-yl)-3-methyl-1,2,4-oxadiazole (54 mg, 0.23 mmol) in THF (1 mL) was bubbled through $NH_3$ for 5 minutes and stirred for 2 hours at room temperature. Then the mixture was concentrated to give 36 mg of title compound which was used for next step without any purification. Yield: 75%. MS (m/z)=212 $[M+H]^+$.

(I) (S)-5-(3-methyl-1,2,4-oxadiazol-5-yl)-$N^4$-(1-(6-phenylimidazo[1,2-b]pyridazin-7-yl)ethyl)pyrimidine-4,6-diamine This compound was prepared according to the procedure of Compound 4 (L). MS (m/z)=414 $[M+H]^+$

(J) (S)-$N^4$-(1-(3-chloro-6-phenylimidazo[1,2-b]pyridazin-7-yl)ethyl)-5-(3-methyl-1,2,4-oxadiazol-5-yl)pyrimidine-4,6-diamine This compound was prepared according to the procedure of Compound 4 (M). MS (m/z)=448 $[M+H]^+$
$^1$H NMR (400 MHz, $CO_3OD$) δ 8.00 (s, 1H), 7.94 (s, 1H), 7.72-7.69 (m, 3H), 7.54-7.49 (m, 3H), 5.53-5.43 (m, 1H), 2.45 (s, 3H), 1.45 (d, J=6.9 Hz, 3H).

Example 2: Fluorescent Determination of PI3K Enzyme Activity

PI3K kinases including p110α/p85α and p110γ were purchased from Invitrogen, p110δ/p85α and p110β/p85α were from Millipore.

Primary screening data and IC$_{50}$ values were measured using Transcreener™ KINASE Assay (Bellbrook, Catalog #3003-10K). The Assay can be carried out according to the procedures suggested by the manufacturer. It is a universal, homogenous, high throughput screening (HTS) technology using a far-red, competitive fluorescence polarization immunoassay based on the defection of ADP to monitor the activity of enzymes that catalyze group transfer reactions. Briefly, the Transcreener KINASE Assay was designed as a simple two-part, endpoint assay as follows:

1) Preparation of 25 uL kinase reaction: the 25 uL kinase reaction was performed by preparing a reaction mixture containing 10 uL kinase buffer (50 mM HEPES, 100 mM NaCl, 1 mM EGTA, 0.03% CHAPS, 3 mM MgCl$_2$, and freshly supplemented 1 mM DTT), and 10 uL 30 uM PIP2 and 10 uM ATP, 5 uL test compound solution (the compound was dissolved in DMSO, the final concentrations of the compound in the reaction mixture were at 1 uM, 0.3 uM, 0.1 uM, 0.037 uM, 0.012 uM, 0.0041 uM, 0.0014 uM and 0.0005 uM, and final concentration of DMSO in the reaction mixture was 2%) or 5 uL control (2% DMSO). The reaction mixture was added into desired wells of a 96-well plate. The plate was sealed and incubated for 80 min at room temperature.

2) Next, 25 uL ADP detection mix was added into each well. The plate was sealed again and incubated for 60 min at room temperature. Then fluorescence polarization was measured by Tecan Infinite F500 Reader.

Data was analyzed and IC$_{50}$ values were generated using the add-in software for Microsoft Excel, Xlfit™ (version 5.3).

Inhibition rates were calculated as follow: IH %=(ADP amount under 2% DMSO well−ADP amount under test compound well)/ADP amount under 2% DMSO well× 100%.

Below are the IC$_{50}$ (μM) values or inhibition rates (IH %) at 1 μM of some compounds:

| Compound | PI3K-δ IC$_{50}$ (μM) | IH% | PI3K-γ IC$_{50}$ (μM) | IH% | PI3K-β IC$_{50}$ (μM) | IH% | PI3K-α IC$_{50}$ (μM) | IH% |
|---|---|---|---|---|---|---|---|---|
| 1 | 0.028 | | | 16.1% | | 28.1% | — | |
| 2 | 0.001 | | 0.168 | | 0.323 | | >1 | |
| 3 | 0.048 | | | 6.9% | 4.810 | | — | |
| 4 | 0.0003 | | 0.038 | | 0.087 | | >1 | |
| 5 | | 47.3% | | | | −10.7% | — | |
| 6 | 0.001 | | | 4.1% | 0.303 | | >1 | |
| 7 | | 12.5% | | 61.1% | | −2.7% | — | |
| 8 | 0.010 | | | −2.3% | | 37.7% | >1 | |
| 9 | 0.002 | | 0.046 | −1.4% | 0.158 | | — | |
| 11 | 0.003 | | 0.094 | | | 55.7% | — | |
| 12 | 0.002 | | 0.55 | | 0.080 | | | |
| 13 | 0.003 | | 0.484 | | 1.918 | | >1 | |
| 14 | | 51.0% | | 22.5% | | 3.2% | — | |
| 15 | 0.001 | | 0.393 | | | 59% | >1 | |
| 16 | 0.003 | | 0.326 | | | 27.5% | >1 | |
| 17 | 0.026 | | | 61.2% | | 15.8% | >1 | |
| 18 | 0.004 | | 0.617 | | | 42% | >1 | |
| 19 | 0.002 | | 1.965 | | 1.07 | | >1 | |
| 20 | 0.073 | | | 43.1% | | 17.4% | >1 | |
| 21 | 0.006 | | 0.424 | | 0.5 | | | 21.7% |
| 22 | 0.002 | | 0.322 | | | 76.7% | | 13.6% |
| 23 | 0.006 | | 0.343 | | | 28.7% | | 3.2% |
| 24 | 0.002 | | | 44.5% | | 46.6% | | |
| 25 | 0.004 | | 2.593 | | | 22.8% | | |
| 26 | 0.839 | | | 8% | | −7.5% | | |
| 27 | 0.025 | | | 24.9% | | 9.5% | | |
| 28 | | 39.8% | | 18.8% | | 11.1% | | |
| 29 | 0.003 | | | 35% | 0.174 | | | |
| 30 | 0.003 | | 0.410 | | 1.039 | | | |
| 31 | 0.004 | | 0.146 | | 0.371 | | | |
| 32 | 0.015 | | 0.243 | | | 23.8% | | |
| 33 | 0.288 | | | −6.9% | | 2.2% | | |
| 34 | | 8.3% | | −19.3% | | 3.7% | | |
| 35 | 0.004 | | | 64.6% | | 67.6% | | |
| 36 | 0.003 | | 0.243 | | 1.310 | | | |
| 37 | 0.288 | | | 27.5% | | −0.4% | | |
| 38 | 0.066 | | | 54.3% | | −2.2% | | |
| 39 | 0.073 | | | 28.1% | | −4.4% | | |
| 40 | 0.002 | | >0.333 | | 0.277 | | | |
| 41 | 0.003 | | 0.499 | | 1.331 | | | |
| 42 | 0.339 | | | 18.2% | | 7.4% | | |
| 43 | 0.132 | | | 27.2% | | 23.6% | | |
| 44 | 0.283 | | | 36.0% | | 18.8% | | |
| 45 | 0.003 | | 0.195 | | 0.450 | | | |
| 46 | 0.004 | | 0.050 | | 1.318 | | | |
| 47 | 0.018 | | | 55.2% | | 32.2% | | |
| 48 | 0.009 | | 1.331 | | 4.083 | | | |
| 49 | 0.001 | | 0.146 | | 0.001 | | | |
| 50 | | 68.9% | | 5.5% | | −14.1% | | |
| 51 | 0.957 | | | 36.7% | | −15.5% | | |
| 52 | 0.080 | | | −26.1% | | −6.3% | | |

-continued

| Compound | PI3K-δ IC$_{50}$ (μM) | IH% | PI3K-γ IC$_{50}$ (μM) | IH% | PI3K-β IC$_{50}$ (μM) | IH% | PI3K-α IC$_{50}$ (μM) | IH% |
|---|---|---|---|---|---|---|---|---|
| 53 | 0.011 | | | 34.3% | | 30.5% | | |
| 54 | 0.002 | | 0.226 | | 0.009 | | | |
| 55 | | 60.3% | | −4.7% | | 8.5% | | |
| 56 | | 21.0% | | 1.0% | | 9.0% | | |
| 57 | 0.062 | | | 30.3% | | 6.3% | | |
| 58 | 0.138 | | | 20.2% | | 20.5% | | |
| 59 | 0.005 | | 2.393 | | 1.161 | | | |
| 60 | 0.001 | | 0.048 | | 0.034 | | | |
| 61 | 0.007 | | | 26.5% | | 24.4% | | |
| 62 | 0.002 | | 0.247 | | 1.232 | | | |
| 63 | 0.006 | | 0.105 | | | 48.1% | | |
| 64 | 0.048 | | >0.333 | | | 44.1% | | |
| 65 | 0.002 | | 0.611 | | 1.257 | | | |
| 66 | 0.009 | | 1.119 | | 4.298 | | | |
| 67 | 0.005 | | 1.145 | | 3.584 | | | |
| 68 | 0.002 | | 0.345 | | 0.963 | | | |
| 69 | 0.001 | | 0.023 | | 0.133 | | | |
| 70 | 0.022 | | 1.979 | | | 37.4% | | |
| 71 | 0.129 | | | 32.6% | | 35.2% | | |
| 72 | 0.004 | | 0.513 | | 0.089 | | | |
| 73 | 0.082 | | | 62.8% | | 60.8% | | |
| 74 | 0.009 | | | 40.8% | | 49.4% | | |
| 75 | | 1.0% | | 31.7% | | −7.1% | | |
| 76 | | 48.9% | | −14.3% | | 54.9% | | |
| 77 | 0.002 | | 0.436 | | 0.238 | | | |
| 78 | 0.001 | | 0.712 | | | 50.1% | | |
| 79 | 0.002 | | | 56.2% | | 43.8% | | |
| 80 | 0.0005 | | 0.059 | | 0.272 | | | |
| 81 | 0.002 | | 0.098 | | 0.630 | | | |
| 82 | 0.013 | | 0.203 | | | 55.2% | | |

Example 3: Inhibition of AKT Phosphorylation in Ramos Cell Line

6×10$^4$/mL Ramos cells (ATCC, CRL-1596; cells were cultured in RPMI1640 media with 10% FBS) were seeded into a 96-well plate (Bookman Dickinson, No. 356692) at 80 uL/well, 4,800 cells/well. After incubations for 3 hr at 37° C. under 5% $CO_2$, Ramos cells were treated with 10 uL/well various concentrations of test compound (final concentrations of the test compound: 1 uM, 0.3 uM, 0.1 uM, 0.037 uM, 0.012 uM, 0.0041 uM, 0.0014 uM and 0.0005 uM) or 0.3% DMSO for 30 min, and then were stimulated with 10 uL/well 1 ug/ml Anti-IgM (Jackson Immunoresearch, 709-006-073) for 15-20 min.

1) Cells were fixed with 100 μL of 4% pre-warmed Paraformaldehyde (2% final concentration), and incubated for 45 min at room temperature.
2) The paraformaldehyde solution was removed. 100 μL of ice-cold methanol was added into each well and the plate was left at 4° C. for 30 min.
3) The cells were washed for three times with 160 μPBS.
4) 40 μL 1:350 dilution of Rabbit anti-p-AKT(Ser$^{473}$) antibody (Cell Signaling Technology, 4060 L) in antibody dilution buffer (1% BSA, in PBS) were added into each well. The plate was incubated overnight at 4° C.
5) The cells were washed for 3 times with 160 uL PBS.
6) 45 μL of Goat anti-rabbit IgG Alexa488 antibody (Invitrogen, A11034) at a 1:1,000 dilution in antibody dilution buffer (1% BSA, in PBS) were added into each well. The plate was covered with foil to keep out of light and was incubated for 90 min at room temperature.
7) The cells were washed for 3 times with 160 uL PBS.
8) 50 μL of 1.5 μM Propidium Iodide (Sigma: P4170) solution was added into each well to determine cell number (1.5 mM Propidium Iodide stock was diluted with 1:1,000 in PBS, and the final concentration was 1.5 μM).
9) The plate was incubated at room temperature for 30 min and then was sealed with a cover-seal.
10) The plate was loaded into the Acumen Explorer and scan with the appropriate instrument settings.

Data was analyzed and IC$_{50}$ values were generated using the add-in software for Microsoft Excel, Xlfit™ (version 5.3).

Below are the IC$_{50}$ (μM) values of some compounds:

| Compound | IC$_{50}$ (μM) |
|---|---|
| 2 | 0.001 |
| 4 | 0.002 |
| 6 | 0.0003 |
| 13 | 0.004 |
| 15 | 0.0005 |
| 22 | 0.004 |
| 23 | 0.012 |
| 24 | 0.007 |
| 25 | 0.005 |
| 30 | 0.001 |
| 31 | 0.002 |
| 32 | 0.020 |
| 35 | 0.013 |
| 36 | 0.001 |
| 40 | 0.003 |
| 41 | 0.012 |
| 45 | 0.003 |
| 46 | 0.006 |
| 48 | 0.008 |
| 53 | 0.016 |
| 59 | 0.006 |

-continued

| Compound | IC$_{50}$ (μM) |
|---|---|
| 61 | 0.041 |
| 62 | 0.001 |
| 65 | 0.002 |
| 66 | 0.002 |
| 67 | 0.003 |
| 68 | 0.001 |
| 74 | 0.023 |
| 77 | 0.003 |
| 78 | 0.007 |
| 79 | 0.002 |

Example 4: Inhibition of PI3Kδ Signaling in Basophils from Human Whole Blood

1. Reagents and Materials

| Reagent | Brand | Cat |
|---|---|---|
| anti-IgE-PE, anti-CD63-FITC | ORPEGEN pharma | BAT kit component |
| wash buffer | ORPEGEN pharma | BAT kit component |
| 10 × lysis buffer | BD | 555899 |
| Recombinant human IL-3 | Peprotech | AF-200-03 |
| Goat anti-human IgE | Bethyl | A80-108A |
| 96-well v-bottom plate | NUNC | 249952 |

2. Methods

1) Heparinized human whole blood was mixed and pipetted into the 96 well v-bottom plate, 100 μL per well.
2) 10 μL of stimulation buffer (1 mg/mL stock, final concentration of Recombinant human IL-3; 20 ng/mL) was added to the whole blood samples of each well and vortex gently. The samples were incubated for 20 min at 37° C.
3) 10 uL/well of test compound dilution (final concentrations of the test compound in well: 1 uM, 0.3 uM, 0.1 uM, 0.037 uM, 0.012 uM, 0.0041 uM, 0.0014 uM and 0.0005 uM) or vehicle (0.2% DMSO) was added into each well of the plate and the plate was incubated for 1.5 h at 37° C.
4) 100 μL of the Goat anti-human IgE (1 mg/mL stock, final concentration of IgE: 0.31 ug/mL) working solution was added into each well of the plate. Vortex all the wells once more and incubate for 20 min at 37° C.
5) Labeling with staining antibody: Degranulation was stopped by incubating the samples on ice for 5 min. 6 μL of staining antibody mixture (anti-CD63-FITC and anti-IgE-PE) was added into each well. Vortex and incubate the wells for 20 min in an ice bath, covered to prevent exposure to light.
6) The whole blood samples were lysed with 300 uL RBC lysis (pre-warmed to room temperature, 20 to 25° C.). Vortex and incubate the samples for 15 min at room temperature. Spin down cells (5 min, 250×g, 4° C.). The supernatant was aspirated leaving approximately 100 μL in each well.
7) The blood samples were lysed once more as step 6).
8) Washing: The samples are washed once with 0.5 mL of washing solution. The plate was centrifuged (5 min, 250×g, 4° C.). The supernatant was aspirated leaving approximately 100 μL in each well. The sample in each well was washed and centrifuged once more as above.
9) 200 μL of fixing solution (1% papraledehyde in 1% BSA/PBS) was added into each well. The plate was incubated in a covered ice bath until analysis.
10) Flow cytometric analysis: Cells were analyzed by flow cytometry using the blue-green excitation light (488 nm argon-ion laser, FACSCalibur, CELLQuest software).

3. Data Analysis

Data was analyzed and IC$_{50}$ values were generated using the add-in software for Microsoft Excel, Xlfit™ (version 5.3).

Below are the IC$_{50}$ (μM) values of some compounds:

| Compound | IC$_{50}$ (μM) |
|---|---|
| 4 | 0.001 |
| 6 | 0.006 |
| 8 | 0.009 |
| 13 | 0.010 |
| 15 | 0.002 |
| 16 | 0.011 |
| 17 | 0.618 |
| 18 | 0.088 |
| 19 | 0.016 |
| 20 | 0.397 |
| 22 | 0.002 |
| 23 | 0.006 |
| 24 | 0.011 |
| 25 | 0.037 |
| 27 | 0.565 |
| 30 | 0.006 |
| 41 | 0.018 |
| 48 | 0.041 |
| 59 | 0.1 |
| 61 | 0.109 |
| 62 | 0.015 |
| 65 | 0.014 |
| 66 | 0.262 |
| 67 | 0.010 |
| 68 | 0.002 |
| 78 | 0.010 |

Example 5: In Vitro Cell Proliferation Assay in SU-DHL-6 Cell Line

Growth inhibition assays were carried out using 10% FBS supplemented media. Cells were seeded at a concentration of 15000 cells/well in a 96-well plate. Test compound dilution at different concentrations (final concentrations of the test compound: 1 uM, 0.3 uM, 0.1 uM, 0.037 uM, 0.012 uM, 0.0041 uM, 0.0014 uM and 0.0005 uM) were added after 24 hours. Growth was assessed using Cell Counting Kit-8 (CCK-8) (Dojindo, Cat # CK04) after the test compound were incubated for 72 h. Absorbance was read at the wave length 450 nm on Multiskan MK3 machine (Thermo).

Data was analyzed and IC$_{50}$ values were generated using the add-in software for Microsoft Excel, Xlfit™ (version 5.3).

Below are the IC$_{50}$ (μM) values of some compounds:

| Compound | IC$_{50}$ (μM) |
|---|---|
| 4 | 0.001 |
| 6 | 0.003 |

-continued

| Compound | IC$_{50}$ (μM) |
|---|---|
| 8 | 0.031 |
| 13 | 0.011 |
| 15 | 0.002 |
| 16 | 0.011 |
| 17 | 0.172 |
| 18 | 0.026 |
| 19 | 0.023 |
| 20 | 0.262 |
| 22 | 0.019 |
| 23 | 0.078 |
| 24 | 0.011 |
| 25 | 0.032 |
| 29 | 0.011 |

Example 6: Effect of Compound 4 in Anti-IgD Antibody Induced B Cells Activation in Rat Whole Blood Activation of B cells (B220+) in rat whole blood with anti-IgD antibody leading to activation via Ig receptors is known to involve PI$_3$K pathways and sensitive to modulation by PI$_3$Kδ inhibitors. A pharmacodynamics assay was developed to assess activity of PI$_3$Kδ inhibitors ex vivo following oral administration of inhibitors to rats.

Wistar rats (female, 6-8 weeks old) were used in the experiments. The dose dependency, time course study and PKPD relationship of compound 4 were conducted in normal Wistar rats. Compound 4 (0.01, 0.03, 0.1, 0.3, 1, 3 mg/kg) dissolved or suspended in vehicle (0.5% CMC-Na, pH 2.1) were administered to rats (3 rats per dose) orally once. The control group (6 rats) was treated with the vehicle alone. At designated time points (1 hour, 8 hours, 16 hours and 24 hours after administration), blood samples were collected from rats via retro-orbital bleeding under isofluorane anesthesia into heparinized tubes. The heparin anticoagulated blood was mixed with anti-rat-IgD, then was incubated at 37° C. under 5% CO$_2$ overnight. Fluorescence signal for CD86 on B220 (B cells) positive cells was detected using a flow cytometer (BD FACSCalibur, BD Biosciences) and data were analyzed by CellQuest software. Plasma was collected to measure compound 4 levels.

As shown in FIG. 1, compound 4 inhibited anti-IgD induced B cell activation in rat whole blood, ex vivo, in a dose- and time-dependent manner, in the dose range of 0.01 to 3 mg/kg (p<0.01). The ED$_{50}$ values at 2 hr post-dose were <0.01 mg/kg with corresponding EC$_{50}$ value of 1.487 ng/mL. Plasma levels of compound 4 were dose-proportional in the dose range of 0.01 mg/kg to 3 mg/kg. Follow single oral administration of 0.1 mg/kg dose, complete inhibition of B cell activation (>90% inhibition) was observed for up to 24 hr.

Example 7: Effect of Compound 4 in Rat Collagen II Induced Arthritis (CIA) Model Rat collagen induced arthritis is an experimental model of polyarthritis that has been widely used for nonclinical testing of numerous anti-arthritic agents that are either under nonclinical or clinical investigation or are currently used as therapeutics in this disease.

The protective effect of compound 4 was evaluated in the rat collagen-induced arthritis (CIA) model. Wistar rats were immunized intradermally with 200 μg bovine collagen II emulsified in Freund's incomplete adjuvant (IFA, Sigma, US) on day 0 and day 7. The hind paw volumes were measured before and after the immunization. To assess the anti-inflammatory action of compound 4, female Wistar rats with established type II collagen-induced arthritis were treated orally (PO) with compound 4 (0.03, 0.1 and 1 mg/kg) or vehicle (0.5% CMC-Na, pH 2.1) once daily (CD) for 7 days (days 10-16) after induction with type II collagen. The naive group was not administered. YiSaiPu (10 mg/kg), a human tumor necrosis factor receptor p75 Fc fusion protein, was administered with intraperitoneal injection on days 10, 12 and 14 as a positive control. The study was terminated on day 18. The results of the study are shown in FIG. 2.

Figure 2:
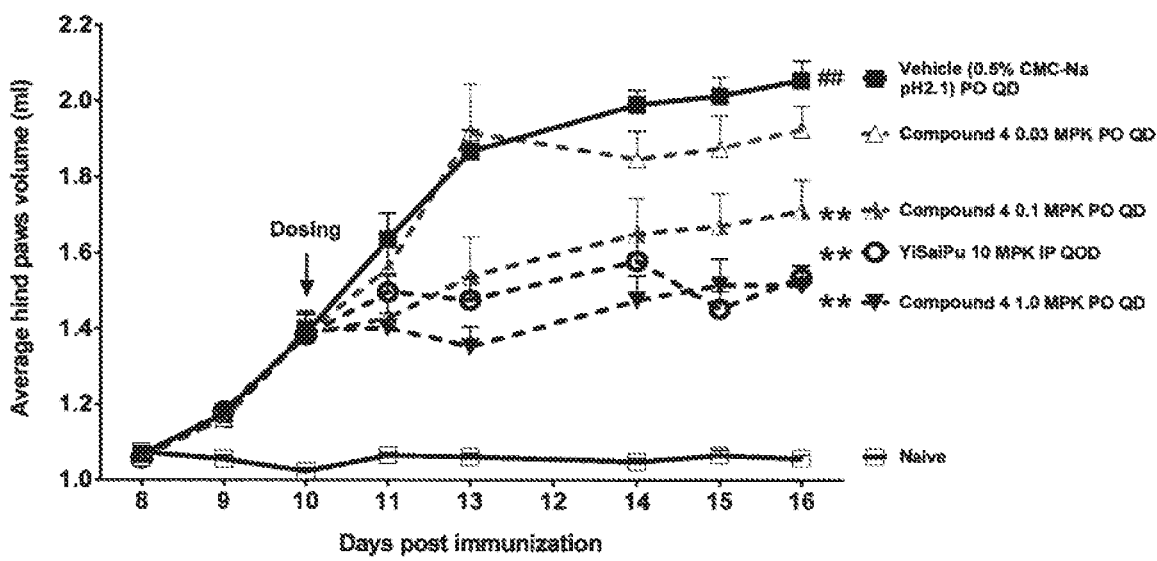
FIG. 2 shows effects of compound 4 prepared in example 1 on paw volumes in CIA Wistar rats. The hind paw volumes were measured daily by Plethysmometer. Data of paw volumes are presented as mean±SEM (n=6 for naive group, n=8 for the rest of groups), the rest of groups are vehicle control group, compound 4 groups of different dose (QD) and positive control group (QOD). The area under the curve (AUC) of the mean paw swelling is analyzed by one-way ANOVA using Sigmastat statistical software, followed by Fisher's Least Significant Difference (LSD) test, and p values are calculated. ## shows p<0.01 vs naive group; ** shows p<0.01 vs vehicle control group.

As shown in FIG. 2, Paw volume for vehicle treated rats peaked on day 16. At the end of the treatment period, the mean volume was significantly decreased for all active treatment groups compared to vehicle-treated diseased animals (p<0.01) except at the lowest dose of compound 4 (0.03 mg/kg)

The area under the curve (AUC) from the mean paw swelling over time profile was used as a parameter to evaluate the effect of compound 4 on paw volume over several days of dosing. For each dose group, the percent reduction in the AUC relative to vehicle-treated diseased animals was determined across the 0.03 to 1 mg/kg dose range evaluated. Reductions in the ankle diameter AUC of compound 4 ranged from 15.5% to 99.5% relative to vehicle controls. In the same study, treatment with YiSaiPu (10 mg/kg, QOD) reduced paw swelling AUC by 81.6% relative to animals treated with vehicle.

In conclusion, daily oral treatment with compound 4 displayed dose-dependent beneficial effects on the parameters associated with established type II collagen-induced arthritis in rats.

What is claimed is:

1. A method of treating a disease in a subject in need thereof, comprising administering to the subject an effective amount of a compound of formula (I):

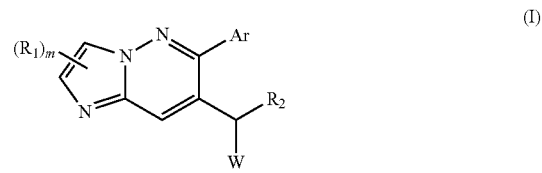

and/or a pharmaceutically acceptable salt thereof, and/or solvates, racemic mixture, enantiomers, diastereomers, and tautomers thereof, wherein Ar is aryl or heteroaryl, each of which is optionally substituted with one or more groups chosen from deuterium, halo, —CN, —OH, —SH, C$_{1-6}$ alkyl, C$_{2-6}$ alkenyl, C$_{2-6}$ alkynyl, C$_{1-6}$ haloalkyl, —O(C$_{1-6}$ alkyl), —(C$_{1-6}$ alkyl)OH, —NH$_2$, —NH(C$_{1-6}$ alkyl), —N(C$_{1-6}$ alkyl)(C$_{1-6}$ alkyl), and —S(O)$_2$(C$_{1-6}$ alkyl);

W is chosen from heteroaryl and N(R$_3$)heteroaryl, wherein said heteroaryl is optionally substituted with one or more groups chosen from halo, —CN, —OH, —SH, C$_{1-6}$ alkyl, C$_{2-6}$ alkenyl, C$_{2-6}$ alkynyl, C$_{1-6}$ haloalkyl, —O(C$_{1-6}$ alkyl), —(C$_{1-6}$ alkyl)OH, —NH$_2$, —NH(C$_{1-6}$ alkyl), —N(C$_{1-6}$ alkyl)(C$_{1-6}$ alkyl), —COOH, —C(O)NH$_2$, —C(O)NH(C$_{1-6}$ alkyl), —C(O)N(C$_{1-6}$ alkyl)(C$_{1-6}$ alkyl), —SO$_2$(C$_{1-6}$ alkyl), phenyl, and 5- or 6-membered heteroaryl; in which each of said phenyl or 5- or 6-membered heteroaryl as the substituent of W is optionally substituted with one or more groups chosen from halo, —CN, —OH, —SH, $C_{1-6}$ alkyl, $C_{1-6}$ haloalkyl, —O($C_{1-6}$ alkyl), —($C_{1-6}$ alkyl)OH, —$NH_2$, —NH($C_{1-6}$ alkyl), and —N($C_{1-6}$ alkyl)($C_{1-6}$ alkyl);

$R_1$ is independently chosen from H, halo, —CN, $C_{1-6}$ alkyl, $C_{1-6}$ haloalkyl, —($C_{1-6}$ alkyl)OH, —($C_{1-6}$ alkyl)O($C_{1-6}$ alkyl), and $C_{2-6}$ alkynyl;

$R_2$ is chosen from H, $C_{1-6}$ alkyl, and $C_{3-8}$ cycloalkyl, each of which except for H, is optionally substituted with one or more groups chosen from halo, —CN, $C_{1-6}$ alkyl, $C_{1-6}$ haloalkyl, and —OH;

$R_3$ is H or $C_{1-6}$ alkyl;

m is 1 or 2;

wherein said disease is rheumatoid arthritis or B-cell lymphoma.

2. The method of claim 1, wherein in formula (I), W is chosen from nitrogen-containing heteroaryl and N($R_3$) nitrogen-containing heteroaryl, wherein said nitrogen-containing heteroaryl is optionally substituted with one or more groups chosen from fluoro, chloro, bromo, —CN, —OH, —SH, $C_{1-6}$ alkyl, $C_{1-6}$ haloalkyl, —$NH_2$, —NH($C_{1-6}$ alkyl), —N($C_{1-6}$ alkyl)($C_{1-6}$ alkyl), —COOH, —C(O)$NH_2$, phenyl, and 5- or 6-membered heteroaryl; in which each of said phenyl and 5- or 6-membered heteroaryl as the substituent of W is optionally substituted with one or more groups chosen from halo, —OH, $C_{1-6}$ alkyl, and —O($C_{1-6}$ alkyl).

3. The method of claim 1, wherein in formula (I), W is chosen from

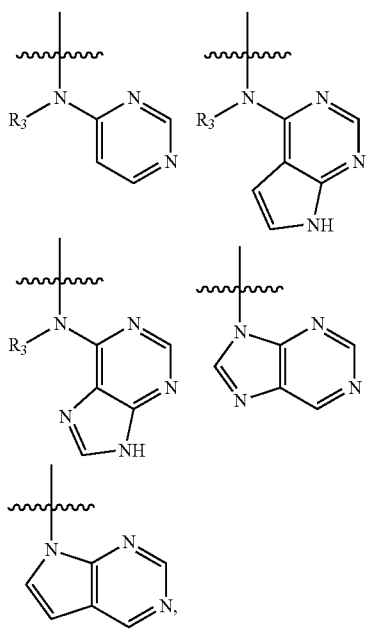

each of which is optionally substituted with one or more groups chosen from fluoro, chloro, bromo, —CN, —OH, —SH, $C_{1-6}$ alkyl, $C_{1-6}$ haloalkyl, —$NH_2$, —NH($C_{1-6}$ alkyl), —N($C_{1-6}$ alkyl)($C_{1-6}$ alkyl), —COOH, —C(O)$NH_2$, —C(O)NH($C_{1-6}$ alkyl), phenyl, and 5- or 6-membered heteroaryl; in which each of said phenyl and 5- or 6-membered heteroaryl as the substituent of W is optionally substituted with one or more groups chosen from halo, —CN, —OH, —SH, $C_{1-6}$ alkyl, $C_{1-6}$ haloalkyl, —O($C_1$-$C_6$ alkyl), —($C_{1-6}$ alkyl)OH, —$NH_2$, —NH($C_{1-6}$ alkyl), or —N($C_{1-6}$ alkyl)($C_{1-6}$ alkyl).

4. The method of claim 1, wherein in formula (I), W is

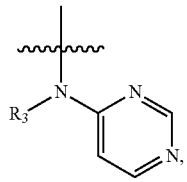

which is optionally substituted with one or more groups chosen from fluoro, chloro, bromo, —CN, —OH, —SH, $C_{1-6}$ alkyl, $C_{1-6}$ haloalkyl, —$NH_2$, —NH($C_{1-6}$ alkyl), —N($C_{1-6}$ alkyl)($C_{1-6}$ alkyl), —COOH, —C(O)$NH_2$, phenyl, and 5- or 6-membered heteroaryl; in which each of said phenyl and 5- or 6-membered heteroaryl as the substituent of W is optionally substituted with one or more groups chosen from halo, —OH, $C_{1-6}$ alkyl, and —O($C_{1-6}$ alkyl).

5. The method of claim 1, wherein in formula (I), W is

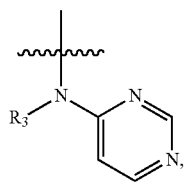

which is optionally substituted with one or more groups chosen from chloro, —CN, —$NH_2$, NH($C_{1-6}$ alkyl), —COOH, —C(O)$NH_2$, phenyl, pyridyl, oxadiazolyl, pyrazolyl and tetrazolyl; in which each of said phenyl, pyridyl, oxadiazolyl, pyrazolyl, and tetrazolyl is optionally substituted with one or more groups chosen from halo, —OH, $C_{1-6}$ alkyl, or —O($C_{1-6}$ alkyl).

6. The method of claim 1, wherein in formula (I), Ar is chosen from phenyl, naphthyl, pyridyl, pyrazolyl, quinolyl, thienyl, benzothiazolyl, indolyl, and 2,3-dihydro-1,4-benzodioxinyl, each of which is optionally substituted with one or more groups chosen from D, halo, —CN, $C_{1-6}$ alkyl, —($C_{1-6}$ alkyl)OH, $C_{1-6}$ haloalkyl, and —S(O)$_2$($C_{1-6}$ alkyl).

7. The method of claim 1, wherein in formula (I), Ar is phenyl or pyridyl, each of which is optionally substituted with one or more groups chosen from halo, —CN, and $C_{1-6}$ haloalkyl.

8. The method of claim 1, wherein in formula (I), $R_1$ is independently chosen from H, halo, —CN, and $C_{1-6}$ alkyl.

9. The method of claim 1, wherein in formula (I), $R_2$ is $C_{1-6}$ alkyl.

10. The method of claim 1, wherein formula (I) is formula (I-1),

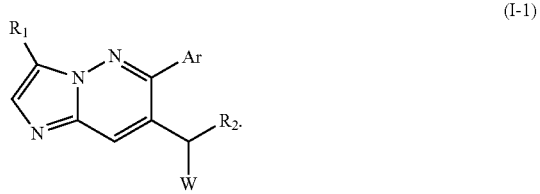

(I-1)

11. The method of claim 10, wherein in formula (I-1), W is chosen from

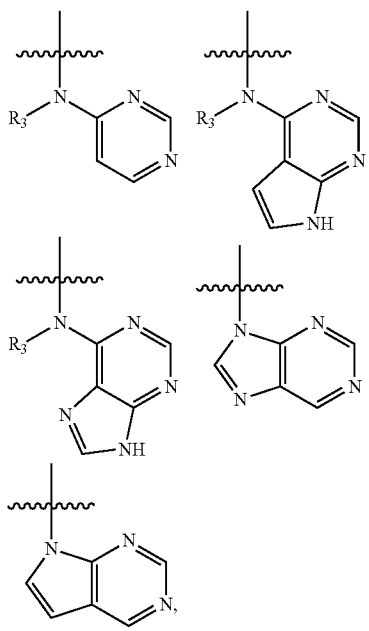

each of which is optionally substituted with one or more groups chosen from fluoro, chloro, bromo, —CN, —OH, —SH, $C_{1-6}$ alkyl, $C_{1-6}$ haloalkyl, —$NH_2$, —NH($C_{1-6}$ alkyl), —N($C_{1-6}$ alkyl)($C_{1-6}$ alkyl), phenyl, and 5- or 6-membered heteroaryl.

12. The method of claim 10, wherein in formula (I-1), W is

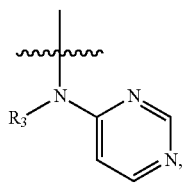

which is optionally substituted with one or more groups chosen from —CN, —$NH_2$, and tetrazolyl.

13. The method of claim 10, wherein in formula (I-1), Ar is chosen from phenyl, naphthyl, pyridyl, pyrazolyl, quinolyl, thienyl, and benzothiazolyl, each of which is optionally substituted with one or more groups chosen from halo, —CN, $C_{1-6}$ alkyl, —($C_{1-6}$ alkyl)OH, and $C_{1-6}$ haloalkyl.

14. The method of claim 1, wherein the compound of formula (I) is chosen from:

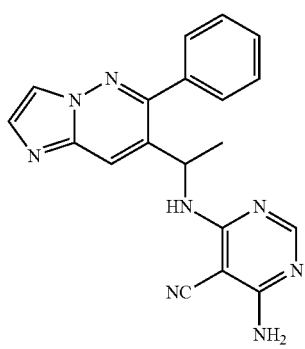

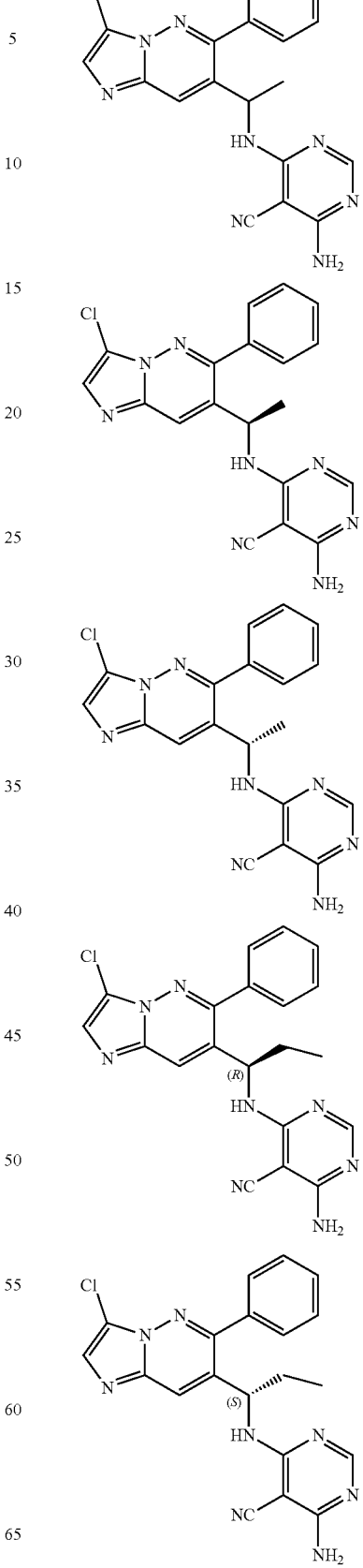

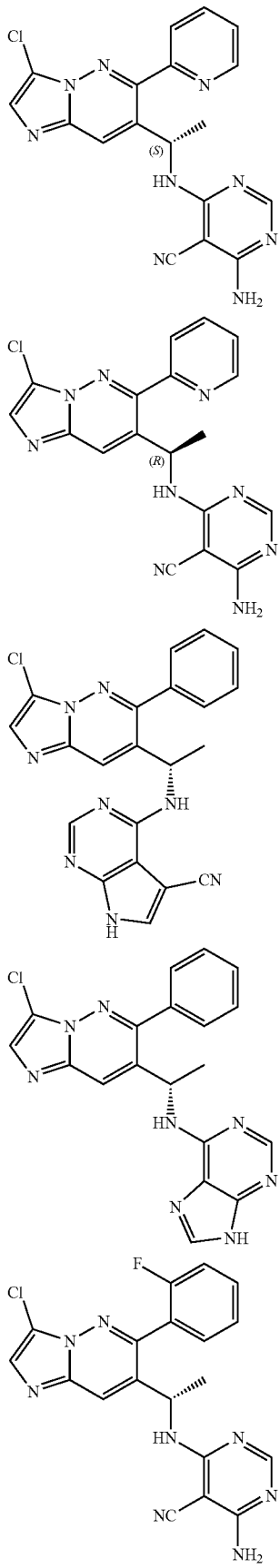

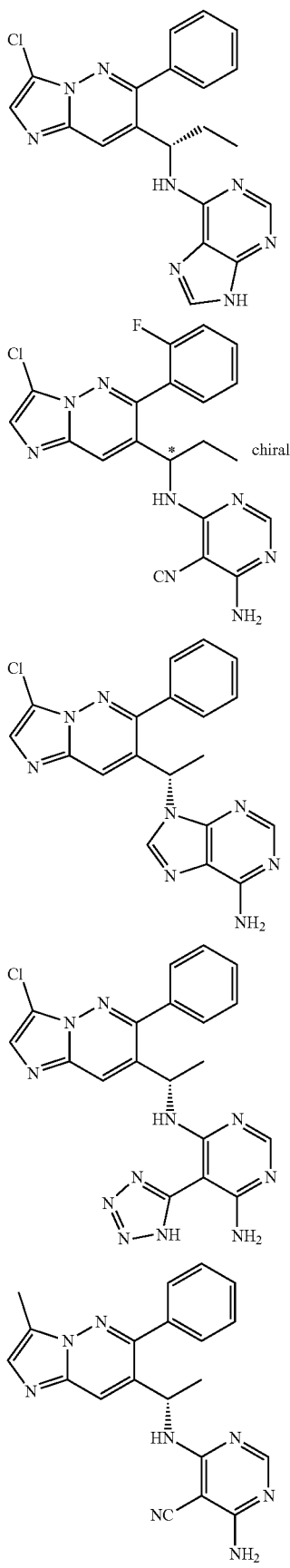
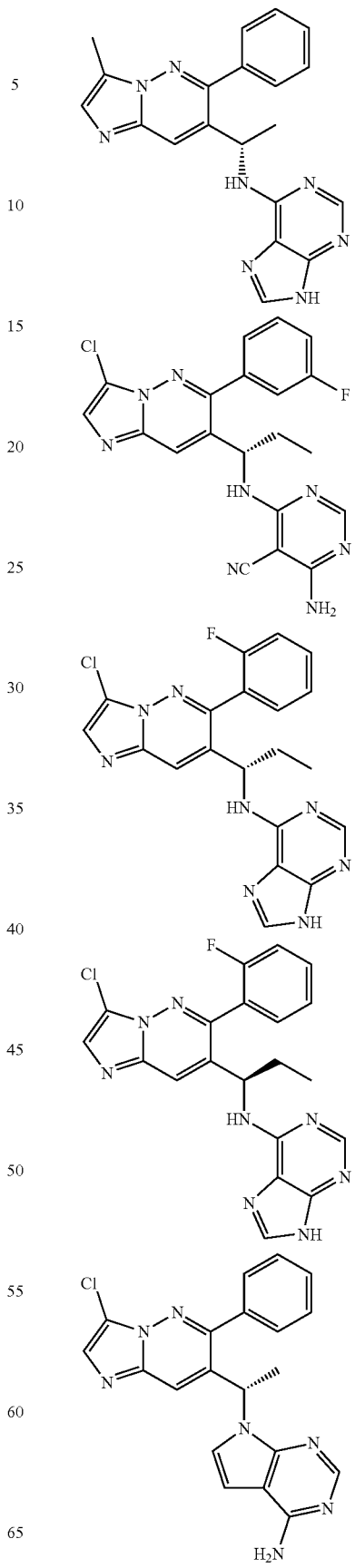

-continued
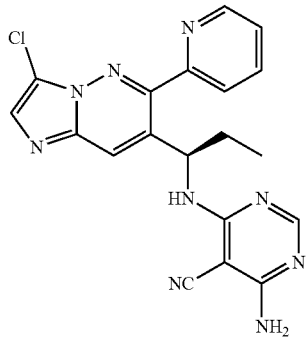
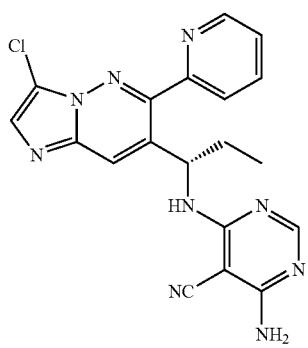
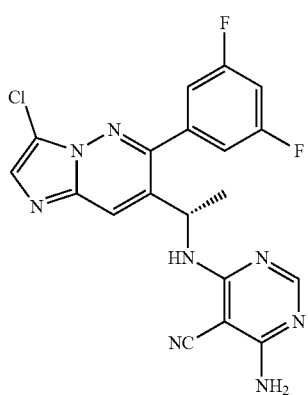
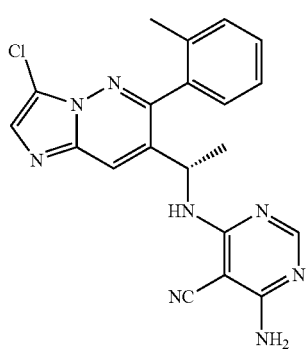
-continued
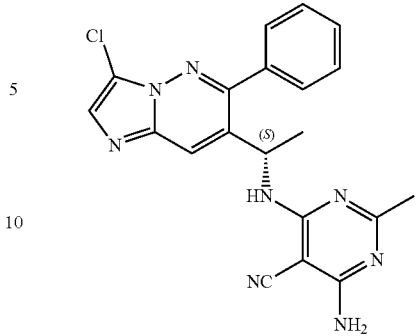
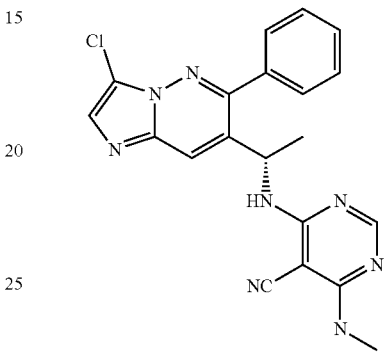
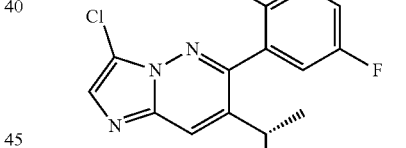
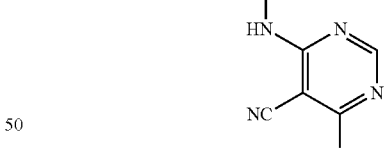
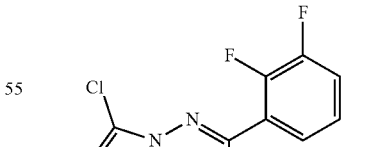
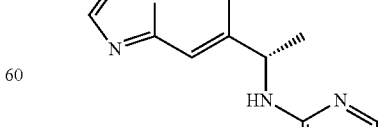
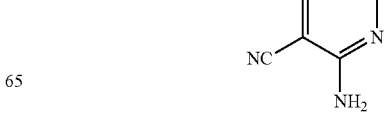

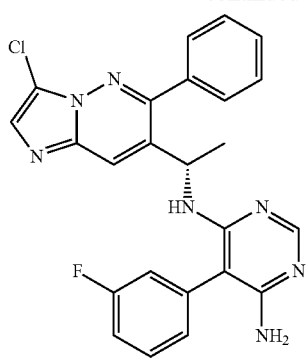
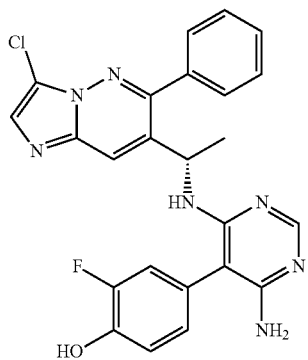
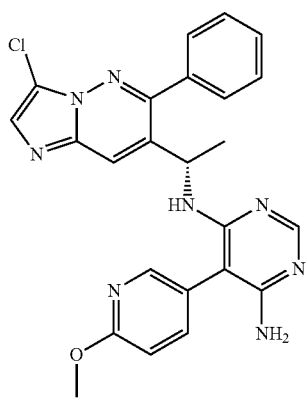
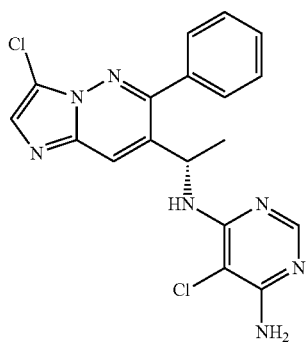
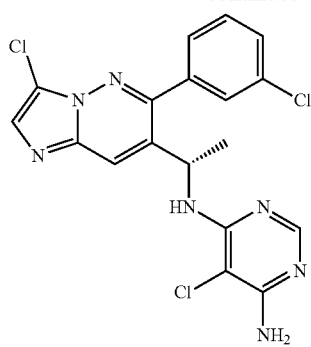
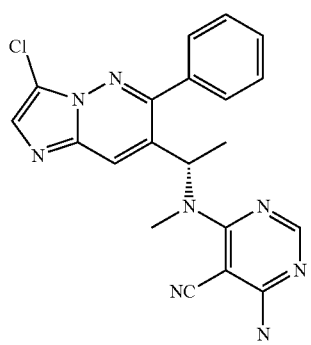
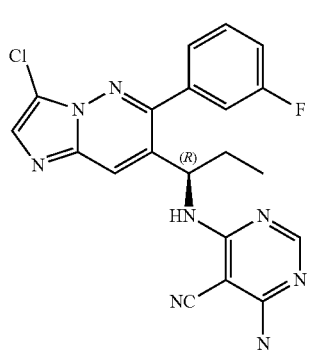
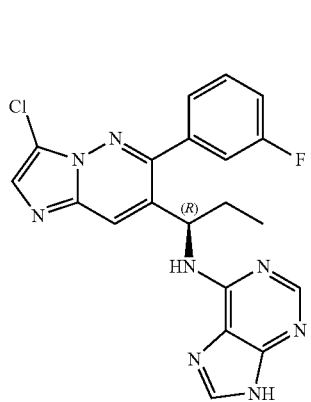

141
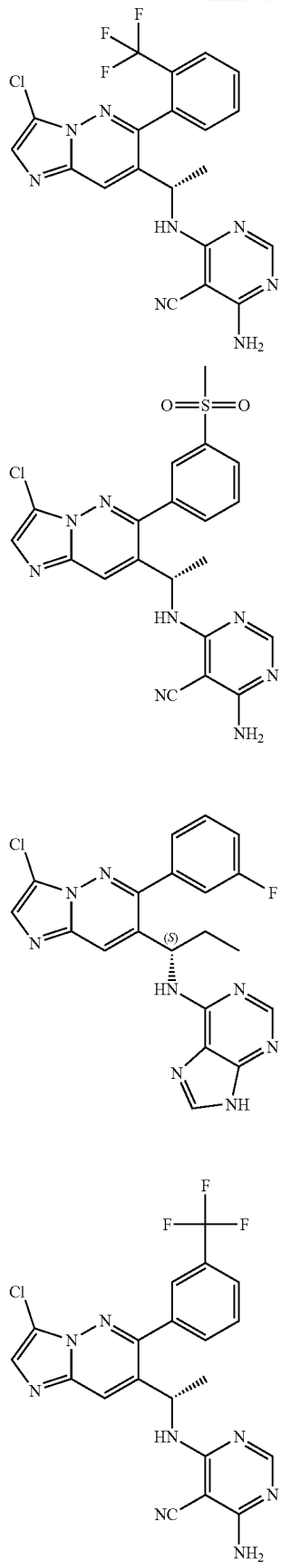
142
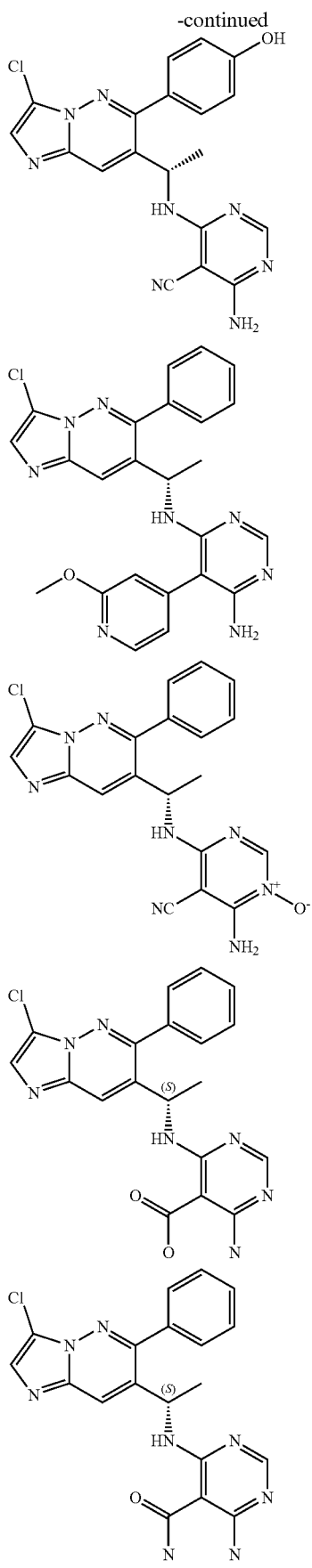

143
-continued
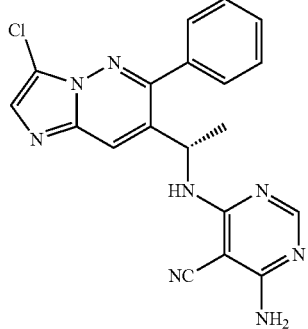
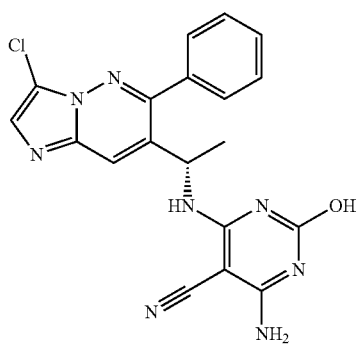
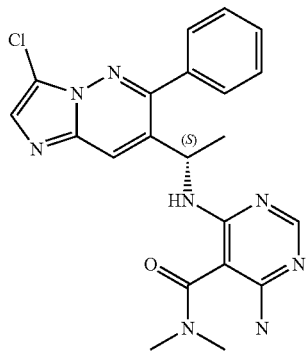
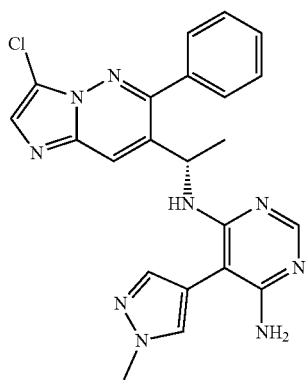
144
-continued
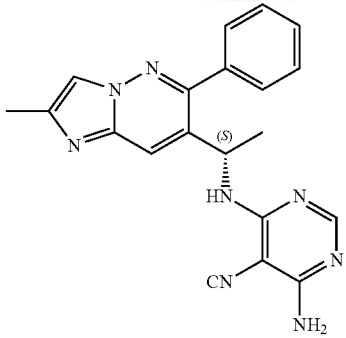
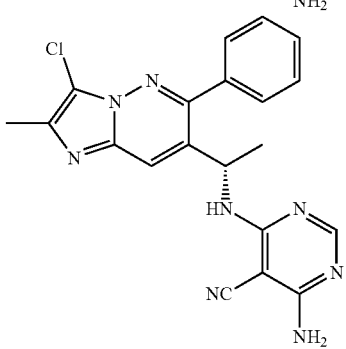
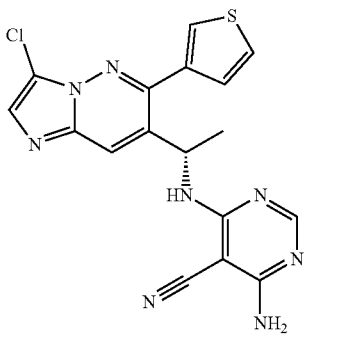
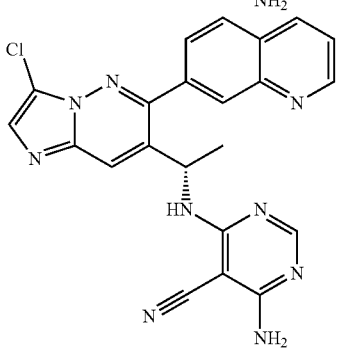
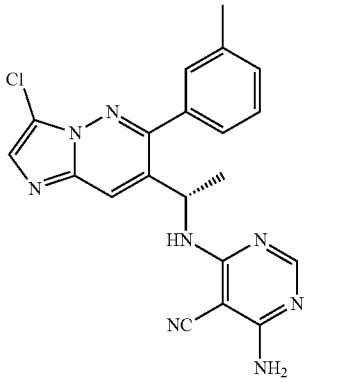

145
-continued
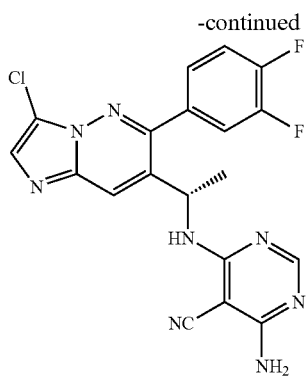
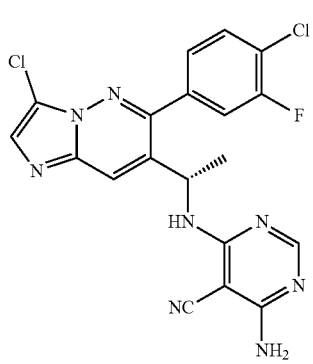
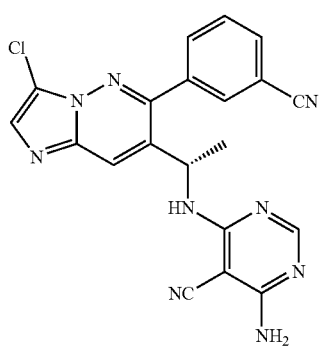
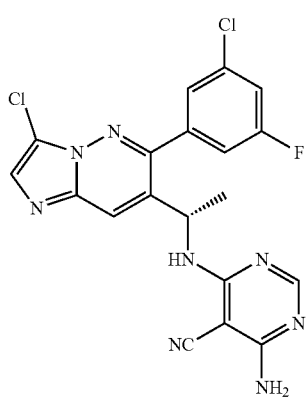
146
-continued
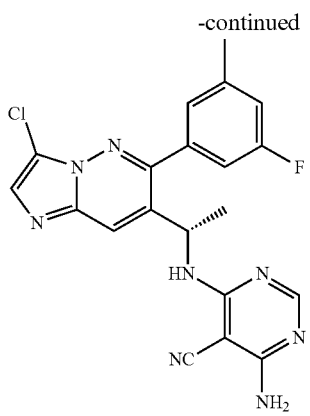
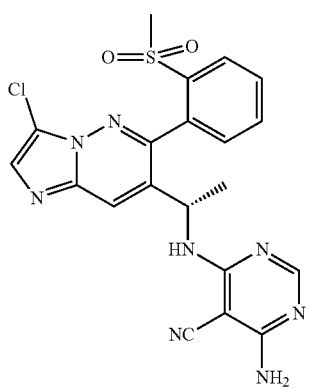
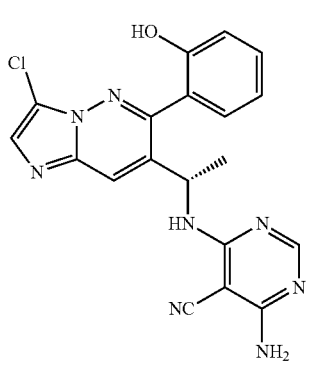
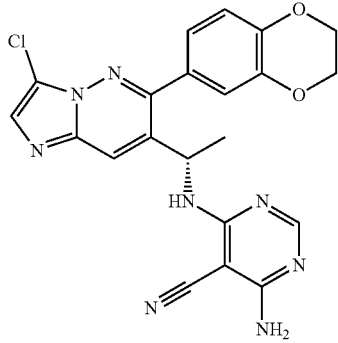

147
-continued
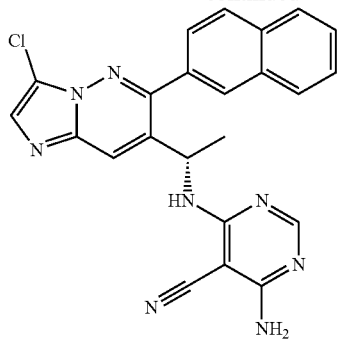
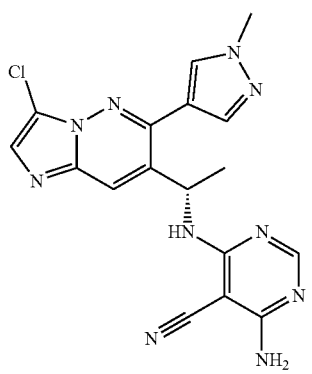
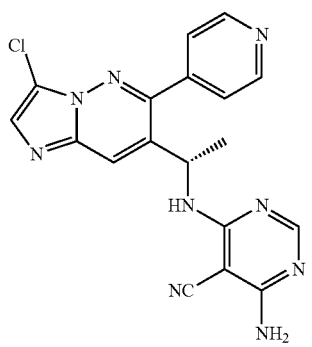
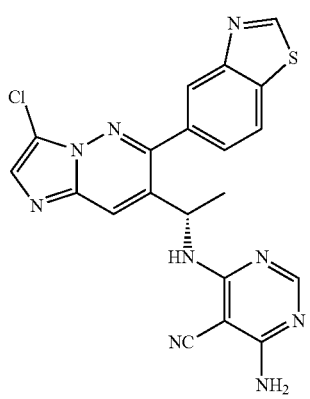
148
-continued
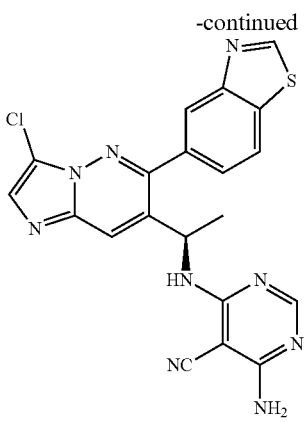
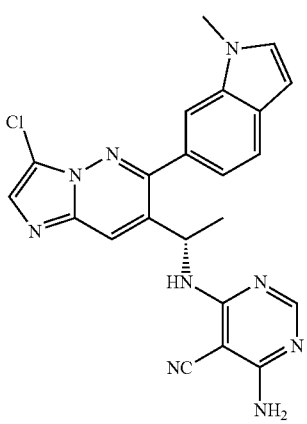
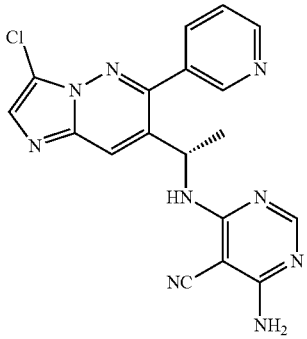
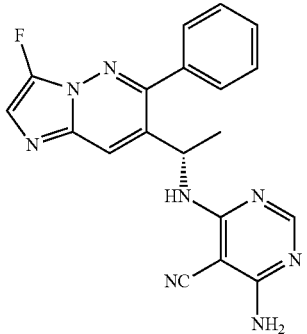

-continued

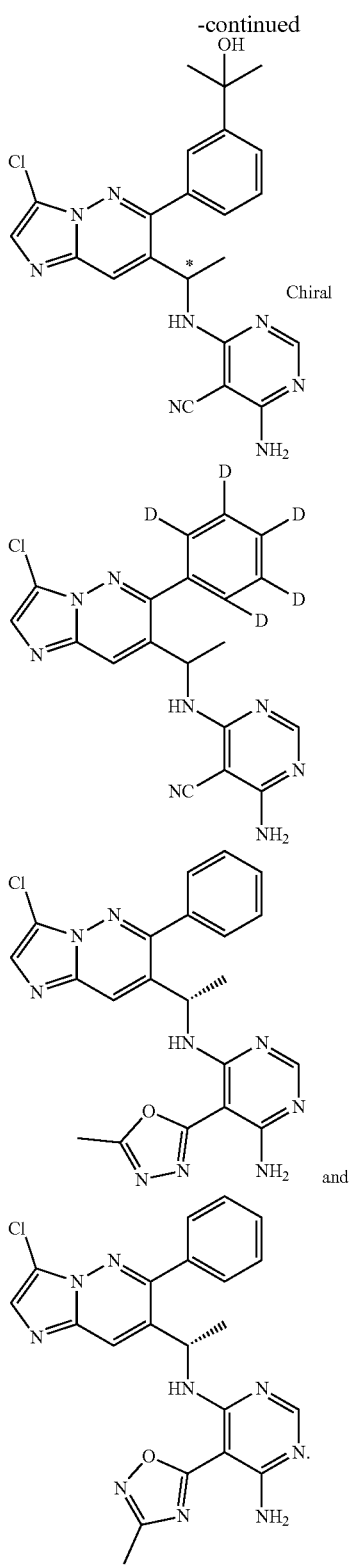

and

15. A method of inhibiting the activity of PI₃K in a subject suffering from a disease in need thereof, comprising contacting the PI₃K with an effective amount of a compound of formula (I),

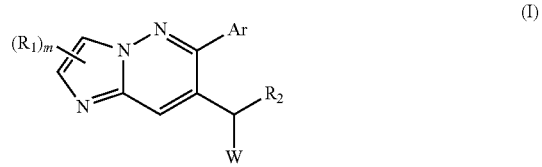

(I)

and/or a pharmaceutically acceptable salt thereof, and/or solvates, racemic mixture, enantiomers, diastereomers, and tautomers thereof, wherein Ar is aryl or heteroaryl, each of which is optionally substituted with one or more groups chosen from deuterium, halo, —CN, —OH, —SH, $C_{1-6}$ alkyl, $C_{2-6}$ alkenyl, $C_{2-6}$ alkynyl, $C_{1-6}$ haloalkyl, —O($C_{1-6}$ alkyl), —($C_{1-6}$ alkyl)OH, —NH₂, —NH($C_{1-6}$ alkyl), —N($C_{1-6}$ alkyl)($C_{1-6}$ alkyl), and —S(O)₂($C_{1-6}$ alkyl);

W is chosen from heteroaryl and —N(R₃)heteroaryl, wherein said heteroaryl is optionally substituted with one or more groups chosen from halo, —CN, —OH, —SH, $C_{1-6}$ alkyl, $C_{2-6}$ alkenyl, $C_{2-6}$ alkynyl, $C_{1-6}$ haloalkyl, —O($C_{1-6}$ alkyl), —($C_{1-6}$ alkyl)OH, —NH₂, —NH($C_{1-6}$ alkyl), —N($C_{1-6}$ alkyl)($C_{1-6}$ alkyl), —COOH, —C(O)NH₂, —C(O)NH($C_{1-6}$ alkyl), —C(O)N($C_{1-6}$ alkyl)($C_{1-6}$ alkyl), —SO₂($C_{1-6}$ alkyl), phenyl, and 5- or 6-membered heteroaryl; in which each of said phenyl or 5- or 6-membered heteroaryl as the substituent of W is optionally substituted with one or more groups chosen from halo, —CN, —OH, —SH, $C_{1-6}$ alkyl, $C_{1-6}$ haloalkyl, —O($C_{1-6}$ alkyl), —($C_{1-6}$ alkyl)OH, —NH₂, —NH($C_{1-6}$ alkyl), and —N($C_{1-6}$ alkyl)($C_{1-6}$ alkyl);

R₁ is independently chosen from H, halo, —CN, $C_{1-6}$ alkyl, $C_{1-6}$ haloalkyl, —($C_{1-6}$ alkyl)OH, —($C_{1-6}$ alkyl)O($C_{1-6}$ alkyl), and $C_{2-6}$ alkynyl;

R₂ is chosen from H, $C_{1-6}$ alkyl, and $C_{3-8}$ cycloalkyl, each of which except for H, is optionally substituted with one or more groups chosen from halo, —CN, $C_{1-6}$ alkyl, $C_{1-6}$ haloalkyl, and —OH;

R₃ is H or $C_{1-6}$ alkyl;

m is 1 or 2;

wherein said disease is rheumatoid arthritis or B-cell lymphoma.

16. The method of claim 1, wherein the disease is rheumatoid arthritis.

17. The method of claim 1, wherein the disease is B-cell lymphoma.

18. The method of claim 15, wherein the disease is rheumatoid arthritis.

19. The method of claim 15, wherein the disease is B-cell lymphoma.

* * * * *